US012582700B2

(12) United States Patent
Seehra et al.

(10) Patent No.: US 12,582,700 B2
(45) Date of Patent: ***Mar. 24, 2026

(54) ACTIVIN RECEPTOR TYPE IIA VARIANTS AND METHODS OF USE THEREOF

(71) Applicant: Keros Therapeutics, Inc., Lexington, MA (US)

(72) Inventors: Jasbir S. Seehra, Lexington, MA (US); Jennifer Lachey, Lincoln, MA (US)

(73) Assignee: Keros Therapeutics, Inc., Lexington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/229,468

(22) Filed: Jun. 5, 2025

(65) Prior Publication Data

US 2025/0295735 A1      Sep. 25, 2025

Related U.S. Application Data

(60) Continuation of application No. 18/219,336, filed on Jul. 7, 2023, now Pat. No. 12,350,313, which is a continuation of application No. 17/327,914, filed on May 24, 2021, now Pat. No. 11,717,558, which is a division of application No. 16/348,987, filed as application No. PCT/US2017/060960 on Nov. 9, 2017, now Pat. No. 11,013,785.

(60) Provisional application No. 62/531,943, filed on Jul. 13, 2017, provisional application No. 62/420,476, filed on Nov. 10, 2016.

(51) Int. Cl.
| | |
|---|---|
| *A61K 38/18* | (2006.01) |
| *A61K 47/65* | (2017.01) |
| *A61P 19/08* | (2006.01) |
| *C07K 14/71* | (2006.01) |
| *C07K 14/76* | (2006.01) |
| *C12N 15/85* | (2006.01) |
| *C12P 21/02* | (2006.01) |
| *A61K 38/00* | (2006.01) |
| *A61K 47/64* | (2017.01) |

(52) U.S. Cl.
CPC ............. *A61K 38/18* (2013.01); *A61K 47/65* (2017.08); *A61P 19/08* (2018.01); *C07K 14/71* (2013.01); *C07K 14/76* (2013.01); *C12N 15/85* (2013.01); *C12P 21/02* (2013.01); *A61K 38/00* (2013.01); *A61K 47/64* (2017.08)

(58) Field of Classification Search
None
See application file for complete search history.

(56) References Cited

U.S. PATENT DOCUMENTS

| | | | |
|---|---|---|---|
| 7,612,041 | B2 | 11/2009 | Knopf et al. |
| 7,709,605 | B2 | 5/2010 | Knopf et al. |
| 7,842,663 | B2 | 11/2010 | Knopf et al. |
| 7,947,646 | B2 | 5/2011 | Sun et al. |
| 7,951,771 | B2 | 5/2011 | Knopf et al. |
| 7,960,343 | B2 | 6/2011 | Knopf et al. |
| 7,988,973 | B2 | 8/2011 | Sherman |
| 8,007,809 | B2 | 8/2011 | Sherman |
| 8,058,229 | B2 | 11/2011 | Seehra et al. |
| 8,067,360 | B2 | 11/2011 | Knopf et al. |
| 8,067,562 | B2 | 11/2011 | Han et al. |
| 8,101,564 | B2 | 1/2012 | Choi et al. |
| 8,138,142 | B2 | 3/2012 | Seehra et al. |
| 8,173,601 | B2 | 5/2012 | Knopf et al. |
| 8,178,488 | B2 | 5/2012 | Knopf et al. |
| 8,216,997 | B2 | 7/2012 | Seehra et al. |
| 8,252,900 | B2 | 8/2012 | Knopf et al. |
| 8,293,881 | B2 | 10/2012 | Seehra et al. |
| 8,343,933 | B2 | 1/2013 | Knopf et al. |
| 8,361,957 | B2 | 1/2013 | Seehra et al. |
| 8,367,611 | B2 | 2/2013 | Knopf et al. |
| 8,501,768 | B2 | 8/2013 | Conte et al. |
| 8,614,292 | B2 | 12/2013 | Han et al. |
| 8,629,109 | B2 | 1/2014 | Knopf et al. |
| 8,703,927 | B2 | 4/2014 | Seehra et al. |
| 8,710,016 | B2 | 4/2014 | Seehra et al. |
| 8,716,459 | B2 | 5/2014 | Sun et al. |
| 8,871,209 | B2 | 10/2014 | Stitt et al. |

(Continued)

FOREIGN PATENT DOCUMENTS

| | | |
|---|---|---|
| EP | 2314617 A2 | 4/2011 |
| EP | 2594280 A1 | 5/2013 |

(Continued)

OTHER PUBLICATIONS

International Search Report and Written Opinion for International Application No. PCT/US2017/060960, mailed Aug. 9, 2018.

(Continued)

*Primary Examiner* — Christine J Saoud
*Assistant Examiner* — Jon M Lockard
(74) *Attorney, Agent, or Firm* — Wolf, Greenfield & Sacks, P.C.

(57)      ABSTRACT

The invention features polypeptides that include an extracellular ActRIIa variant. In some embodiments, a polypeptide of the invention includes an extracellular ActRIIa variant fused to an Fc domain monomer or moiety. The invention also features pharmaceutical compositions and methods of using the polypeptides to treat diseases and conditions involving weakness and atrophy of muscles, e.g., Duchenne muscular dystrophy, facioscapulohumeral muscular dystrophy, inclusion body myositis, amyotrophic lateral sclerosis, sarcopenia; or cancer cachexia; or metabolic diseases, e.g., obesity, Type-1 diabetes, or Type-2 diabetes.

6 Claims, 11 Drawing Sheets

Specification includes a Sequence Listing.

(56) References Cited

U.S. PATENT DOCUMENTS

| | | | |
|---|---|---|---|
| 8,895,016 | B2 | 11/2014 | Sherman et al. |
| 8,999,917 | B2 | 4/2015 | Sun et al. |
| 9,138,459 | B2 | 9/2015 | Knopf et al. |
| 9,163,075 | B2 | 10/2015 | Knopf et al. |
| 9,181,533 | B2 | 11/2015 | Seehra et al. |
| 9,273,114 | B2 | 3/2016 | Sun et al. |
| 9,284,364 | B2 | 3/2016 | Han et al. |
| 9,353,356 | B2 | 5/2016 | Knopf et al. |
| 9,399,669 | B2 | 7/2016 | Knopf et al. |
| 9,439,945 | B2 | 9/2016 | Seehra et al. |
| 9,447,165 | B2 | 9/2016 | Sun et al. |
| 9,493,556 | B2 | 11/2016 | Seehra et al. |
| 9,505,813 | B2 | 11/2016 | Seehra et al. |
| 9,526,759 | B2 | 12/2016 | Knopf et al. |
| 9,572,865 | B2 | 2/2017 | Knopf et al. |
| 9,610,327 | B2 | 4/2017 | Knopf et al. |
| 9,617,319 | B2 | 4/2017 | Seehra et al. |
| 9,745,559 | B2 | 8/2017 | Seehra et al. |
| 9,809,638 | B2 | 11/2017 | Sun et al. |
| 9,850,298 | B2 | 12/2017 | Attie |
| 9,932,379 | B2 | 4/2018 | Seehra et al. |
| 10,093,707 | B2 | 10/2018 | Sherman et al. |
| 10,131,700 | B2 | 11/2018 | Seehra et al. |
| 10,189,882 | B2 | 1/2019 | Attie et al. |
| 10,227,393 | B2 | 3/2019 | Kumar et al. |
| 10,259,861 | B2 | 4/2019 | Knopf et al. |
| 10,308,704 | B2 | 6/2019 | Sun et al. |
| 10,358,476 | B2 | 7/2019 | Kumar et al. |
| 10,358,633 | B2 | 7/2019 | Seehra et al. |
| 10,377,996 | B2 | 8/2019 | Seehra et al. |
| 10,407,487 | B2 | 9/2019 | Sun et al. |
| 10,487,144 | B2 | 11/2019 | Attie |
| 10,550,170 | B2 | 2/2020 | Sherman et al. |
| 11,013,785 | B2 | 5/2021 | Seehra et al. |
| 11,090,361 | B2 | 8/2021 | Seehra et al. |
| 11,484,573 | B2 | 11/2022 | Lachey et al. |
| 11,717,558 | B2 | 8/2023 | Seehra et al. |
| 11,884,715 | B2 | 1/2024 | Seehra et al. |
| 12,350,313 | B2 | 7/2025 | Seehra et al. |
| 2006/0068468 | A1 | 3/2006 | Knopf et al. |
| 2009/0005308 | A1 | 1/2009 | Knopf et al. |
| 2009/0163417 | A1 | 6/2009 | Sherman |
| 2010/0028331 | A1 | 2/2010 | Sherman et al. |
| 2010/0028332 | A1 | 2/2010 | Sherman et al. |
| 2010/0068215 | A1 | 3/2010 | Seehra et al. |
| 2010/0266591 | A1 | 10/2010 | Bugelski et al. |
| 2010/0267133 | A1 | 10/2010 | Knopf et al. |
| 2010/0316644 | A1 | 12/2010 | Seehra et al. |
| 2011/0038831 | A1 | 2/2011 | Seehra et al. |
| 2011/0092670 | A1 | 4/2011 | Knopf et al. |
| 2011/0135638 | A1 | 6/2011 | Seehra et al. |
| 2011/0250198 | A1 | 10/2011 | Wolfman et al. |
| 2012/0015877 | A1 | 1/2012 | Seehra et al. |
| 2012/0121576 | A1 | 5/2012 | Seehra et al. |
| 2012/0148588 | A1 | 6/2012 | Knopf et al. |
| 2013/0065299 | A1 | 3/2013 | Knopf et al. |
| 2013/0071393 | A1 | 3/2013 | Seehra et al. |
| 2013/0177559 | A1 | 7/2013 | Seehra et al. |
| 2013/0288983 | A1 | 10/2013 | Sun et al. |
| 2013/0315924 | A1 | 11/2013 | Hsu et al. |
| 2014/0079700 | A1 | 3/2014 | Knopf et al. |
| 2014/0314759 | A1 | 10/2014 | Seehra et al. |
| 2015/0023970 | A1 | 1/2015 | Seehra et al. |
| 2015/0023981 | A1 | 1/2015 | De Kretser et al. |
| 2015/0030595 | A1 | 1/2015 | Lee et al. |
| 2015/0183845 | A1 | 7/2015 | Sherman et al. |
| 2016/0039922 | A1 | 2/2016 | Attie |
| 2016/0108379 | A1 | 4/2016 | Knopf et al. |
| 2016/0298093 | A1 | 10/2016 | Kumar et al. |
| 2016/0333418 | A1 | 11/2016 | Haqq |
| 2017/0058016 | A1 | 3/2017 | Knopf et al. |
| 2017/0327800 | A1 | 11/2017 | Seehra et al. |
| 2017/0360887 | A1 | 12/2017 | Attie et al. |
| 2018/0050089 | A1 | 2/2018 | Kumar et al. |
| 2018/0125928 | A1 | 5/2018 | Attie et al. |
| 2018/0148491 | A1 | 5/2018 | Han et al. |
| 2018/0161426 | A1 | 6/2018 | Cappellini et al. |
| 2018/0334673 | A1 | 11/2018 | Wood et al. |
| 2019/0085067 | A1 | 3/2019 | Schurpf et al. |
| 2019/0151463 | A1 | 5/2019 | Gegg et al. |
| 2019/0225664 | A1 | 7/2019 | Sherman et al. |
| 2019/0233486 | A1 | 8/2019 | Attie et al. |
| 2019/0256605 | A1 | 8/2019 | Han et al. |
| 2019/0282663 | A1 | 9/2019 | Seehra et al. |
| 2019/0284251 | A1 | 9/2019 | Seehra et al. |
| 2019/0330307 | A1 | 10/2019 | Han et al. |
| 2019/0345225 | A1 | 11/2019 | Seehra et al. |
| 2019/0352619 | A1 | 11/2019 | Knopf et al. |
| 2020/0055919 | A1 | 2/2020 | Kumar et al. |
| 2020/0071381 | A1 | 3/2020 | Knopf et al. |
| 2020/0407415 | A1 | 12/2020 | Seehra et al. |
| 2021/0030841 | A1 | 2/2021 | Lachey et al. |
| 2021/0052698 | A1 | 2/2021 | Seehra et al. |
| 2021/0275637 | A1 | 9/2021 | Seehra et al. |
| 2023/0079602 | A1 | 3/2023 | Seehra et al. |
| 2023/0087128 | A1 | 3/2023 | Seehra et al. |
| 2023/0265162 | A1 | 8/2023 | Seehra et al. |
| 2023/0348565 | A1 | 11/2023 | Seehra et al. |
| 2024/0050528 | A1 | 2/2024 | Seehra et al. |
| 2024/0141012 | A1 | 5/2024 | Seehra et al. |
| 2024/0218061 | A1 | 7/2024 | Seehra et al. |
| 2024/0228583 | A1 | 7/2024 | Seehra et al. |
| 2024/0252631 | A1 | 8/2024 | Seehra et al. |

FOREIGN PATENT DOCUMENTS

| | | | |
|---|---|---|---|
| WO | WO 2004/039948 | A2 | 5/2004 |
| WO | WO 2006/012627 | A2 | 2/2006 |
| WO | WO 2006/012627 | A3 | 5/2006 |
| WO | WO 2008/076437 | A2 | 6/2008 |
| WO | WO 2008/094708 | A2 | 8/2008 |
| WO | WO 2008/097541 | A2 | 8/2008 |
| WO | WO 2008/100384 | A2 | 8/2008 |
| WO | WO 2009/015345 | A1 | 1/2009 |
| WO | WO 2009/158025 | A2 | 12/2009 |
| WO | WO 2009/158033 | A2 | 12/2009 |
| WO | WO 2009/158035 | A2 | 12/2009 |
| WO | WO 2009/158015 | A3 | 3/2010 |
| WO | WO 2010/062383 | A2 | 6/2010 |
| WO | WO 2010/083034 | A1 | 7/2010 |
| WO | WO 2010/151426 | A1 | 12/2010 |
| WO | WO 2011/020045 | A1 | 2/2011 |
| WO | WO 2011/031901 | A1 | 3/2011 |
| WO | WO 2011/056896 | A1 | 5/2011 |
| WO | WO 2011/063018 | A1 | 5/2011 |
| WO | WO 2012/027065 | A2 | 3/2012 |
| WO | WO 2012/064771 | A1 | 5/2012 |
| WO | WO 2013/059347 | A1 | 4/2013 |
| WO | WO 2013/188448 | A3 | 4/2014 |
| WO | WO 2014/066487 | A2 | 5/2014 |
| WO | WO 2014/138485 | A1 | 9/2014 |
| WO | WO 2014/144903 | A1 | 9/2014 |
| WO | WO 2015/143403 | A1 | 9/2015 |
| WO | WO 2015/161220 | A1 | 10/2015 |
| WO | WO 2015/192111 | A1 | 12/2015 |
| WO | WO 2015/192127 | A2 | 12/2015 |
| WO | WO 2016/069234 | A1 | 5/2016 |
| WO | WO 2016/090077 | A1 | 6/2016 |
| WO | WO 2016/090188 | A1 | 6/2016 |
| WO | WO 2016/164501 | A1 | 10/2016 |
| WO | WO 2016/171948 | A1 | 10/2016 |
| WO | WO 2016/187378 | A1 | 11/2016 |
| WO | WO 2017/079591 | A2 | 5/2017 |
| WO | WO 2017/091706 | A1 | 6/2017 |
| WO | WO 2017/147182 | A1 | 8/2017 |
| WO | WO 2018/013936 | A1 | 1/2018 |
| WO | WO 2018/022762 | A1 | 2/2018 |
| WO | WO 2018/067740 | A1 | 4/2018 |
| WO | WO 2018/067874 | A1 | 4/2018 |
| WO | WO 2018/075747 | A1 | 4/2018 |
| WO | WO 2018/089706 | A2 | 5/2018 |
| WO | WO 2018/089715 | A1 | 5/2018 |
| WO | WO 2018/100483 | A1 | 6/2018 |
| WO | WO 2018/144542 | A1 | 8/2018 |

(56) References Cited

FOREIGN PATENT DOCUMENTS

| | | | |
|---|---|---|---|
| WO | WO 2018/144968 A1 | 8/2018 |
| WO | WO 2018/231905 A1 | 12/2018 |
| WO | WO 2019/094751 A1 | 5/2019 |
| WO | WO 2019/140283 A1 | 7/2019 |
| WO | WO 2019/217715 A1 | 11/2019 |
| WO | WO 2021/062163 A1 | 4/2021 |
| WO | WO 2021/189006 A1 | 9/2021 |
| WO | WO 2021/189010 A1 | 9/2021 |
| WO | WO 2021/189019 A1 | 9/2021 |
| WO | WO 2022/072882 A1 | 4/2022 |
| WO | WO 2022/235620 A1 | 11/2022 |
| WO | WO 2022/271716 A2 | 12/2022 |
| WO | WO 2023/023345 A2 | 2/2023 |
| WO | WO 2024/054985 A2 | 3/2024 |
| WO | WO 2024/102906 A2 | 5/2024 |
| WO | WO 2024/238920 A1 | 11/2024 |
| WO | WO 2024/238950 A1 | 11/2024 |

OTHER PUBLICATIONS

International Preliminary Report on Patentability for International Application No. PCT/US2017/060960, mailed May 23, 2019.

International Search Report and Written Opinion for International Application No. PCT/US2017/060970, mailed Mar. 27, 2018.

International Preliminary Report on Patentability for International Application No. PCT/US2017/060970, mailed May 23, 2019.

International Search Report and Written Opinion for International Application No. PCT/US2018/060076, mailed Mar. 14, 2019.

International Preliminary Report on Patentability for International Application No. PCT/US2018/060076, mailed May 22, 2020.

International Search Report and Written Opinion for International Application No. PCT/US2019/013329, mailed May 13, 2019.

International Preliminary Report on Patentability for International Application No. PCT/US2019/013329, mailed Dec. 8, 2020.

International Search Report and Written Opinion for International Application No. PCT/US2019/031573, mailed Sep. 17, 2019.

International Preliminary Report on Patentability for International Application No. PCT/US2019/031573, mailed Nov. 19, 2020.

International Search Report and Written Opinion for International Application No. PCT/US2021/023353, mailed Jul. 20, 2021.

International Preliminary Report on Patentability for International Application No. PCT/US2021/023353, mailed Sep. 29, 2022.

International Search Report and Written Opinion for International Application No. PCT/US2021/023339, mailed Jun. 21, 2021.

International Preliminary Report on Patentability for International Application No. PCT/US2021/023339, mailed Sep. 29, 2022.

International Search Report and Written Opinion for International Application No. PCT/US2021/023335, mailed Jul. 9, 2021.

International Preliminary Report on Patentability for International Application No. PCT/US2021/023335, mailed Sep. 29, 2022.

International Search Report and Written Opinion for International Application No. PCT/US2021/053239, mailed Feb. 23, 2022.

International Preliminary Report on Patentability for International Application No. PCT/US2021/053239, mailed Apr. 13, 2023.

International Search Report and Written Opinion for International Application No. PCT/US2022/040920, mailed Mar. 29, 2023.

International Preliminary Report on Patentability for International Application No. PCT/US2022/040920, mailed Feb. 29, 2024.

International Search Report and Written Opinion for International Application No. PCT/US2022/034366, mailed Jan. 4, 2023.

International Preliminary Report on Patentability for International Application No. PCT/US2022/034366, mailed Oct. 18, 2023.

International Search Report and Written Opinion for International Application No. PCT/US2022/027399, mailed Sep. 21, 2022.

International Preliminary Report on Patentability for International Application No. PCT/US2022/027399, mailed Nov. 16, 2023.

Extended European Search Report for Application No. 17870560.4, mailed Jun. 19, 2020.

Abdulkadyrov et al., Sotatercept in Patients with Osteolytic Lesions of Multiple Myeloma. Br J Haematol. Jun. 2014;165(6):814-23. doi: 10.1111/bjh.12835. Epub Mar. 21, 2014.

Akpan et al., The effects of a soluble activin type IIB receptor on obesity and insulin sensitivity. Int J Obes (Lond). Nov. 2009;33(11):1265-73. doi: 10.1038/ijo.2009.162. Epub Aug. 11, 2009.

Attie et al., A phase 1 study of ACE-536, a regulator of erythroid differentiation, in healthy volunteers. Am J Hematol. Jul. 2014;89(7):766-70. doi: 10.1002/ajh.23732. Epub Apr. 26, 2014.

Attie et al., A single ascending-dose study of muscle regulator ACE-031 in healthy volunteers. Muscle Nerve. Mar. 2013;47(3):416-23. doi: 10.1002/mus.23539. Epub Nov. 21, 2012.

Badesch et al., "Pulsar: A Phase 2, Randomized, Double-Blind, Placebo-Controlled Study to Assess the Efficacy and Safety of Sotatercept (ACE-O11) When Added to Standard of Care for the Treatment of Pulmonary Arterial Hypertension (PAH)," ERS International Congress Sep. 28-Oct. 2, 2019, Madrid, Spain, Poster PA475O, Abstract 19918, retrieved from <acceleronpharma.com/wp-contentluploads/2O19/1 O/Badesch-et-al-ERS-2O19-PULSAR-TIP-Poster_FINAL-2.pdf> (2019).

Ballen et al., Outcome of transplantation for myelofibrosis. Biol Blood Marrow Transplant. Mar. 2010;16(3):358-67. doi: 10.1016/j.bbmt.2009.10.025. Epub Oct. 30, 2009.

Bauer et al., Complement C3 deficiency attenuates chronic hypoxia-induced pulmonary hypertension in mice. PLoS One. 2011;6(12):e28578. doi: 10.1371/journal.pone.0028578. Epub Dec. 14, 2011.

Bernstein et al., Activin Decoy Receptor ActRIIB:Fc Lowers FSH and Therapeutically Restores Oocyte Yield, Prevents Oocyte Chromosome Misalignments and Spindle Aberrations, and Increases Fertility in Midlife Female SAMP8 Mice. Endocrinology. Mar. 2016;157(3):1234-47. doi: 10.1210/en.2015-1702. Epub Dec. 29, 2015.

Bond et al., Modeling Energy Dynamics in Mice with Skeletal Muscle Hypertrophy Fed High Calorie Diets. Int J Biol Sci. Apr. 1, 2016;12(5):617-30. doi: 10.7150/ijbs.13525. eCollection 2016.

Bose et al., Management of Myelofibrosis-Related Cytopenias. Curr Hematol Malig Rep. Jun. 2018;13(3):164-172. doi: 10.1007/s11899-018-0447-9.

Cadena et al., Administration of a soluble activin type IIB receptor promotes skeletal muscle growth independent of fiber type. J Appl Physiol (1985). Sep. 2010;109(3):635-42. doi: 10.1152/japplphysiol.00866.2009. Epub May 13, 2010.

Campbell et al., Myostatin inhibitor ACE-031 treatment of ambulatory boys with Duchenne muscular dystrophy: Results of a randomized, placebo-controlled clinical trial. Muscle Nerve. Apr. 2017;55(4):458-464. doi: 10.1002/mus.25268. Epub Dec. 23, 2016.

Cappellini et al., A Phase 2a, Open-Label, Dose-Finding Study To Determine The Safety and Tolerability Of Sotatercept (ACE-O11) In Adults With Beta-Thalassemia: Interim Results. 55th Annual Meeting of the American Society of Hematology (ASH), Dec.r 7-10, New Orleans, LA. Poster 3448 (2013).

Cappellini et al., The BELIEVE Trial: Results of a Phase 3, Randomized, Double-Blind, Placebo-Controlled Study of Luspatercept in Adult Beta-Thalassemia Patients Who Require Regular Red Blood Cell (RBC) Transfusions. 60th Annual Meeting of the American Society of Hematology (ASH), Dec. 1-4, San Diego CA, Oral Presentation, retrieved from <http://acceleronpharma.com/wp-content/uploads/2018/12/BELIEVE-ASH-2O18-oral-Presentation-for-upload.pdf> (Dec. 2018).

Carlson et al., Soluble activin receptor type IIB increases forward pulling tension in the mdx mouse. Muscle Nerve. May 2011;43(5):694-9. doi: 10.1002/mus.21944. Epub Apr. 1, 2011.

Carrancio et al., Soluble activin receptor type IIB increases forward pulling tension in the mdx mouse. Br J Haematol. Jun. 2014;165(6):870-82. doi: 10.1111/bjh.12838. Epub Mar. 18, 2014.

Cash et al., The structure of myostatin:follistatin 288: insights into receptor utilization and heparin binding. EMBO J. Sep. 2, 2009;28(17):2662-76. doi: 10.1038/emboj.2009.205. Epub Jul. 30, 2009.

Chantry et al., Inhibiting activin-A signaling stimulates bone formation and prevents cancer-induced bone destruction in vivo. J Bone Miner Res. Dec. 2010;25(12):2633-46. doi: 10.1002/jbmr.142. Epub Jun. 7, 2010.

(56)                References Cited

OTHER PUBLICATIONS

Chen et al., Pharmacokinetics and Exposure-Response of Luspatercept in Patients With Anemia Due to Low- or Intermediate-1-Risk Myelodysplastic Syndromes (MOS): Preliminary Results From Phase 2 Studies. 58th Annual Meeting of the American Society of Hematology (ASH), Dec. 3-6, San Diego, California, Poster 1990, retrieved from <acceleronpharma.com/wpcontent/uploads/2017/O3/Chen-ASH-2O16-Poster-Luspatercept-PK-MDS.pdf>, (Dec. 2016).
Chen et al., Pharmacokinetics and Exposure-Response of Luspatercept in Patients With Beta-Thalassemia: Preliminary Results From Phase 2 Studies. 58th Annual Meeting of the American Society of Hematology (ASH), Dec. 3-6, San Diego, CA, Poster 2463, retrieved from <acceleronpharma.com/wp-content/uploads/2O17/O3/2O1612O4-Chen-ASH-2016-Poster-Luspatercept-PK-B-thal.pdf>, (Dec. 2016).
Dellanna, Safety and Hemoglobin Effect of Sotatercept, Administered Intravenously and Subcutaneously, for Maintenance of Hemoglobin in Hemodialysis Subjects: Interim Analysis of a Phase 2 Study. 48th Annual American Society of Nephrology Kidney Week, Nov. 3-8, San Diego, CA, retrieved from <acceleronpharma.com/wpcontent/uploads/2O17/O3/2015​11O6-ASN-2015_Sotatercept-REN-OO2-oral-Presentation_10-22-15-v3-Final.pdf>, (2015).
Digirolamo et al., Administration of soluble activin receptor 2B increases bone and muscle mass in a mouse model of osteogenesis imperfecta. Bone Res. Feb. 10, 2015:3:14042. doi: 10.1038/boneres. 2014.42. eCollection 2015.
Dussiot et al., An activin receptor IIA ligand trap corrects ineffective erythropoiesis in β-thalassemia. Nat Med. Apr. 2014;20(4):398-407. doi: 10.1038/nm.3468. Epub Mar. 23, 2014.
Ei-Shahawy et al., Interim Analysis of ACE-011-REN-001: The First 28 Day Dose Cycle of Low and Medium Starting Doses of Sotatercept Compared to Placebo for Correction of Anemia in Hemodialysis Subjects. National Kidney Foundation (NKF) 2014 Spring Clinical Meeting, Apr. 22-26, Las Vegas, NV, retrieved from <acceleronpharma.com/wpcontent/uploads/2O17 /O3/2O14o423-NKF-2014_REN-001-I nterim-Analysis-Poster_FINAL.pdf>, (2014).
El-Shahawy et al., "Long-term Effects of Sotatercept Compared With Placebo for Correction of Anemia in Hemodialysis Subjects: Interim Analysis of ACE-O11-REN-OO1 Phase 2A Study," 51st Congress of the European Renal Association and European Dialysis and Transplant Association, May 31-Jun. 3, Amsterdam, Poster SP244, retrieved from <acceleronpharma.com/wpcontent/uploads/2014/06/20140601-Long-Term-Effects-of-Sotatercept-Compared-with-Placebofor-Correction-of-Anemia.pdf>, (2014).
El-Shahawy et al., Safety and Hemoglobin Effect of the First 28-Day Dose Cycle of Sotatercept 0.7 mg/kg Compared With Lower Doses and Placebo for Correction of Anemia in Hemodialysis Subjects: Interim Analysis. American Society of Nephrology Kidney Week 2014, Nov. 11-16, Philadelphia, PA. Poster, retrieved from <acceleronpharma.com/wpcontent/uploads/2014/11/20141113-El-Shahawy-ASN-2014-Sotatercept-Safety-Poster.pdf>,(2014).
Fabre et al., Anti-Sclerostin Antibodies in Osteoporosis and Other Bone Diseases. J Clin Med. Oct. 26, 2020;9(11):3439. doi: 10.3390/jcm9113439.
Fajardo et al., Treatment with a soluble receptor for activin improves bone mass and structure in the axial and appendicular skeleton of female cynomolgus macaques (Macaca fascicularis). Bone. Jan. 2010;46(1):64-71. doi: 10.1016/j.bone.2009.09.018. Epub Sep. 23, 2009.
Fakhfakh et al., Administration of a soluble activin type IIB receptor promotes the transplantation of human myoblasts in dystrophic mice. Cell Transplant. 2012;21(7):1419-30. doi: 10.3727/096368911X627480.
Farrell et al., Bisphosphonate conjugation for bone specific drug targeting. Bone Rep. Jul. 3, 2018:9:47-60. doi: 10.1016/j.bonr.2018. 06.007. eCollection Dec. 2018.
Feigenson et al., Ker-O5O, a Modified Actriia Ligand Trap, Alleviates Cytopenia Arising from Multiple Etiologies. Blood. 136(Supplement 1):38 (2 Pages) (Nov. 2020).
Fenaux et al., Assessment of Longer-Term Efficacy and Safety in the Phase 3, Randomized, Double-Blind, Placebo-Controlled MEDAL-IST Trial of Luspatercept to Treat Anemia in IPSS-R Very Low-, Low-, or Int-Risk RBC Transfusion-Dependent MOS with Ring Sideroblasts. 61st Annual Meeting of the American Society of Hematology (ASH), Dec. 7-10, Orlando, Florida, retrieved from <acceleronpharma.com/wp-content/uploads/2019/12/ASH-2019-MEDALIST-longterm-analysis-Fenaux-oral-7-Dec-2019V2.odf>, (2019) (18 pages).
Fenaux et al., Luspatercept for the treatment of anemia in myelodysplastic syndromes and primary myelofibrosis. Blood. Feb. 21, 2019;133(8):790-794. doi: 10.1182/blood-2018-11-876888. Epub Jan. 2, 2019.
Fenaux et al., Luspatercept in Patients with Lower-Risk Myelodysplastic Syndromes. N Engl J Med. Jan. 9, 2020;382(2):140-151. doi: 10.1056/NEJMoa1908892.
Fenaux et al., The MEDALIST Trial: Results of a Phase 3, Randomized, Double-Blind, Placebo-Controlled Study of Luspatercept to Treat Patients With Very Low-, Low-, or Intermediate-Risk Myelodysplastic Syndromes (MOS) Associated Anemia With Ring Sideroblasts (RS) Who Require Red Blood Cell (RBC) Transfusions. 60th Annual Meeting of the American Society of Hematology (ASH), Dec. 1-4, San Diego, California, Oral Presentation (2018) (18 paqes).
Fields et al., Activin receptor antagonists for cancer-related anemia and bone disease. Expert Opin Investig Drugs. Jan. 2013;22(1):87-101. doi: 10.1517/13543784.2013.738666. Epub Nov. 6, 2012.
Galie et al., 2015 ESC/ERS Guidelines for the diagnosis and treatment of pulmonary hypertension: The Joint Task Force for the Diagnosis and Treatment of Pulmonary Hypertension of the European Society of Cardiology (ESC) and the European Respiratory Society (ERS): Endorsed by: Association for European Paediatric and Congenital Cardiology (AEPC), International Society for Heart and Lung Transplantation (ISHLT). Eur Heart J. Jan. 1, 2016;37(1):67-119. doi: 10.1093/eurheartj/ehv317. Epub Aug. 20, 2015.
Garcia-Manero et al., Hematologic Improvement-Neutrophil and -Platelet in the MEDALIST Trial: Multilineage Data from a Phase 3, Randomized, Double-Blind, Placebo-Controlled Study of Luspatercept to Treat Anemia in Patients with Very Low-, Low-, or Intermediate-Risk Myelodysplastic Syndromes with Ring Sideroblasts Who Require Red Blood Cell (RBC) Transfusions. 61st Annual Meeting of the American Society of Hematology (ASH), Dec. 7-10, Orlando, Florida, Abstract 4243 (2019) (1 page).
Gerds et al., A Phase 2 Study of Luspatercept in Patients With Myelofibrosis-Associated Anemia, 61st Annual Meeting of the American Society of Hematology (ASH), Dec. 7-10. Orlando FL, Presentation, Abstract 557, retrieved from <acceleronpharma.com/wpcontent/uploads/2019/12/Gerds-et-al.-Luspatercept-in-MF_ASH-2019-7-Dec-2019-FINAL-FOR-UPLOAD.pdf>, (2019) (13 pages).
Giagounidis et al., Luspatercept Increases Hemoglobin and Reduces Transfusion Burden in Patients With Lower-Risk Myelodysplastic Syndromes (MOS): Long-Term Results From the Phase 2 PACE-MOS Study. 22nd European Hematology Association Congress, Jun. 22-25, Madrid, Spain, Abstract P666, retrieved from <acceleronpharma.com/wp-content/uploads/2017/06/EHA-2017-MDS-Poster-20Jun2017-FINAL.pdf>, (Jun. 2017) (1 page).
Giagounidis et al., Luspatercept Treatment Leads to Long Term Increases in Hemoglobin and Reductions in Transfusion Burden in Patients with Low or Intermediate-1 Risk Myelodysplastic Syndromes (MOS): Preliminary Results from the Phase 2 PACE-MOS Extension Study. Presentation. (2015) (16 pages).
Goh et al., Activin receptor type 2A (ACVR2A) functions directly in osteoblasts as a negative regulator of bone mass. J Biol Chem. Aug. 18, 2017;292(33):13809-13822. doi: 10.1074/jbc.M117. 782128. Epub Jun. 28, 2017.
Graham et al., A Soluble Activin Receptor IIB Fails to Prevent Muscle Atrophy in a Mouse Model of Spinal Cord Injury. J Neurotrauma. Jun. 15, 2016;33(12):1128-35. doi: 10.1089/neu.2015. 4058. Epub Feb. 11, 2016.
Guo et al., Myostatin inhibition in muscle, but not adipose tissue, decreases fat mass and improves insulin sensitivity. PLoS One. 2009;4(3):e4937. doi: 10.1371/journal.pone.0004937. Epub Mar. 19, 2009.

(56) References Cited

OTHER PUBLICATIONS

Guo et al., Myostatin inhibition prevents diabetes and hyperphagia in a mouse model of lipodystrophy. Diabetes. Oct. 2012;61(10):2414-23. doi: 10.2337/db11-0915. Epub May 17, 2012.

Hardy et al., The activin A antagonist follistatin inhibits cystic fibrosis-like lung inflammation and pathology. Immunol Cell Biol. Jul. 2015;93(6):567-74. doi: 10.1038/icb.2015.7. Epub Mar. 10, 2015.

Havill et al., Sotatercept Improves Anemia, Vascular Calcification, and Bone Loss in Patients With End-Stage Kidney Disease on Hemodialysis. American Society of Nephrology Kidney Week 2015, Nov. 5-8, San Diego, CA, Poster TH-P0038, retrieved from <acceleronpharma.com/wp-content/uploads/2017/03/20151105-ASN-2015_Sotatercept-REN-OO1-Poster 10.20.15-Final-1.pdf>, (2015).

Highland et al., Development of the Pulmonary Hypertension Functional Classification Self-FC Report: a patient version adapted from the World Health Organization Functional Classification Measure. Health Qual Life Outcomes. Aug. 24, 2021;19(1):202. doi: 10.1186/s12955-021-01782-0.

Hoffmann et al., Compartment-specific expression of collagens and their processing enzymes in FD intrapulmonary arteries of IPAH patients. Am J Physiol Lung Cell Mol Physiol. May 15, 2015;308(10):L1002-13. doi: 10.1152/ajplung.00383.2014. Epub Apr. 3, 2015.

Huertas et al., Immune Dysregulation and Endothelial Dysfunction in Pulmonary Arterial Hypertension: a complex interplay. Circulation. Mar. 25, 2014;129(12):1332-40. doi: 10.1161/CIRCULATIONAHA.113.004555.

Human ActRII extracellular region chimera, SEQ ID 174., retrieved from EBI accession No. GSP:BKX55865, dated May 19, 2022.

Humeniuk et al., Brief report: Loss of p15Ink4b accelerates development of myeloid neoplasms in Nup98-HoxD13 transgenic mice. Stem Cells. May 2014;32(5):1361-6. doi: 10.1002/stem.1635.

Hybrid human mutant activin IIB receptor hu-ActRIIB-ECD, SEQ ID 114., retrieved from EBI accession No. GSP:BDH87204, dated Dec. 15, 2016.

Jiang et al., Activin A as a Novel Chemokine Induces Migration of L929 Fibroblasts by ERK Signaling in Microfluidic Devices. Front Cell Dev Biol. May 21, 2021;9:660316. doi: 10.3389/fcell.2021.660316. eCollection 2021.

Joshi et al., ActRIIA-Fc (Sotatercept) Reverses Pulmonary Vascular Remodeling to Attenuate Pulmonary Arterial Hypertension by Rebalancing Activin/BMP Signaling in a Preclinical Model. American Thoracic Society 2019 International Conference, May 17-22, Dallas, TX, Poster, retrieved from <acceleronpharma.com/wp-content/uploads/2O19/O6/Joshi-SR-et-al-ATS-2O19-Poster-Sotatercept-Reverses-Pulmonary-Vascular-R . . . —1.pdf>, (2019).

Joshi et al., RAP-O11, a Murine Ortholog of ACTRIIA-FC (Sotatercept), Improves Pulmonary Hemodynamics and Restores Right Ventricular Structure and Function in a Preclinical Model of Severe Angio-obliterative Pulmonary Arterial Hypertension. American Heart Association Scientific Session, Nov. 10-12, Chicago, Illinois, retrieved from <http://acceleronpharma.com/wpcontent/uploads/2018/11/SRJ-AHA-2018-Poster.pdf>.

Komrokji et al., A Phase 2, Dose-Finding Study of Sotatercept (ACE-O11) in Patients with Lower-Risk Myelodysplastic Syndromes or Non-Proliferative Chronic Myelomonocytic Leukemia and Anemia Requiring Transfusion. The 13th International Symposium on Myelodysplastic Syndromes, Apr. 29-May 2, Washington, D.C., retrieved from <http://acceleronpharma.com/wpcontent/uploads/2017/03/20150429-Komrokji-MDS-001_MDSF-2015-presentation_29-April-2015_FINAL.pdf>, (2015) (21 pages).

Komrokji et al., An Open-Label, Phase 2, Dose-Finding Study of Sotatercept (ACE-011) in Patients with Low or Intermediate (Int)-1-Risk Myelodysplastic Syndromes (MOS) or Non-Proliferative Chronic Myelomonocytic Leukemia (CMML) and Anemia Requiring Transfusion. 56th Annual Meeting of the American Society of Hematology (ASH), Dec.r 6-9, San Francisco, California. Poster P3251 (2014) (1 page).

Kuo et al., MB109 as bioactive human bone morphogenetic protein-9 refolded and purified from E. coli inclusion bodies. Microb Cell Fact. Feb. 24, 2014;13(1):29. doi: 10.1186/1475-2859-13-29.

Langdon et al., RAP-011, an activin receptor ligand trap, increases hemoglobin concentration in hepcidin transgenic mice. Am J Hematol. Jan. 2015;90(1):8-14. doi: 10.1002/ajh.23856. Epub Oct. 25, 2014.

Lee et al., Growth differentiation factor 11 signaling controls retinoic acid activity for axial vertebral development. Dev Biol. Nov. 1, 2010;347(1):195-203. doi: 10.1016/j.ydbio.2010.08.022. Epub Aug. 27, 2010.

Lee et al., Myostatin and the control of skeletal muscle mass. Curr Opin Genet Dev. Oct. 1999;9(5):604-7. doi: 10.1016/s0959-437x(99)00004-0.

Lee et al., Regulation of muscle growth by multiple ligands signaling through activin type II receptors. Proc Natl Acad Sci U S A. Dec. 13, 2005;102(50):18117-22. doi: 10.1073/pnas.0505996102. Epub Dec. 5, 2005.

Lee et al., Regulation of myostatin activity and muscle growth. Proc Natl Acad Sci U S A. Jul. 31, 2001;98(16):9306-11. doi: 10.1073/pnas.151270098. Epub Jul. 17, 2001.

Lee et al., Role of satellite cells versus myofibers in muscle hypertrophy induced by inhibition of the myostatin/activin signaling pathway. Proc Natl Acad Sci U S A. Aug. 28, 2012;109(35):E2353-60. doi: 10.1073/pnas.1206410109. Epub Aug. 6, 2012.

Lema et al., Abstract P.127-KER-050, a novel muscle anabolic, functions as a ligand trap that binds myo-catabolic TGFβ ligands and has reduced binding affinity for BMP9, a critical vascular remodeling ligand. Neuromuscular Disorders. Oct. 2019;29(S85):1. DOI: 10.1016/j.nmd.2019.06.183.

Lotinun et al., A soluble activin receptor Type IIA fusion protein (ACE-011) increases bone mass via a dual anabolic-antiresorptive effect in Cynomolgus monkeys. Bone. Apr. 2010;46(4):1082-8. doi: 10.1016/j.bone.2010.01.370. Epub Jan. 18, 2010.

Macdonald et al., "Denervation atrophy is independent from Akt and mTOR activation and is not rescued by myostatin inhibition," first posted online on Feb. 6, 2014, published in final edited form as: Dis Model Mech. 7(4):471-81 (2014) (Author manuscript) (39 pages).

Malluche et al., Sotatercept: Initial Signal-Seeking Quantitative Computed Tomography Results for Bone Mass and Vascular Calcification in Hemodialysis Subjects Treated With Escalating Doses: Interim Analysis of ACE-011-REN-001. American Society of Nephrology Kidney Week 2014, Nov. 11-16, Philadelphia, PA, retrieved from <http://acceleronpharma.com/wpcontent/uploads/2017/03/20141113-Malluche_ASN-2014_Sotatercept-Bone-Mass-VC-Poster_11-10-14-Final.pdf>, (2014).

Malluche et al., The Role of Activin Signaling in the Pathogenesis of Renal Osteodystrophy of CKD-MBD. 52nd ERA-EDTA Congress, May 28-31, London, United Kingdom, Poster FP406, retrieved from <acceleronpharma.com/wp-content/uploads/2017/03/20150529-ERA-2015_RAP011-Bone-Histomorohometrv-Poster_05.22.15-Final-for-QR-Code.Pdf>, (2015).

Marisavljevic et al., Myelofibrosis in primary myelodysplastic syndromes: clinical and biological significance. Med Oneal. 21 (4):325-31 (2004) (Abstract only) (2 pages).

Martinez, Luspatercept Inhibits pSmad2/3 Signaling and Promotes Erythroid Maturation Through a GATA 1 Dependent Mechanism. 23rd European Hematology Association Congress, Jun. 14-17, Stockholm, Sweden, Oral Presentation, retrieved from <acceleronpharma.com/wpcontent/uploads/2018/06/EHA2018PMFinal.pdf>, (2018).

Martinez, RAP-536 (Murine ACE-536/Luspatercept) Inhibits Smad2/3 Signaling and Promotes Erythroid Differentiation By Restoring GATA 1 Function in Murine Beta-thalassemia. 21st European Hematology Association Congress, Jun. 9-12, Copenhagen, Denmark, Oral Presentation, retrieved from <acceleronpharma.com/wp-content/uploads/2017/03/20160610PedroEHA2016Final.pdf> (Jun. 2016) (23 pages).

Martinez, RAP-536 (Murine ACE-536/Luspatercept) Inhibits Smad2/3 Signaling and Promotes Erythroid Differentiation By Restoring GATA 1 Function in Murine Beta-thalassemia. Oral Presentation. Blood. 2015; 126(23):751.

(56)                    References Cited

OTHER PUBLICATIONS

Mcpherron et al., Double muscling in cattle due to mutations in the myostatin gene. Proc Natl Acad Sci U S A. Nov. 11, 1997;94(23):12457-61. doi: 10.1073/pnas.94.23.12457.

Mcpherron et al., GDF-3 and GDF-9: two new members of the transforming growth factor-beta superfamily containing a novel pattern of cysteines. J Biol Chem. Feb. 15, 1993;268(5):3444-9.

Mcpherron et al., Redundancy of myostatin and growth/differentiation factor 11 function. BMC Dev Biol. Mar. 19, 2009;9:24. doi: 10.1186/1471-213X-9-24.

Mcpherron et al., Regulation of anterior/posterior patterning of the axial skeleton by growth/differentiation factor 11. Nat Genet. Jul. 1999;22(3):260-4. doi: 10.1038/10320.

Mcpherron et al., Soluble activin receptor type IIB treatment does not cause fat loss in mice with diet-induced obesity. Diabetes Obes Metab. Mar. 2012;14(3):279-82. doi: 10.1111/j.1463-1326.2011. 01520.x. Epub Nov. 21, 2011.

Mcpherron et al., Suppression of body fat accumulation in myostatin-deficient mice. J Clin Invest. Mar. 2002;109(5):595-601. doi: 10.1172/JCI13562.

Mcpherron et al., The transforming growth factor beta superfamily. Growth Factors and Cytokines in Health and Disease. 1996; 1 :357-39.

Mesa et al., A Phase 2, Multicenter, Open-Label Study of the Safety and Efficacy of Luspatercept in Subjects With Myeloproliferative Neoplasm (MPN)-Associated Myelofibrosis and Anemia With or Without RBC Transfusion Dependence. American Society of Clinical Oncology (ASCO) Annual Meeting, Jun. 1-5, Chicago Illinois, Poster TPS7083, retrieved from <http:// acceleronpharma.com/wp-content/uploads/2018/06/Mesa-MF-TiP-ASCO-2018-Poster-May-24-2018 FINAL-1.pdf>, (2018) (1 page).

Morgenroth et al., Insights into bone health in Duchenne muscular dystrophy. Bonekey Rep. Feb. 1, 2012;1:9. doi: 10.1038/bonekey. 2012.5. eCollection 2012.

Morine et al., Activin IIB receptor blockade attenuates dystrophic pathology in a mouse model of Duchenne muscular dystrophy. Muscle Nerve. Nov. 2010;42(5):722-30. doi: 10.1002/mus.21743.

Morrell et al., Targeting BMP signaling in cardiovascular disease and anaemia. Nat Rev Cardiol. Feb. 2016;13(2):106-20. doi: 10.1038/nrcardio.2015.156. Epub Oct. 13, 2015.

Mulivor et al., RAP-011, a Soluble Activin Receptor Type IIa Murine IgG-Fc Fusion Protein, Prevents Chemotherapy Induced Anemia. Blood. 114(22):161 (Nov. 2009).

Nagy et al., Electrical impedance myography as a biomarker of myostatin inhibition with ActRIIB-mFc: a study in wild-type mice. Future Sci OA. Apr. 16, 2018;4(6):FSO308. doi: 10.4155/fsoa-2018-0002. eCollection Jul. 2018.

Ngo et al., Computational Complexity, Protein Structure Prediction, and the Levinthal Paradox. The Protein Folding Problem and Tertiary Structure Prediction. Birkhauser Boston, pp. 433, 492-495 (1994).

Nielsen et al., Postnatal Hyperplasic Effects of ActRIIB Blockade in a Severely Dystrophic Muscle. J Cell Physiol. Jul. 2017;232(7):1774-1793. doi: 10.1002/jcp.25694. Epub Feb. 16, 2017.

No Author Listed Study to Evaluate the Effects of ACE-536 in Patients With Beta-thalassemia, U.S. National Library of Medicine, <Clinicaltrials.gov/ct2/show/NCTO174954O?term=luspatercept &draw=2&rank=11 >, first posted Dec. 13, 2012, retrieved Mar. 30, 2020.

No Author Listed To Determine Safe and Effective Dose of ACE-O11 for the Treatment of Chemotherapy Induced Anemia in Patients With Advanced Non-small Cell Lung Cancer, U.S. National Library of Medicine, <clinicaltrials.gov/ct2/show/NCTO1284348?term= sotatercept&draw=2&rank=6>, first posted Jan. 27, 2011, retrieved Mar. 30, 2020.

No Author Listed To Document the Burden of Illness on the Quality of Life and the Impact on Healthcare Utilization in (Beta)-thalassemia Subjects Who Are Transfusion Dependent (TD) and Non-transfusion Dependent (NTD) Receiving Standard of Care. U.S. National Library of Medicine, <Clinicaltrials.gov/ct2/show/

NCTO2626689?term=luspatercept&draw=2&rank= 14>, first posted Dec. 10, 2015, retrieved Mar. 30, 2020.

No Author Listed, A Phase 2 Study of Intravenous or Subcutaneous Dosing of Sotatercept (ACE-O11) in Patients With End-Stage Kidney Disease on Hemodialysis. U.S. National Library of Medicine, <Clinicaltrials.gov/ct2/show/NCTO1999582?term=sotatercept &draw=2&rank=9>, first posted Dec. 3, 2013, retrieved on Mar. 30, 2020.

No Author Listed, A Phase IIa Study of Sotatercept on Bone Mass and Turnover in Patients With Multiple Myeloma. U.S. National Library of Medicine, <Clinicaltrials.gov/ct2/show/NCTO2230917? term=sotatercept&draw=2&rank=4>, first posted Sep. 3, 2014, retrieved Mar. 30, 2020.

No Author Listed, A Study of Sotatercept for the Treatment of Pulmonary Arterial Hypertension (PAH) (PULSAR). U.S. National Library of Medicine, <Clinicaltrials.gov/ct2/show/NCTO3496207? term=sotatercept&draw=2&rank=3>, first posted Apr. 12, 2018, retrieved Mar. 30, 2020.

No Author Listed, A Study of Sotatercept for the Treatment of Pulmonary Arterial Hypertension (SPECTRA). U.S. National Library of Medicine, <Clinicaltrials.gov/ct2/show/NCTO3738150?term= sotatercept&draw=2&rank= 1 >, first posted Nov. 13, 2018, retrieved on Mar. 30, 2020.

No Author Listed, Efficacy and Safety Study of Luspatercept (ACE-536) Versus Epoetin Alfa for the Treatment of Anemia Due to IPSS-R Very Low, Low or Intermediate Risk Myelodysplastic Syndromes (MOS) in ESA Naive Subjects Who Require Red Blood Cell Transfusions (COMMANDS). U.S. National Library of Medicine, <Clinicaltrials.gov/ct2/show/NCTO3682536?term=luspatercept &draw=2&rank=1O>, first posted Sep. 24, 2018, retrieved Mar. 30, 2020.

No Author Listed, Keros Therapeutics Presents Results from Preclinical Studies Investigating KER-012 at the American Society for Bone and Mineral Research 2020 Annual Meeting. Keros Therapeutics, < https ://www.globe newswire. co m/news-release/2020/ 09/11/2092586/0/en/Keros-Therapeutics-Presents-Results-from-Preclinical-Studies-Investigating-KER-O12-at-the-American-Society-for-Bone-and-Mineral-Research-2O2O-Annual-Meeting.html>, dated Sep. 11, 2020, retrieved on Feb. 25, 2021.

No Author Listed, Safety and Efficacy Study of Sotatercept in Adults With Transfusion Dependent Diamond Blackfan Anemia (ACE-O11-DBA). U.S. National Library of Medicine, <Clinicaltrials. gov/ct2/show/NCTO1464164?term=sotatercept&draw=2&rank= 2>, first posted Nov. 3, 2011, retrieved Mar. 30, 2020.

No Author Listed, Sotatercept in Treating Patients With Myeloproliferative Neoplasm-Associated Myelofibrosis or Anemia. U.S. National Library of Medicine, <Clinicaltrials.gov/ct2/show/NCTO1712308? term=sotatercept&draw=2&rank=8>, first posted Oct. 23, 2012, retrieved Mar. 30, 2020.

No Author Listed, Study of ACE-536 for the Treatment of Anemia in Patients With Myelodysplastic Syndromes (MOS). U.S. National Library of Medicine, <Clinicaltrials.gov/ct2/show/NCTO17 49514 ?term=luspatercept&draw=2&rank= 12>, first posted Dec. 13, 2012, retrieved Mar. 30, 2020.

No Author Listed, Study of ACE-536 in Healthy Postmenopausal Women. U.S. National Library of Medicine, <Clinicaltrials.gov/ct2/ show/NCTO1432717?term=luspatercept&draw=2&rank=13>, first posted Sep. 13, 2011, retrieved Mar. 30, 2020.

No Author Listed, Study of Sotatercept for the Treatment of Anemia in low-or Intermediate-1 Risk Myelodysplastic Syndromes (MOS) or Non-proliferative Chronic Myelomonocytic Leukemia (CMML). U.S. National Library of Medicine, <Clinicaltrials.gov/ct2/show/ NCTO1736683?term=sotatercept&draw=2&rank=5>, first posted Nov. 29, 2012, retrieved Mar. 30, 2020.

No Author Listed, Study to Evaluate Effect of a Single Dose of Sotatercept (ACE-O11) on Red Blood Cell Mass and Plasma Volume in Subjects With Solid Tumors. U.S. National Library of Medicine, <Clinicaltrials.gov/ct2/show/NCTO 1190644 ?term= sotatercept&draw=2&rank= 7>, first posted Aug. 27, 2010, retrieved Mar. 30, 2020.

(56)                References Cited

OTHER PUBLICATIONS

Ogawa et al., Long-term patient survival with idiopathic/heritable pulmonary arterial hypertension treated at a single center in Japan. Life Sci. Nov. 24, 2014;118(2):414-9. doi: 10.1016/j.lfs.2014.01. 077. Epub Feb. 11, 2014.

Paddock et al., Steps toward therapeutically targeting the activin type II receptor for treating heart failure. Am J Physiol Heart Circ Physiol. Feb. 1, 2020;318(2):H326-H328. doi: 10.1152/ajpheart. 00004.2020. Epub Jan. 10, 2020.

Park et al., The prognostic value of serum erythropoietin in patients with lower-risk myelodysplastic syndromes: a review of the literature and expert opinion. Ann Hematol. Jan. 2020;99(1):7-19. doi: 10.1007/s00277-019-03799-4. Epub Oct. 25, 2019.

Paulson, Targeting a new regulator of erythropoiesis to alleviate anemia. Nat Med. Apr. 2014;20(4):334-5. doi: 10.1038/nm.3524.

Pearsall et al., A soluble activin type IIA receptor induces bone formation and improves skeletal integrity. Proc Natl Acad Sci U S A. May 13, 2008;105(19):7082-7. doi: 10.1073/pnas.0711263105. Epub May 6, 2008.

Piga et al., Improvements in Hemoglobin, Quality of Life, and Six-Minute-Walk Distance in Adults with beta-Thalassemia Treated with Luspatercept: Long-Term Phase 2 Study. 23rd European Hematology Association Congress, Jun. 14-17, Stockholm, Sweden, Oral Presentation, retrieved from <acceleronpharma.com/wp-content/ uploads/2018/06/Piga-et-al-EHA-2018-PresentationImprovements-in-Hemoglobin-Quality-of-Life-and-Six-Minute-Walk-Distance. pdf>, (2018) (22 pages).

Piga et al., Luspatercept (ACE-536) Increases Hemoglobin and Decreases Transfusion Burden and Liver Iron Concentration in Adults with Beta-Thalassemia: Preliminary Results from a Phase 2 Study. EHA (2015) (22 paqes).

Piga et al., Luspatercept (ACE-536) Increases Hemoglobin and Decreases Transfusion Burden and Serum Ferritin in Adults with Beta-Thalassemia: Preliminary Results from a Phase 2 Study. American Society of Hematology, Oral Presentation, dated Dec. 7, 2014.

Piga et al., Luspatercept Decreases Transfusion Burden and Liver Iron Concentration in Regularly Transfused Adults with Beta-Thalassemia. 21st European Hematology Association Congress, Jun. 9-12, Copenhagen, Denmark, Presentation, retrieved from <acceleronpharma.com/wp-content/uploads/2017/03/20160612-EHA-2016-Luspatercept-Thal-TD-FINAL.pdf>, (Jun. 2016) (15 pages).

Piga et al., Luspatercept improves hemoglobin levels and blood transfusion requirements in a study of patients with β-thalassemia. Blood. Mar. 21, 2019;133(12):1279-1289. doi: 10.1182/blood-2018-10-879247. Epub Jan. 7, 2019.

Piga et al., Luspatercept Increases Hemoglobin, Decreases Transfusion Burden, and Improves Patient-Reported Outcomes in Adults with Beta-Thalassemia. 58th Annual Meeting of the American Society of Hematology (ASH), Dec. 3-6, San Diego, California, Oral Presentation, retrieved from <http://acceleronpharma.com/wp-contentluploads/2017/03/20161205-LuspaterceptIncreases-Hemoalobin. pdf>, (Dec. 2016).

Piga et al., Luspatercept Increases Hemoglobin, Reduces Liver Iron Concentration and Improves Quality of Life in Non-Transfusion Dependent Adults with Beta-Thalassemia. 21st European Hematology Association Congress, Jun. 9-12, Copenhagen, Denmark, Abstract P758, retrieved from <http://acceleronpharma.com/wp-contentluploads/ 2017/03/20160611-EHA-2016-Luspatercept-BThal-NTD-poster-FINAL.pdf>, (Jun. 2016).

Piga et al., Luspatercept Increases Hemoglobin, Reduces Liver Iron Concentration and Improves Quality of Life in Non-Transfusion Dependent Adults with Beta-Thalassemia. 2nd MEGMA Conference, Nov. 11-12, Amman, Jordan, retrieved from <http:// acceleronpharma.com/wpcontentluploads/2017/03/20161111-TIF-2016-Luspatercept-BThal-NTD-poster_FINAL_16-10-31.pdf>, (Nov. 2016).

Platzbecker et al., Biomarkers of Ineffective Erythropoiesis Predict Response to Luspatercept in Patients with Low or Intermediate-1 Risk Myelodysplastic Syndromes (MOS): Final Results from the Phase 2 PACE-MOS Study. 57th American Society of Hematology Annual Meeting and Exposition, Dec. 5-8, Orlando, FL, Abstract 2862, retrieved from <Biomarkers of Ineffective Erythropoiesis Predict Response to Luspatercept in Patients with Low or Intermediate-1 Risk Myelodysplastic Syndromes (MOS): Final Results from the Phase 2 PACE-MOS Study>, (2015).

Platzbecker et al., Erythropoietic cellular analyses in luspatercept-treated lower-risk myelodysplastic syndromes (MOS): Phase 2 PACE-MOS study. 2018 American Society of Clinical Oncology (ASCO) Annual Meeting, Jun. 1-5, Chicago, Illinois, Abstract 7018, retrieved from <http://acceleronpharma.com/wp-content/uploads/ 2018/06/Platzbecker-ASCO-2018-Poster-Erythropoietic-Cellular-Analyses-Ph-2-PACE-MDS-Study-1.pdf>, (2018) (1 page).

Platzbecker et al., Luspatercept for the treatment of anaemia in patients with lower-risk myelodysplastic syndromes (PACE-MDS): a multicentre, open-label phase 2 dose-finding study with long-term extension study. Lancet Oncol. Oct. 2017;18(10):1338-1347. doi: 10.1016/S1470-2045(17)30615-0. Epub Sep. 1, 2017.

Platzbecker et al., Luspatercept Increases Hemoglobin and Reduces Transfusion Burden in Patients with Low-Intermediate Risk Myelodysplastic Syndromes (MOS): Long-Term Results From Phase 2 PACE-MOS Study. 21st European Hematology Association Congress, Jun. 9-12, Copenhagen, Denmark, Presentation, retrieved from <http://acceleronpharma.com/wpcontent/uploads/2017/03/ 20160610-EHA-2016-Luspatercept-MDS-FINAL.pdf> (Jun. 2016) (16 pages).

Platzbecker et al., Luspatercept Increases Hemoglobin And Reduces Transfusion Burden In Patients With Low Or Intermediate-1 Risk Myelodysplastic Syndromes (MOS): Preliminary Results From A Phase 2 Study. EHA MOS Oral Presentation, Jun. 13, 2015 (16 pages).

Platzbecker et al., Luspatercept Increases Hemoglobin And Reduces Transfusion Burden In Patients With Low Or Intermediate-1 Risk Myelodysplastic Syndromes (MOS): Preliminary Results From A Phase 2 Study. Advancing Research & Patient Care, The 13th International Symposium on Myelodyplastic Syndromes, Washington, D.C., Apr. 19-May 2, 2015.

Platzbecker et al., Luspatercept Response in New Subpopulations of Patients With Lower-Risk Myelodysplastic Syndromes (MOS): Update of the PACE Study. 14th International Symposium on Myelodysplastic Syndromes, May 3-6, Valencia, Spain, Oral Presentation, retrieved from<acceleronpharma.com/wp-content/uploads/ 2017/05/Platzbecker-U-MDS-Symposium-2017-Slides-Luspatercept-Response-in-New-Subpopulations-Website-Version.pdf>, (May 2017).

Platzbecker et al., Luspatercept Significantly Reduces Red Blood Cell (RBC) Transfusion Burden, Regardless of Gene Mutation Frequency, Spectrum, and Prognostic Significance, Among Patients with Lower-Risk Myelodysplastic Syndromes Enrolled in the MEDALIST Trial. retrieved from <http://acceleronpharma.com/wp-content/uploads/2019/12/ ASH-2O19-Platzbecker-MEDALI STMutational-analysis.pdf>, (2019).

Platzbecker et al., Mutational and Subgroup Analyses of Lower-Risk Myelodysplastic Syndromes (MOS) Patients Treated With Luspatercept: Phase 2 PACE-MOS Study. 23rd European Hematology Association Congress, Jun. 14-17, Stockholm, Sweden, Abstract PF498, retrieved from <http://acceleronpharma.com/wp-content/uploads/2018/06/EHA-2018-MDS-Poster-06June2018. pdf>, (2018) (1 page).

Platzbecker et al., Mutational Profile and Analysis of Lower-Risk Myelodysplastic Syndromes (MOS) Patients Treated with Luspatercept: Phase 2 PACE-MOS Study. American Society of Hematology (ASH) 59th Annual Meeting & Exposition, Dec. 9-12, Atlanta, GA, Abstract 2982, retrieved from <acceleronpharma.com/wp-content/ uploads/2017/12/Platzbecker-U-ASH-2017-MDS-Lusoaterceot-Poster-Final.odf> (Dec. 2017) (1 page).

Porter et al., Effects of Luspatercept on Iron Overload and Impact on Responders to Luspatercept: Results from the BELIEVE Trial. 61st Annual Meeting of the American Society of Hematology (ASH), Abstract 2245, Blood. 134(Supplement 1):2245 (Dec. 2019.

Rabinovitch et al., Inflammation and Immunity in the Pathogenesis of Pulmonary Arterial Hypertension.Circ Res. Jun. 20, 2014;115(1):165-75. doi: 10.1161/CIRCRESAHA.113.301141.

(56)          References Cited

OTHER PUBLICATIONS

Raftopoulos et al., Sotatercept (ACE-011) for the treatment of chemotherapy-induced anemia in patients with metastatic breast cancer or advanced or metastatic solid tumors treated with platinum-based chemotherapeutic regimens: results from two phase 2 studies. Support Care Cancer. Apr. 2016;24(4):1517-25. doi: 10.1007/s00520-015-2929-9. Epub Sep. 14, 2015.
Ralston et al., Management of Osteogenesis imperfecta. Front Endocrinol (Lausanne). Feb. 11, 2020:10:924. doi: 10.3389/fendo. 2019.00924. eCollection 2019.
Rodgarkia-Dara et al., The activin axis in liver biology and disease. Mutat Res. Nov.-Dec. 2006;613(2-3):123-37. doi: 10.1016/j.mrrev. 2006.07.002. Epub Sep. 25, 2006.
Roh et al., Activin type II receptor signaling in cardiac aging and heart failure. Sci Transl Med. Mar. 6, 2019;11(482):eaau8680. doi: 10.1126/scitranslmed.aau8680.
Ruckle et al., Single-dose, randomized, double-blind, placebo-controlled study of ACE-011 (ActRIIA-IgG1) in postmenopausal women. J Bone Miner Res. Apr. 2009;24(4):744-52. doi: 10.1359/jbmr.081208.
Sako et al., Characterization of the ligand binding functionality of the extracellular domain of activin receptor type IIb. J Biol Chem. Jul. 2, 2010;285(27):21037-48. doi: 10.1074/jbc.M110.114959. Epub Apr. 12, 2010.
Sanchez et al., Evaluation of Electrical Impedance as a Biomarker of Myostatin Inhibition in Wild Type and Muscular Dystrophy Mice. PLoS One. Oct. 20, 2015;10(10):e0140521. doi: 10.1371/journal.pone.0140521. eCollection 2015.
Sherman et al., Multiple-dose, safety, pharmacokinetic, and pharmacodynamic study of sotatercept (ActRIIA-IgG1), a novel erythropoietic agent, in healthy postmenopausal women. J Clin Pharmacol. Nov. 2013;53(11):1121-30. doi: 10.1002/jcph.160. Epub Sep. 9, 2013.
Smith et al., Long-term Effects of Sotatercept Compared With Placebo for Correction of Anemia in Hemodialysis Subjects: Interim Analysis of ACE-011-REN-01. 52nd ERA-EDT A Congress, May 28-31, London, UK, Poster FP661, retrieved from <http://acceleronpharma.com/wpcontent/uploads/2017/03/20150529-ERA-2015_Sotatercept-Hb-Safety-Poster_05.22.15-Final-for-QR-Code-1.pdf>, (2015).
Smith et al., Quantitative Computed Tomography Results for Bone Mass and Abdominal Aortic Vascular Calcification in Hemodialysis Subjects Treated With Escalating Dose Levels of Sotatercept: Interim Analysis of ACE-O11-REN-OO1. 52nd ERA-EDTA Congress, May 28-31, London, UK, Poster SP645, retrieved from <acceleronpharma.com/wpcontent/uploads/2017/03/20150530-ERA-2015_Sotatercept-QCT-Poster_05.22.15-Final-for-QRCode.pdf>, (2015).
Stegelmann et al., Updated Results from the German Mpnsg-O212 Combination Trial: Ruxolitinib Plus Pomalidomide in Myelofibrosis with Anemia. Blood. 134(Supplement_1):672 (5 pages) (2019).
Sunada, [Anti-myostatin antibody therapy for myopathies]. Rinsho Shinkeigaku. Nov. 2011;51(11):1157-9. doi: 10.5692/clinicalneurol. 51.1157.
Sunada, [Myostatin blockade therapy for muscular atrophy]. Brain Nerve. Nov. 2011;63(11):1271-7.
Suragani et al., Modified activin receptor IIB ligand trap mitigates ineffective erythropoiesis and disease complications in murine β-thalassemia. Blood. Jun. 19, 2014;123(25):3864-72. doi: 10.1182/blood-2013-06-511238. Epub May 2, 2014.
Suragani et al., Modified ActRIIB-Fc Fusion Protein (ACE-536) Decreases Irreversible Sickle Cells in a Murine Model of Sickle Cell Disease. EHA, Poster P535, retrieved from <acceleronpharma.com/wp-content/uploads/2017/03/20140614-ACE-536-20140613-Modified-ActR11B-Fc-Fusion-Protein-Decreases-irreversible-Sickle-Cells-in-a-Murine-Model-of-1.pdf>,(2014).
Suragani et al., Modified ActRIIB-mFc Fusion Protein (murine ortholog of Luspatercept) Mitigates Sickling and Red Cell Pathology in a Murine Model of Sickle Cell Disease. ASH 56th Annual Meeting, Dec. 6-9, San Francisco, California. Poster 4055 (2014).
Suragani et al., Transforming growth factor-β superfamily ligand trap ACE-536 corrects anemia by promoting late-stage erythropoiesis. Nat Med. Apr. 2014;20(4):408-14. doi: 10.1038/nm.3512. Epub Mar. 23, 2014.
Thevis et al., Emerging drugs affecting skeletal muscle function and mitochondrial biogenesis—Potential implications for sports drug testing programs. Rapid Commun Mass Spectrom. Mar. 15, 2016;30(5):635-51. doi: 10.1002/rcm.7470.
Tomillero et al., Gateways to clinical trials. Methods Find Exp Clin Pharmacol. Jan.-Feb. 2010;32(1):47-86.
Tournier et al., Calibrated automated thrombography demonstrates hypercoagulability in patients with idiopathic pulmonary arterial hypertension. Thromb Res. Dec. 2010;126(6):e418-22. doi: 10.1016/j.thromres.2010.08.020.
Townson et al., Specificity and structure of a high affinity activin receptor-like kinase 1 (ALK1) signaling complex. J Biol Chem. Aug. 10, 2012;287(33):27313-25. doi: 10.1074/jbc.M112.377960. Epub Jun. 20, 2012.
Vallet et al., Activin A promotes multiple myeloma-induced osteolysis and is a promising target for myeloma bone disease. Proc Natl Acad Sci U S A. Mar. 16, 2010;107(11):5124-9. doi: 10.1073/pnas. 0911929107. Epub Mar. 1, 2010.
Viprakasit et al., Evaluating Luspatercept Responders in the Phase 3, Randomized, Double-Blind, Placebo-Controlled BELIEVE Trial of Luspatercept in Adult beta-Thalassemia Patients Who Require Regular Red Blood Cell Transfusions. Blood. 134(Supplement 1):3545 (Dec. 2019).
Wagner et al., Loss of myostatin attenuates severity of muscular dystrophy in mdx mice. Ann Neurol. Dec. 2002;52(6):832-6. doi: 10.1002/ana.10385.
Wang et al., A soluble activin receptor Type IIB does not improve blood glucose in streptozotocin-treated Mice. Int J Biol Sci. Jan. 5, 2015;11(2):199-208. doi: 10.7150/ijbs.10430. eCollection 2015.
Wang et al., Myostatin inhibition induces muscle fibre hypertrophy prior to satellite cell activation. J Physiol. May 1, 2012;590(9):2151-65. doi: 10.1113/jphysiol.2011.226001. Epub Mar. 5, 2012.
Wells, Additivity of mutational effects in proteins. Biochemistry. Sep. 18, 1990;29(37):8509-17. doi: 10.1021/bi00489a001.
Wolfman et al., Activation of latent myostatin by the BMP-1/tolloid family of metalloproteinases. Proc Natl Acad Sci U S A. Dec. 23, 2003;100(26):15842-6. doi: 10.1073/pnas.2534946100. Epub Dec. 11, 2003.
Wu et al., Identification and analysis of type II TGF-β receptors in BMP-9-induced osteogenic differentiation of C3H10T1/2 mesenchymal stem cells. Acta Biochim Biophys Sin (Shanghai). Oct. 2010;42(10):699-708. doi: 10.1093/abbs/gmq075. Epub Aug. 27, 2010.
Yee et al., Phase 1 Dose-Escalation Study of Sotatercept (ACE-011) in Combination with Lenalidomide and Dexamethasone in Patients with Relapsed and/or Refractory Multiple Myeloma. Headache.1 :0 (2015).
Yndestad et al., Elevated levels of activin A in clinical and experimental pulmonary hypertension. J Appl Physiol (1985). Apr. 2009;106(4):1356-64. doi: 10.1152/japplphysiol.90719.2008. Epub Feb. 5, 2009.
Yu, Sotatercept for rebalancing BMP/TGF-beta/activin signaling in PAH. Scientific Sessions Presentation (Nov. 2018).
Yung et al., ACTRIIA-Fc rebalances BMP and activin/TGF-beta signaling to attenuate experimental pulmonary hypertension. American Heart Association Scientific Session, Nov. 11-15, Anaheim, CA, retrieved from <acceleronpharma.com/wp-content/uploads/2O17/11/Dr.-Yu-Presentation-AHA-17-1.pdf>.
Yung, ACTRIIA-Fc Rebalances Activin/GDF and BMP9 Signaling to Attenuate Experimental Pulmonary Hypertension. American Heart Association Scientific Session, Nov. 10-12, Chicago, Illinois, retrieved from <acceleronpharma.com/wp-content/uploads/2018/11 /Lai-Ming-AHA-2018-ActRlla-Fc-v2-final.odf>, (2018).
Zimmers et al., Induction of cachexia in mice by systemically administered myostatin. Science. May 24, 2002;296(5572):1486-8. doi: 10.1126/science.1069525.

FIG. 1

ActRII A/B Dose Response
Percent Body Weight Change

Vehicle
ACTRII A/B 20mpk
ACTRII A/B 8mpk
ACTRII A/B 3mpk
ACTRII A/B 1mpk

ACTRII Variants Dose Response
Gastrocnemius Weight

ACTRII Variants Dose Response
Pectoralis Weight

ACTIVIN RECEPTOR TYPE IIA VARIANTS AND METHODS OF USE THEREOF

RELATED APPLICATIONS

This application is a Continuation of U.S. application Ser. No. 18/219,336, filed Jul. 7, 2023 which is a Continuation of U.S. application Ser. No. 17/327,914, filed May 24, 2021, which is a Division of U.S. application Ser. No. 16/348,987, filed May 10, 2019, which is a national stage filing under 35 U.S.C. 371 of International Patent Application Serial No. PCT/US2017/060960, filed Nov. 9, 2017, which is a Non-Prov of Prov (35 USC 119 (e)) of U.S. Application Ser. No. 62/531,943, filed Jul. 13, 2017, Application PCT/US2017/060960 is a Non-Prov of Prov (35 USC 119 (e)) of U.S. Application Ser. No. 62/420,476, filed Nov. 10, 2016, The entire contents of these applications are incorporated herein by reference in their entirety.

REFERENCE TO AN ELECTRONIC SEQUENCE LISTING

The contents of the electronic sequence listing (T083370060US05-SEQ-ACZ.xml; Size: 188,738 bytes; and Date of Creation: Apr. 17, 2025) are herein incorporated by reference in its entirety.

BACKGROUND OF THE INVENTION

Duchenne muscular dystrophy (DMD), facioscapulohumeral muscular dystrophy (FSHD), inclusion body myositis (IBM), and amyotrophic lateral sclerosis (ALS) are examples of muscle diseases that involve weakness and atrophy of muscles and/or motor neurons that control voluntary muscle movements. DMD is caused by mutations in the X-linked dystrophin gene and characterized by progressive muscle degeneration and weakness in all skeletal muscles. FSHD particularly affects skeletal muscles of the face, shoulders, upper arms, and lower legs. IBM is an inflammatory muscle disease that mainly affects muscles of the thighs and muscles of the arms that control finger and wrist flexion. ALS is a motor neuron disease characterized by stiff muscles, muscle twitching, and muscle atrophy throughout the body due to the degeneration of the motor neurons. Efforts to improve treatment and survival of subjects having these devastating muscle diseases have not been successful.

Excess body weight is an increasing problem in the United States, with a prevalence of approximately 25% of the population. Increased visceral and subcutaneous fact causes dysfunction of various organs. Excessive body weight is a risk factor for an array of complications, including obesity, diabetes (e.g., Type-1 and Type-2 diabetes), cardiovascular disease, and several forms of cancer. Insulin resistance is also associated with obesity and occurs when pancreatic tissues require an elevated amount of insulin. Once pancreatic B cells can no longer produce sufficient insulin to meet the demand, hyperglycemia occurs and Type-2 diabetes develops. Adipocytes, which are increased in obesity, are believed to play a role in this process. Despite the prevalence of obesity and metabolic diseases such as diabetes (e.g., Type-1 and Type-2 diabetes) and insulin resistance, few therapeutic options are available.

There exists a need for novel treatments for these muscular and metabolic diseases.

SUMMARY OF THE INVENTION

The present invention features polypeptides that include an extracellular activin receptor type IIa (ActAIIa) variant.

In some embodiments, a polypeptide of the invention includes an extracellular ActRIIa variant fused to the N- or C-terminus of an Fc domain monomer or moiety. Such moieties may be attached by amino acid or other covalent bonds and may increase stability of the polypeptide. A polypeptide including an extracellular ActRIIa variant fused to an Fc domain monomer may also form a dimer (e.g., a homodimer or heterodimer) through the interaction between two Fc domain monomers. The polypeptides of the invention may be used to increase muscle mass and strength in a subject having a disease or condition involving weakness and atrophy of muscles, e.g., Duchenne muscular dystrophy (DMD), facioscapulohumeral muscular dystrophy (FSHD), inclusion body myositis (IBM), amyotrophic lateral sclerosis (ALS), sarcopenia, or cancer cachexia. The polypeptides of the invention may also be used to reduce body weight, reduce body fat, increase glucose clearance, increase insulin sensitivity, or reduce fasting insulin levels in a subject having or at risk of developing a metabolic disease, e.g., obesity, Type-1 diabetes, or Type-2 diabetes. Further, the polypeptides of the invention may also be used to affect myostatin, activin, and/or bone morphogenetic protein 9 (BMP9) signaling in a subject having a risk of developing or having a disease or condition involving weakness and atrophy of muscles or a metabolic disease.

In one aspect, the invention features a polypeptide including an extracellular activin receptor type IIa (ActRIIa) variant, the variant having a sequence of GAILGRSETQECLX$_1$X$_2$NANWX$_3$X$_4$X$_5$X$_6$TNQTGVEX$_7$ CX$_8$GX$_9$X$_{10}$X$_{11}$X$_{12}$X$_{13}$X$_{14}$HCX$_{15}$ATWX$_{16}$NISGSIEIV X$_{17}$X$_{18}$GCX$_{19}$X$_{20}$X$_{21}$DX$_{22}$NCYDRTDCVEX$_{23}$X$_{24}$X$_{25}$X$_{26}$ PX$_{27}$VYFCCCEGNMCNEKFSYFPEMEVTQPTS (SEQ ID NO: 1), wherein X$_1$ is F or Y; X$_2$ is F or Y; X$_3$ is E or A; X$_4$ is K or L; X$_5$ is D or E; X$_6$ is R or A; X$_7$ is P or R; X$_8$ is Y or E; X$_9$ is D or E; X$_{10}$ is K or Q; X$_{11}$ is D or A; X$_{12}$ is K or A; X$_{13}$ is R or A; X$_{14}$ is R or L; X$_{15}$ is F or Y; X$_{16}$ is K, R, or A; X$_{17}$ is K, A, Y, F, or I; X$_{18}$ is Q or K; X$_{19}$ is W or A; X$_{20}$ is L or A; X$_{21}$ is D, K, R, A, F, G, M, N, or I; X$_{22}$ is I, F, or A; X$_{23}$ is K or T; X$_{24}$ is K or E; X$_{25}$ is D or E; X$_{26}$ is S or N; and X$_{27}$ is E or Q, and wherein the variant has at least one amino acid substitution relative to a wild-type extracellular ActAIIa having the sequence of SEQ ID NO: 73 or an extracellular ActRIIa having any one of the sequences of SEQ ID NOs: 76-96.

In some embodiments, the variant has a sequence of GAILGRSETQECLFX$_2$NANWX$_3$X$_4$X$_5$X$_6$TNQTGVEX$_7$ CX$_8$GX$_9$KX$_{11}$X$_{12}$X$_{13}$X$_{14}$HCX$_{15}$ATWX$_{16}$NISGSIEIVX$_{17}$ X$_{18}$GCX$_{19}$X$_{20}$X$_{21}$DX$_{22}$NCYDRTDCVEX$_{23}$X$_{24}$X$_{25}$X$_{26}$ PX$_{27}$VYFCCCEGNMCNEKFSYFPEMEVTQPTS (SEQ ID NO: 2), wherein X$_2$, X$_3$, X$_4$, X$_5$, X$_6$, X$_7$, X$_8$, X$_9$, X$_{11}$, X$_{12}$, X$_{13}$, X$_{14}$, X$_{15}$, X$_{16}$, X$_{17}$, X$_{18}$, X$_{19}$, X$_{20}$, X$_{21}$, X$_{22}$, X$_{23}$, X$_{24}$, X$_{25}$, X$_{26}$, and X$_{27}$ are defined as above.

In some embodiments, the variant has a sequence of GAILGRSETQECLFX$_2$NANWEX$_4$X$_5$RTNQTGVEX$_7$CX$_8$ GX$_9$KDKRX$_{14}$HCX$_{15}$ATWX$_{16}$NISGSIEIVKX$_{18}$GCWL DDX$_{22}$NCYDRTDCVEX$_{23}$X$_{24}$X$_{25}$X$_{26}$PX$_{27}$VYFCCCEGN MCNEKFSYFPEMEVTQPTS (SEQ ID NO: 3), wherein X$_2$, X$_4$, X$_5$, X$_7$, X$_8$, X$_9$, X$_{14}$, X$_{15}$, X$_{16}$, X$_{18}$, X$_{22}$, X$_{23}$, X$_{24}$, X$_{25}$, X$_{26}$, and X$_{27}$ are defined as above.

In some embodiments, the variant has a sequence of GAILGRSETQECLFX$_2$NANWEX$_4$DRTNQTGVEX$_7$CX$_8$ GX$_9$KDKRX$_{14}$HCX$_{15}$ATWX$^{16}$NISGSIEIVKX$_{18}$GCWL DDX$_{22}$NCYDRTDCVEX$_{23}$KX$_{25}$X$_{26}$PX$_{27}$VYFCCCEGNM CNEKFSYFPEMEVTQPTS (SEQ ID NO: 4), wherein X$_2$, X$_4$, X$_7$, X$_8$, X$_9$, X$_{14}$, X$_{15}$, X$^{16}$, X$_{18}$, X$_{22}$, X$_{23}$, X$_{25}$, X$_{26}$, and X$_{27}$ are defined as above.

In some embodiments, the variant has a sequence of GAILGRSETQECLFX$_2$NANWEX$_4$DRTNQTGVEPCX$_8$ GX$_9$KDKRX$_{14}$HCFATWKNISGSIEIVKX$_{18}$GCWLDDI NCYDRTDCVEX$_{23}$KX$_{25}$X$_{26}$PX$_{27}$VYFCCCEGNMCNEK FSYFPEMEVTQPTS (SEQ ID NO: 5), wherein X$_2$, X$_4$, X$_8$, X$_9$, X$_{14}$, X$_{18}$, X$_{23}$, X$_{25}$, X$_{26}$, and X$_{27}$ are defined as above.

In any of the aforementioned embodiments, X$_1$ is F or Y. In any of the aforementioned embodiments, X$_2$ is F or Y. In any of the aforementioned embodiments, X$_3$ is E or A. In any of the aforementioned embodiments, X$_4$ is K or L. In any of the aforementioned embodiments, X$_5$ is D or E. In any of the aforementioned embodiments, X$_6$ is R or A. In any of the aforementioned embodiments, X$_7$ is P or R. In any of the aforementioned embodiments, X$_8$ is Y or E. In any of the aforementioned embodiments, X$_9$ is D or E. In any of the aforementioned embodiments, X$_{10}$ is K or Q. In any of the aforementioned embodiments, X$_{11}$ is D or A. In any of the aforementioned embodiments, X$_{12}$ is K or A. In any of the aforementioned embodiments, X$_{13}$ is R or A. In any of the aforementioned embodiments, X$_{14}$ is R or L. In any of the aforementioned embodiments, X$_{15}$ is F or Y. In any of the aforementioned embodiments, X$_{16}$ is K, R, or A. In any of the aforementioned embodiments, X$_{17}$ is K, A, Y, F, or I. In any of the aforementioned embodiments, X$_{18}$ is Q or K. In any of the aforementioned embodiments, X$_{19}$ is W or A. In any of the aforementioned embodiments, X$_{20}$ is L or A. In any of the aforementioned embodiments, X$_{21}$ is D, K, R, A, F, G, M, N, or I. In any of the aforementioned embodiments, X$_{22}$ is I, F, or A. In any of the aforementioned embodiments, X$_{23}$ is K or T. In any of the aforementioned embodiments, X$_{24}$ is K or E. In any of the aforementioned embodiments, X$_{25}$ is D or E. In any of the aforementioned embodiments, X$_{26}$ is S or N. In any of the aforementioned embodiments, X$_{27}$ is E or Q. In any of the aforementioned embodiments, X$_{23}$ is T, X$_{24}$ is E, X$_{25}$ is E, and X$_{26}$ is N. In any of the aforementioned embodiments, X$_{23}$ is T, X$_{24}$ is K, X$_{24}$ is E, and X$_{26}$ is N. In any of the aforementioned embodiments, X$_{17}$ is K.

In any of the aforementioned embodiments, the variant has the sequence of any one of SEQ ID NOs: 6-72.

In any of the aforementioned embodiments, the amino acid at position X$_{24}$ may be replaced with the amino acid K.

In any of the aforementioned embodiments, the amino acid at position X$_{24}$ may be replaced with the amino acid E.

In any of the aforementioned embodiments, a polypeptide described herein may further include a C-terminal extension of one or more amino acids (e.g., 1, 2, 3, 4, 5, 6, or more amino acids). In some embodiments, the C-terminal extension is amino acid sequence NP. In some embodiments, the C-terminal extension is amino acid sequence NPVTPK (SEQ ID NO: 155).

In any of the aforementioned embodiments, a polypeptide described herein may further include a moiety fused or covalently linked to the C-terminus of the polypeptide. In some embodiments, the moiety increases stability or improves the pharmacokinetics of the polypeptide. In some embodiments, the moiety is an Fc domain, an albumin-binding peptide, a fibronectin domain, or human serum albumin.

In any of the aforementioned embodiments, a polypeptide described herein may further include an Fc domain monomer fused to the C-terminus of the polypeptide by way of a linker. In some embodiments, the polypeptide that includes an extracellular ActRIIa variant described herein fused to an Fc domain monomer may form a dimer (e.g., a homodimer or heterodimer) through the interaction between two Fc domain monomers. In some embodiments, the Fc domain monomer has the sequence of SEQ ID NO: 97

In any of the aforementioned embodiments, a polypeptide described herein may further include an Fc domain fused to the C-terminus of the polypeptide by way of a linker. In some embodiments, the Fc domain is a wild-type Fc domain. In some embodiments, the wild-type Fc domain has the sequence of SEQ ID NO: 151. In some embodiments, the Fc domain contains one or more amino acid substitutions. In some embodiments, the Fc domain containing one or more amino acid substitutions does not form a dimer.

In any of the aforementioned embodiments, a polypeptide described herein may further include an albumin-binding peptide fused to the C-terminus of the polypeptide by way of a linker. In some embodiments, the albumin-binding peptide has the sequence of SEQ ID NO: 152.

In any of the aforementioned embodiments, a polypeptide described herein may further include a fibronectin domain fused to the C-terminus of the polypeptide by way of a linker. In some embodiments, the fibronectin domain peptide has the sequence of SEQ ID NO: 153.

In any of the aforementioned embodiments, a polypeptide described herein may further include a human serum albumin fused to the C-terminus of the polypeptide by way of a linker. In some embodiments, the human serum albumin has the sequence of SEQ ID NO: 154.

In some embodiments, the linker is an amino acid spacer. In some embodiments, the amino acid spacer is GGG, GGGA (SEQ ID NO: 98), GGGG (SEQ ID NO: 100), GGGAG (SEQ ID NO: 130), GGGAGG (SEQ ID NO: 131), or GGGAGGG (SEQ ID NO: 132).

In some embodiments, the amino acid spacer is GGGS (SEQ ID NO: 99), GGGGA (SEQ ID NO: 101), GGGGS (SEQ ID NO: 102), GGGGG (SEQ ID NO: 103), GGAG (SEQ ID NO: 104), GGSG (SEQ ID NO: 105), AGGG (SEQ ID NO: 106), SGGG (SEQ ID NO: 107), GAGA (SEQ ID NO: 108), GSGS (SEQ ID NO: 109), GAGAGA (SEQ ID NO: 110), GSGSGS (SEQ ID NO: 111), GAGAGAGA (SEQ ID NO: 112), GSGSGSGS (SEQ ID NO: 113), GAGAGAGAGA (SEQ ID NO: 114), GSGSGSGSGS (SEQ ID NO: 115), GAGAGAGAGAGA (SEQ ID NO: 116), and GSGSGSGSGSGS (SEQ ID NO: 117), GGAGGA (SEQ ID NO: 118), GGSGGS (SEQ ID NO: 119), GGAG-GAGGA (SEQ ID NO: 120), GGSGGSGGS (SEQ ID NO: 121), GGAGGAGGAGGA (SEQ ID NO: 122), GGSGGSGGSGGS (SEQ ID NO: 123), GGAGGGAG (SEQ ID NO: 124), GGSGGGSG (SEQ ID NO: 125), GGAGGGAGGGAG (SEQ ID NO: 126), and GGSGGGSGGGSG (SEQ ID NO: 127), GGGGAGGG-GAGGGA (SEQ ID NO: 128), GGGGSGGGGGGGGS (SEQ ID NO: 129), AAAL (SEQ ID NO: 133), AAAK (SEQ ID NO: 134), AAAR (SEQ ID NO: 135), EGKSSGSGS-ESKST (SEQ ID NO: 136), GSAGSAAGSGEF (SEQ ID NO: 137), AEAAAKEAAAKA (SEQ ID NO: 138), KES-GSVSSEQLAQFRSLD (SEQ ID NO: 139), GEN-LYFQSGG (SEQ ID NO: 140), SACYCELS (SEQ ID NO: 141), RSIAT (SEQ ID NO: 142), RPACK-IPNDLKQKVMNH (SEQ ID NO: 143), GGSAGGSGSGSSGGSSGASGTGTAGGTGSGSGTGSG (SEQ ID NO: 144), AAANSSIDLISVPVDSR (SEQ ID NO: 145), GGSGGGSEGGGSEGGGSEGGGSEGGGSEGGGSGGGS (SEQ ID NO: 146), EAAAK (SEQ ID NO: 147), or PAPAP (SEQ ID NO: 148).

In any of the aforementioned embodiments, the polypeptide described herein has a serum half-life of at least 7 days.

In any of the aforementioned embodiments, the polypeptide described herein binds to human bone morphogenetic protein 9 (BMP9) with a $K_D$ of 200 pM or higher. In some embodiments, the polypeptide binds to activin and/or myostatin and has reduced (e.g., weak) binding to human BMP9. In some embodiments, the polypeptide does not substantially bind to human BMP9.

In any of the aforementioned embodiments, the polypeptide described herein binds to human activin A with a $K_D$ of 800 pM or less.

In any of the aforementioned embodiments, the polypeptide described herein binds to human activin B with a $K_D$ of approximately 800 pM or less.

In any of the aforementioned embodiments, the polypeptide described herein binds to human GDF-11 with a $K_D$ of approximately 5 pM or higher.

In another aspect, the invention features a nucleic acid molecule encoding a polypeptide described herein (e.g., a polypeptide including an extracellular ActRIIa variant having a sequence of any one of SEQ ID NOs: 1-72 (e.g., SEQ ID NOs: 6-72). In another aspect, the invention also features a vector including the nucleic acid molecule described herein.

In another aspect, the invention features a host cell that expresses a polypeptide described herein, wherein the host cell includes a nucleic acid molecule or a vector described in the previous two aspects, wherein the nucleic acid molecule or vector is expressed in the host cell.

In another aspect, the invention features a method of preparing a polypeptide described herein, wherein the method includes: a) providing a host cell including a nucleic acid molecule or a vector described herein, and b) expressing the nucleic acid molecule or vector in the host cell under conditions that allow for the formation of the polypeptide.

In another aspect, the invention features a pharmaceutical composition including a polypeptide, nucleic acid molecule, or vector described herein and one or more pharmaceutically acceptable carriers or excipients. In some embodiments of the pharmaceutical composition, the polypeptide, nucleic acid molecule, or vector is in a therapeutically effective amount.

In another aspect, the invention also features a construct including two identical polypeptides (e.g., a homodimer) each including an extracellular ActRIIa variant having a sequence of any one of SEQ ID NOs: 1-72 (e.g., SEQ ID NOs: 6-72) fused to the N- or C-terminus of an Fc domain monomer (e.g., the sequence of SEQ ID NO: 97). The two Fc domain monomers in the two polypeptides interact to form an Fc domain in the construct.

In another aspect, the invention also features a construct including two different polypeptides (e.g., a heterodimer) each including an extracellular ActRIIa variant having a sequence of any one of SEQ ID NOS: 1-72 (e.g., SEQ ID NOs: 6-72) fused to the N- or C-terminus of an Fc domain monomer (e.g., the sequence of SEQ ID NO: 97). The two Fc domain monomers in the two polypeptides interact to form an Fc domain in the construct.

In another aspect, the invention features a method of increasing muscle mass in a subject in need thereof. The method includes administering to the subject a therapeutically effective amount of a polypeptide, nucleic acid molecule, or vector described herein or a pharmaceutical composition described herein.

In some embodiments of the method of increasing muscle mass in a subject, the subject has Duchenne muscular dystrophy (DMD), facioscapulohumeral muscular dystrophy (FSHD), inclusion body myositis (IBM), amyotrophic lateral sclerosis (ALS), sarcopenia, or cancer cachexia.

In another aspect, the invention features a method of affecting myostatin, activin, and/or BMP9 signaling (e.g., reducing or inhibiting the binding of myostatin, activin, and/or BMP9 to their receptors) in a subject having a disease or condition involving weakness and atrophy of muscles, wherein method includes administering to the subject a therapeutically effective amount of a polypeptide, nucleic acid molecule, or vector described herein or a pharmaceutical composition described herein. In some embodiments of this aspect, the disease or condition is DMD, FSHD, IBM, ALS, sarcopenia, or cancer cachexia. In another aspect, the invention features a method of treating a subject having DMD by administering to the subject a therapeutically effective amount of a polypeptide, nucleic acid molecule, or vector described herein or a pharmaceutical composition described herein.

In another aspect, the invention features a method of treating a subject having FSHD by administering to the subject a therapeutically effective amount of a polypeptide, nucleic acid molecule, or vector described herein or a pharmaceutical composition described herein.

In another aspect, the invention features a method of treating a subject having IBM by administering to the subject a therapeutically effective amount of a polypeptide, nucleic acid molecule, or vector described herein or a pharmaceutical composition described herein.

In another aspect, the invention features a method of treating a subject having ALS by administering to the subject a therapeutically effective amount of a polypeptide, nucleic acid molecule, or vector described herein or a pharmaceutical composition described herein.

In another aspect, the invention features a method of reducing body fat in a subject in need thereof by administering to the subject a therapeutically effective amount of a polypeptide, a nucleic acid molecule, or vector described herein or a pharmaceutical composition described herein.

In another aspect, the invention features a method of reducing body weight in a subject in need thereof by administering to the subject a therapeutically effective amount of a polypeptide, a nucleic acid molecule, or vector described herein or a pharmaceutical composition described herein.

In another aspect, the invention features a method of reducing blood glucose in a subject in need thereof by administering to the subject a therapeutically effective amount of a polypeptide, a nucleic acid molecule, or vector described herein or a pharmaceutical composition described herein.

In another aspect, the invention features a method of increasing insulin sensitivity in a subject in need thereof, by administering to the subject a therapeutically effective amount of a polypeptide, a nucleic acid molecule, or vector described herein or a pharmaceutical composition described herein.

In some embodiments of any of the above aspects, the subject has or is at risk of developing a metabolic disease. In some embodiments, the metabolic disease is selected from the group including obesity, Type-1 diabetes, and Type-2 diabetes.

In another aspect, the invention features a method of affecting myostatin, activin, and/or BMP9 signaling (e.g., reducing or inhibiting the binding of myostatin, activin, and/or BMP9 to their receptors) in a subject having or at risk of developing a metabolic disease by administering to the subject a therapeutically effective amount of a polypeptide, a nucleic acid molecule, or vector described herein or a pharmaceutical composition described herein.

In another aspect, the invention features a method of treating and/or preventing a metabolic disease in a subject by administering to the subject a therapeutically effective amount of a polypeptide, a nucleic acid molecule, or vector described herein or a pharmaceutical composition described herein. In some embodiments of any of the above aspect, the metabolic disease is selected from the group including obesity, Type-1 diabetes, and Type-2 diabetes. In some embodiments of any of the above aspects, the metabolic disease is obesity. In some embodiments of any of the above aspects, the metabolic disease is Type-1 diabetes. In some embodiments of any of the above aspects, the metabolic disease is Type-2 diabetes.

In some embodiments of any of the above aspects, the method reduces body weight and/or percentage of body weight gain of said subject. In some embodiments of any of the above aspects, the method reduces amount of body fat and/or percentage of body fat of said subject. In some embodiments of any of the above aspects, the method does not affect the appetite for food intake of said subject. In some embodiments of any of the above aspects, the method reduces adiposity of said subject. In some embodiments of any of the above aspects, the method reduces the weights of epididymal and perirenal fat pads of said subject. In some embodiments of any of the above aspects, the method reduces the amount of subcutaneous and/or visceral fat of said subject. In some embodiments of any of the above aspects, the method lowers the level of fasting insulin of said subject. In some embodiments of any of the above aspects, the method lowers the level of blood glucose of said subject. In some embodiments of any of the above aspects, the method increases insulin sensitivity of said subject. In some embodiments of any of the above aspects, the method increases the rate of glucose clearance of said subject. In some embodiments of any of the above aspects, the method improves the serum lipid profile of said subject. In some embodiments of any of the above aspects, the method does not reduce lean mass.

In some embodiments of any of the above aspects, the method increases muscle mass.

In some embodiments of any of the above aspects, the method reduces or inhibits the binding of activin and/or myostatin to their receptors.

In some embodiments of any of the above aspects, the polypeptide, nucleic acid, vector, or pharmaceutical composition is administered in an amount sufficient to increase muscle mass and/or strength, affect myostatin, activin, and/or BMP9 signaling in the subject, or reduce or inhibit the binding of activin and/or myostatin to their receptors.

In some embodiments of any of the above aspects, the polypeptide, nucleic acid, vector, or pharmaceutical composition is administered in an amount sufficient to reduce body fat, reduce the amount of subcutaneous fat, reduce the amount of visceral fat, reduce adiposity, reduce the weights of epididymal and perirenal fat pads, reduce body fat percentage, reduce body weight, reduce the percentage of body weight gain, reduce fasting insulin level, reduce blood glucose level, increase insulin sensitivity, affect myostatin, activin, and/or BMP9 signaling in the subject, reduce the proliferation of adipose cells, reduce or inhibit the binding of activin and/or myostatin to their receptors, reduce LDL, reduce triglycerides, improve the serum lipid profile, regulate insulin biosynthesis and/or secretion from B-cells, delay, postpone, or reduce the need for insulin, or increase glucose clearance.

In some embodiments of any of the methods described herein, the method does not cause a vascular complication (e.g., an increase vascular permeability or leakage) in the subject. In some embodiments of any of the methods described herein, the method increases bone mineral density in the subject.

In some embodiments of any of the above aspects, the variant has the sequence of SEQ ID NO: 69. In some embodiments, the variant having the sequence of SEQ ID NO: 69 has the amino acid K at position $X_{17}$, the amino acid sequence TEEN or TKEN at positions $X_{23}$, $X_{24}$, $X_{25}$, and $X_{26}$, and/or a C-terminal extension (e.g., 1, 2, 3, 4, 5, 6 or more additional amino acids at the C-terminus, e.g., the amino acids NP or NPVTPK (SEQ ID NO: 155). In some embodiments of any of the above aspects, the method includes increasing muscle mass or treating a muscle disorder in a subject in need thereof (e.g., a subject having DMD, FSHD, IBM, ALS, sarcopenia, or cancer cachexia), affecting myostatin, activin, and/or BMP9 signaling in a subject (e.g., a subject having or at risk of developing DMD, FSHD, IBM, ALS, sarcopenia, cancer cachexia, obesity, Type-1 diabetes, or Type-2 diabetes), reducing body fat or body weight in a subject (e.g., a subject having obesity, Type-1 diabetes, or Type-2 diabetes), or treating and/or preventing a metabolic disease in a subject (e.g., a subject having or at risk of developing obesity, Type-1 diabetes, or Type-2 diabetes) by administering to the subject a therapeutically effective amount of a variant having the sequence of SEQ ID NO: 69, optionally having the amino acid K at position $X_{17}$, the amino acid sequence TEEN or TKEN at positions $X_{23}$, $X_{24}$, $X_{25}$, and $X_{26}$, and/or a C-terminal extension, or a pharmaceutical composition containing said variant.

In some embodiments of any of the above aspects, the variant has the sequence of SEQ ID NO: 58. In some embodiments, the variant having the sequence of SEQ ID NO: 58 has the amino acid K at position $X_{17}$, the amino acid sequence TEEN or TKEN at positions $X_{23}$, $X_{24}$, $X_{25}$, and $X_{26}$, and/or a C-terminal extension (e.g., 1, 2, 3, 4, 5, 6 or more additional amino acids at the C-terminus, e.g., the amino acids NP or NPVTPK (SEQ ID NO: 155)). In some embodiments of any of the above aspects, the method includes increasing muscle mass or treating a muscle disorder in a subject in need thereof (e.g., a subject having DMD, FSHD, IBM, ALS, sarcopenia, or cancer cachexia), affecting myostatin, activin, and/or BMP9 signaling in a subject (e.g., a subject having or at risk of developing DMD, FSHD, IBM, ALS, sarcopenia, cancer cachexia, obesity, Type-1 diabetes, or Type-2 diabetes), reducing body fat or body weight in a subject (e.g., a subject having obesity, Type-1 diabetes, or Type-2 diabetes), or treating and/or preventing a metabolic disease in a subject (e.g., a subject having or at risk of developing obesity, Type-1 diabetes, or Type-2 diabetes) by administering to the subject a therapeutically effective amount of a variant having the sequence of SEQ ID NO: 58, optionally having the amino acid K at position $X_{17}$, the amino acid sequence TEEN or TKEN at positions $X_{23}$, $X_{24}$, $X_{25}$, and $X_{26}$, and/or a C-terminal extension, or a pharmaceutical composition containing said variant.

In some embodiments of any of the above aspects, the variant has the sequence of SEQ ID NO: 6. In some embodiments, the variant having the sequence of SEQ ID NO: 6 has the amino acid K at position $X_{17}$, the amino acid sequence TEEN or TKEN at positions $X_{23}$, $X_{24}$, $X_{25}$, and $X_{26}$, and/or a C-terminal extension (e.g., 1, 2, 3, 4, 5, 6, or more additional amino acids at the C-terminus, e.g., the amino acids NP or NPVTPK (SEQ ID NO: 155). In some embodiments of any of the above aspects, the method includes increasing muscle mass or treating a muscle disorder in a subject in need thereof (e.g., a subject having DMD, FSHD, IBM, ALS, sarcopenia, or cancer cachexia), affecting myostatin, activin, and/or BMP9 signaling in a subject (e.g., a subject having or at risk of developing DMD, FSHD, IBM, ALS, sarcopenia, cancer cachexia, obesity, Type-1 diabetes, or Type-2 diabetes), reducing body fat or body weight in a subject (e.g., a subject having obesity, Type-1 diabetes, or Type-2 diabetes), or treating and/or preventing a metabolic disease in a subject (e.g., a subject having or at risk of developing obesity, Type-1 diabetes, or Type-2 diabetes) by administering to the subject a therapeutically effective amount of a variant having the sequence of SEQ ID NO: 6, optionally having the amino acid K at position $X_{17}$, the amino acid sequence TEEN or TKEN at positions $X_{23}$, $X_{24}$, $X_{25}$, and $X_{26}$, and/or a C-terminal extension, or a pharmaceutical composition containing said variant.

In some embodiments of any of the above aspects, the variant has the sequence of SEQ ID NO: 38. In some embodiments, the variant having the sequence of SEQ ID NO: 38 has the amino acid K at position $X_{17}$, the amino acid sequence TEEN or TKEN at positions $X_{23}$, $X_{24}$, $X_{25}$, and $X_{26}$, and/or a C-terminal extension (e.g., 1, 2, 3, 4, 5, 6, or more additional amino acids at the C-terminus, e.g., the amino acids NP or NPVTPK (SEQ ID NO: 155). In some embodiments of any of the above aspects, the method includes increasing muscle mass or treating a muscle disorder in a subject in need thereof (e.g., a subject having DMD, FSHD, IBM, ALS, sarcopenia, or cancer cachexia), affecting myostatin, activin, and/or BMP9 signaling in a subject (e.g., a subject having or at risk of developing DMD, FSHD, IBM, ALS, sarcopenia, cancer cachexia, obesity, Type-1 diabetes, or Type-2 diabetes), reducing body fat or body weight in a subject (e.g., a subject having obesity, Type-1 diabetes, or Type-2 diabetes), or treating and/or preventing a metabolic disease in a subject (e.g., a subject having or at risk of developing obesity, Type-1 diabetes, or Type-2 diabetes) by administering to the subject a therapeutically effective amount of a variant having the sequence of SEQ ID NO: 38, optionally having the amino acid K at position $X_{17}$, the amino acid sequence TEEN or TKEN at positions $X_{23}$, $X_{24}$, $X_{25}$, and $X_{26}$, and/or a C-terminal extension, or a pharmaceutical composition containing said variant.

In some embodiments of any of the above aspects, the variant has the sequence of SEQ ID NO: 41. In some embodiments, the variant having the sequence of SEQ ID NO: 41 has the amino acid K at position $X_{17}$, the amino acid sequence TEEN or TKEN at positions $X_{23}$, $X_{24}$, $X_{25}$, and $X_{26}$, and/or a C-terminal extension (e.g., 1, 2, 3, 4, 5, 6, or more additional amino acids at the C-terminus, e.g., the amino acids NP or NPVTPK (SEQ ID NO: 155). In some embodiments of any of the above aspects, the method includes increasing muscle mass or treating a muscle disorder in a subject in need thereof (e.g., a subject having DMD, FSHD, IBM, ALS, sarcopenia, or cancer cachexia), affecting myostatin, activin, and/or BMP9 signaling in a subject (e.g., a subject having or at risk of developing DMD, FSHD, IBM, ALS, sarcopenia, cancer cachexia, obesity, Type-1 diabetes, or Type-2 diabetes), reducing body fat or body weight in a subject (e.g., a subject having obesity, Type-1 diabetes, or Type-2 diabetes), or treating and/or preventing a metabolic disease in a subject (e.g., a subject having or at risk of developing obesity, Type-1 diabetes, or Type-2 diabetes) by administering to the subject a therapeutically effective amount of a variant having the sequence of SEQ ID NO: 41, optionally having the amino acid K at position $X_{17}$, the amino acid sequence TEEN or TKEN at positions $X_{23}$, $X_{24}$, $X_{25}$, and $X_{26}$, and/or a C-terminal extension, or a pharmaceutical composition containing said variant.

In some embodiments of any of the above aspects, the variant has the sequence of SEQ ID NO: 44. In some embodiments, the variant having the sequence of SEQ ID NO: 44 has the amino acid K at position $X_{17}$, the amino acid sequence TEEN or TKEN at positions $X_{23}$, $X_{24}$, $X_{25}$, and $X_{26}$, and/or a C-terminal extension (e.g., 1, 2, 3, 4, 5, 6 or more additional amino acids at the C-terminus, e.g., the amino acids NP or NPVTPK (SEQ ID NO: 155). In some embodiments of any of the above aspects, the method includes increasing muscle mass or treating a muscle disorder in a subject in need thereof (e.g., a subject having DMD, FSHD, IBM, ALS, sarcopenia, or cancer cachexia), affecting myostatin, activin, and/or BMP9 signaling in a subject (e.g., a subject having or at risk of developing DMD, FSHD, IBM, ALS, sarcopenia, cancer cachexia, obesity, Type-1 diabetes, or Type-2 diabetes), reducing body fat or body weight in a subject (e.g., a subject having obesity, Type-1 diabetes, or Type-2 diabetes), or treating and/or preventing a metabolic disease in a subject (e.g., a subject having or at risk of developing obesity, Type-1 diabetes, or Type-2 diabetes) by administering to the subject a therapeutically effective amount of a variant having the sequence of SEQ ID NO: 44, optionally having the amino acid K at position $X_{17}$, the amino acid sequence TEEN or TKEN at positions $X_{23}$, $X_{24}$, $X_{25}$, and $X_{26}$, and/or a C-terminal extension, or a pharmaceutical composition containing said variant.

In some embodiments of any of the above aspects, the variant has the sequence of SEQ ID NO: 70. In some embodiments, the variant having the sequence of SEQ ID NO: 70 has the amino acid K at position $X_{17}$, the amino acid sequence TEEN or TKEN at positions $X_{23}$, $X_{24}$, $X_{25}$, and $X_{26}$, and/or a C-terminal extension (e.g., 1, 2, 3, 4, 5, 6 or more additional amino acids at the C-terminus, e.g., the amino acids NP or NPVTPK (SEQ ID NO: 155). In some embodiments of any of the above aspects, the method includes increasing muscle mass or treating a muscle disorder in a subject in need thereof (e.g., a subject having DMD, FSHD, IBM, ALS, sarcopenia, or cancer cachexia), affecting myostatin, activin, and/or BMP9 signaling in a subject (e.g., a subject having or at risk of developing DMD, FSHD, IBM, ALS, sarcopenia, cancer cachexia, obesity, Type-1 diabetes, or Type-2 diabetes), reducing body fat or body weight in a subject (e.g., a subject having obesity, Type-1 diabetes, or Type-2 diabetes), or treating and/or preventing a metabolic disease in a subject (e.g., a subject having or at risk of developing obesity, Type-1 diabetes, or Type-2 diabetes) by administering to the subject a therapeutically effective amount of a variant having the sequence of SEQ ID NO: 70, optionally having the amino acid K at position $X_{17}$, the amino acid sequence TEEN or TKEN at positions $X_{23}$, $X_{24}$, $X_{25}$, and $X_{26}$, and/or a C-terminal extension, or a pharmaceutical composition containing said variant.

In some embodiments of any of the above aspects, the variant has the sequence of SEQ ID NO: 71. In some embodiments, the variant having the sequence of SEQ ID NO: 71 has the amino acid K at position $X_{17}$, the amino acid sequence TEEN or TKEN at positions $X_{23}$, $X_{24}$, $X_{25}$, and $X_{26}$, and/or a C-terminal extension (e.g., 1, 2, 3, 4, 5, 6 or more additional amino acids at the C-terminus, e.g., the amino acids VTPK). In some embodiments of any of the above aspects, the method includes increasing muscle mass or treating a muscle disorder in a subject in need thereof (e.g., a subject having DMD, FSHD, IBM, ALS, sarcopenia, or cancer cachexia), affecting myostatin, activin, and/or BMP9 signaling in a subject (e.g., a subject having or at risk of developing DMD, FSHD, IBM, ALS, sarcopenia, cancer cachexia, obesity, Type-1 diabetes, or Type-2 diabetes), reducing body fat or body weight in a subject (e.g., a subject having obesity, Type-1 diabetes, or Type-2 diabetes), or treating and/or preventing a metabolic disease in a subject (e.g., a subject having or at risk of developing obesity, Type-1 diabetes, or Type-2 diabetes) by administering to the subject a therapeutically effective amount of a variant having the sequence of SEQ ID NO: 71, optionally having the amino acid K at position $X_{17}$, the amino acid sequence TEEN or TKEN at positions $X_{23}$, $X_{24}$, $X_{25}$, and $X_{26}$, and/or a C-terminal extension, or a pharmaceutical composition containing said variant.

In some embodiments of any of the above aspects, the variant has the sequence of SEQ ID NO: 72. In some embodiments, the variant having the sequence of SEQ ID NO: 72 has the amino acid K at position $X_{17}$ and/or the amino acid sequence TEEN or TKEN at positions $X_{23}$, $X_{24}$, $X_{25}$, and $X_{26}$. In some embodiments of any of the above aspects, the method includes increasing muscle mass or treating a muscle disorder in a subject in need thereof (e.g., a subject having DMD, FSHD, IBM, ALS, sarcopenia, or cancer cachexia), affecting myostatin, activin, and/or BMP9 signaling in a subject (e.g., a subject having or at risk of developing DMD, FSHD, IBM, ALS, sarcopenia, cancer cachexia, obesity, Type-1 diabetes, or Type-2 diabetes), reducing body fat or body weight in a subject (e.g., a subject having obesity, Type-1 diabetes, or Type-2 diabetes), or treating and/or preventing a metabolic disease in a subject (e.g., a subject having or at risk of developing obesity, Type-1 diabetes, or Type-2 diabetes) by administering to the subject a therapeutically effective amount of a variant having the sequence of SEQ ID NO: 72, optionally having the amino acid K at position $X_{17}$ and/or the amino acid sequence TEEN or TKEN at positions $X_{23}$, $X_{24}$, $X_{25}$, and $X_{26}$.

Definitions

As used herein, the term "extracellular activin receptor type IIa (ActRIIa) variant" refers to a peptide including a soluble, extracellular portion of the single transmembrane receptor, ActRIIa, that has at least one amino acid substitution relative to a wild-type extracellular ActAIIa (e.g., bold portion of the sequence of SEQ ID NO: 75 shown below) or an extracellular ActAIIa having any one of the sequences of SEQ ID NOs: 76-96. The sequence of the wild-type, human ActAIIa precursor protein is shown below (SEQ ID NO: 75), in which the signal peptide is italicized and the extracellular portion is bold.

```
Wild-type, human ActRIIa precursor protein (SEQ
ID NO: 75):
MGAAAKLAFAVFLISCSSGAILGRSETQECLFFNANWEKDRTNQTGVEP

CYGDKDKRRHCFATWKNISGSIEIVKQGCWLDDINCYDRTDCVEKKDSP

EVYFCCCEGNMCNEKFSYFPEMEVTQPTSNPVTPKPPYYNILLYSLVPL

MLIAGIVICAFWVYRHHKMAYPPVLVPTQDPGPPPPSPLLGLKPLQLLE
```

```
                        -continued
VKARGRFGCVWKAQLLNEYVAVKIFPIQDKQSWQNEYEVYSLPGMKHEN

ILQFIGAEKRGTSVDVDLWLITAFHEKGSLSDFLKANVVSWNELCHIAE

TMARGLAYLHEDIPGLKDGHKPAISHRDIKSKNVLLKNNLTACIADFGL

ALKFEAGKSAGDTHGQVGTRRYMAPEVLEGAINFQRDAFLRIDMYAMGL

VLWELASRCTAADGPVDEYMLPFEEEIGQHPSLEDMQEVVVHKKKRPVL

RDYWQKHAGMAMLCETIEECWDHDAEARLSAGCVGERITQMQRLTNIIT

TEDIVTVVTMVTNVDFPPKESSL
```

An extracellular ActRIIa variant may have a sequence of any one of SEQ ID NOs: 1-72. In particular embodiments, an extracellular ActRIIa variant has a sequence of any one of SEQ ID NOs: 6-72 (Table 2). In some embodiments, an extracellular ActRIIa variant may have at least 85% (e.g., at least 85%, 87%, 90%, 92%, 95%, 97%, or greater) amino acid sequence identity to the sequence of a wild-type extracellular ActRIIa (SEQ ID NO: 73).

As used herein, the term "extracellular ActRIIb variant" refers to a peptide including a soluble, extracellular portion of the single transmembrane receptor, ActRIIb, that has at least one amino acid substitution relative to a wild-type extracellular ActRIIb (e.g., the sequence of SEQ ID NO: 74). An extracellular ActRIIb variant may have the sequence of SEQ ID NO: 149 shown below:

```
extracellular ActRIIb variant (SEQ ID NO: 149):
GRGEAETRECIFYNANWEKDRTNQSGLEPCYGDQDKRRHCFASWKNSSG

TIELVKQGCWLDDINCYDRQECVAKKDSPEVYFCCCEGNFCNERFTHLP

EAGGPEVTYEPPPTAPT
```

As used herein, the term "linker" refers to a linkage between two elements, e.g., peptides or protein domains. A polypeptide described herein may include an extracellular ActRIIa variant (e.g., an extracellular ActRIIa variant having a sequence of any one of SEQ ID NOs: 1-72 (e.g., SEQ ID NOs: 6-72) fused to a moiety. The moiety may increase stability or improve pharmacokinetic properties of the polypeptide. The moiety (e.g., Fc domain monomer, a wild-type Fc domain, an Fc domain with amino acid substitutions (e.g., one or more substitutions that reduce dimerization), an albumin-binding peptide, a fibronectin domain, or a human serum albumin) may be fused to the polypeptide by way of a linker. A linker can be a covalent bond or a spacer. The term "bond" refers to a chemical bond, e.g., an amide bond or a disulfide bond, or any kind of bond created from a chemical reaction, e.g., chemical conjugation. The term "spacer" refers to a moiety (e.g., a polyethylene glycol (PEG) polymer) or an amino acid sequence (e.g., a 1-200 amino acid sequence) occurring between two elements, e.g., peptides or protein domains, to provide space and/or flexibility between the two elements. An amino acid spacer is part of the primary sequence of a polypeptide (e.g., fused to the spaced peptides via the polypeptide backbone). The formation of disulfide bonds, e.g., between two hinge regions that form an Fc domain, is not considered a linker.

As used herein, the term "Fc domain" refers to a dimer of two Fc domain monomers. An Fc domain has at least 80% sequence identity (e.g., at least 85%, 90%, 95%, 97%, or 100% sequence identity) to a human Fc domain that includes at least a $C_H2$ domain and a $C_H3$ domain. An Fc domain monomer includes second and third antibody constant domains ($C_H2$ and $C_H3$). In some embodiments, the Fc domain monomer also includes a hinge domain. An Fc domain does not include any portion of an immunoglobulin that is capable of acting as an antigen-recognition region, e.g., a variable domain or a complementarity determining region (CDR). In the wild-type Fc domain, the two Fc domain monomers dimerize by the interaction between the two $C_H3$ antibody constant domains, as well as one or more disulfide bonds that form between the hinge domains of the two dimerizing Fc domain monomers. In some embodiments, an Fc domain may be mutated to lack effector functions, typical of a "dead Fc domain." In certain embodiments, each of the Fc domain monomers in an Fc domain includes amino acid substitutions in the $C_H2$ antibody constant domain to reduce the interaction or binding between the Fc domain and an Fcγ receptor. In some embodiments, the Fc domain contains one or more amino acid substitutions that reduce or inhibit Fc domain dimerization. An Fc domain can be any immunoglobulin antibody isotype, including IgG, IgE, IgM, IgA, or IgD. Additionally, an Fc domain can be an IgG subtype (e.g., IgG1, IgG2a, IgG2b, IgG3, or IgG4). The Fc domain can also be a non-naturally occurring Fc domain, e.g., a recombinant Fc domain.

As used herein, the term "albumin-binding peptide" refers to an amino acid sequence of 12 to 16 amino acids that has affinity for and functions to bind serum albumin. An albumin-binding peptide can be of different origins, e.g., human, mouse, or rat. In some embodiments, an albumin-binding peptide has the sequence DICLPRWGCLW (SEQ ID NO: 152).

As used herein, the term "fibronectin domain" refers to a high molecular weight glycoprotein of the extracellular matrix, or a fragment thereof, that binds to, e.g., membrane-spanning receptor proteins such as integrins and extracellular matrix components such as collagens and fibrins. In some embodiments, a fibronectin domain is a fibronectin type III domain (SEQ ID NO: 153) having amino acids 610-702 of the sequence of UniProt ID NO: P02751. In other embodiments, a fibronectin domain is an adnectin protein.

As used herein, the term "human serum albumin" refers to the albumin protein present in human blood plasma. Human serum albumin is the most abundant protein in the blood. It constitutes about half of the blood serum protein. In some embodiments, a human serum albumin has the sequence of UniProt ID NO: P02768 (SEQ ID NO: 154).

As used herein, the term "fused" is used to describe the combination or attachment of two or more elements, components, or protein domains, e.g., peptides or polypeptides, by means including chemical conjugation, recombinant means, and chemical bonds, e.g., amide bonds. For example, two single peptides in tandem series can be fused to form one contiguous protein structure, e.g., a polypeptide, through chemical conjugation, a chemical bond, a peptide linker, or any other means of covalent linkage. In some embodiments of a polypeptide described herein, an extracellular ActRIIa variant (e.g., an extracellular ActAIIa variant having the sequence of any one of SEQ ID NOs: 1-72 (e.g., SEQ ID NOs: 6-72)) may be fused in tandem series to the N- or C-terminus of a moiety (e.g., Fc domain monomer (e.g., the sequence of SEQ ID NO: 97) a wild-type Fc domain (e.g., the sequence of SEQ ID NO: 151), an Fc domain with amino acid substitutions (e.g., one or more substitutions that reduce dimerization), an albumin-binding peptide (e.g., the sequence of SEQ ID NO: 152), a fibronectin domain (e.g., the sequence of SEQ ID NO: 153), or a human serum albumin (e.g., the sequence of SEQ ID NO: 154)) by way of a linker. For example, an extracellular ActRIIa variant is fused to a moiety (e.g., an Fc domain monomer, a wild-type Fc domain, an Fc domain with amino acid substitutions (e.g., one or more substitutions that reduce dimerization), an albumin-binding peptide, a fibronectin domain, or a human serum albumin) by way of a peptide linker, in which the N-terminus of the peptide linker is fused to the C-terminus of the extracellular ActRIIa variant through a chemical bond, e.g., a peptide bond, and the C-terminus of the peptide linker is fused to the N-terminus of the moiety (e.g., Fc domain monomer, wild-type Fc domain, Fc domain with amino acid substitutions (e.g., one or more substitutions that reduce dimerization), albumin-binding peptide, fibronectin domain, or human serum albumin) through a chemical bond, e.g., a peptide bond.

As used herein, the term "C-terminal extension" refers to the addition of one or more amino acids to the C-terminus of a polypeptide including an extracellular ActRIIa variant (e.g., an extracellular ActAIIa variant having the sequence of any one of SEQ ID NOs: 1-70 (e.g., SEQ ID NOs: 6-70). The C-terminal extension can be 1-6 amino acids (e.g., 1, 2, 3, 4, 5, 6 or more amino acids). Exemplary C-terminal extensions are the amino acid sequence NP (a two amino acid C-terminal extension) and the amino acid sequence NPVTPK (SEQ ID NO: 155) (a six amino acid C-terminal extension). Any amino acid sequence that does not disrupt the activity of the polypeptide can be used. SEQ ID NO: 71, which is the sequence of SEQ ID NO: 69 with a C-terminal extension of NP, and SEQ ID NO: 72, which is the sequence of SEQ ID NO: 69 with a C-terminal extension of NPVTPK, represent two of the possible ways that a polypeptide of the invention can be modified to include a C-terminal extension.

As used herein, the term "percent (%) identity" refers to the percentage of amino acid (or nucleic acid) residues of a candidate sequence, e.g., an extracellular ActRIIa variant, that are identical to the amino acid (or nucleic acid) residues of a reference sequence, e.g., a wild-type extracellular ActRIIa (e.g., SEQ ID NO: 73), after aligning the sequences and introducing gaps, if necessary, to achieve the maximum percent identity (i.e., gaps can be introduced in one or both of the candidate and reference sequences for optimal alignment and non-homologous sequences can be disregarded for comparison purposes). Alignment for purposes of determining percent identity can be achieved in various ways that are within the skill in the art, for instance, using publicly available computer software such as BLAST, ALIGN, or Megalign (DNASTAR) software. Those skilled in the art can determine appropriate parameters for measuring alignment, including any algorithms needed to achieve maximal alignment over the full length of the sequences being compared. In some embodiments, the percent amino acid (or nucleic acid) sequence identity of a given candidate sequence to, with, or against a given reference sequence (which can alternatively be phrased as a given candidate sequence that has or includes a certain percent amino acid (or nucleic acid) sequence identity to, with, or against a given reference sequence) is calculated as follows:

$$100 \times (\text{fraction of } A/B)$$

where A is the number of amino acid (or nucleic acid) residues scored as identical in the alignment of the candidate sequence and the reference sequence, and where B is the total number of amino acid (or nucleic acid) residues in the reference sequence. In some embodiments where the length of the candidate sequence does not equal to the length of the reference sequence, the percent amino acid (or nucleic acid)

sequence identity of the candidate sequence to the reference sequence would not equal to the percent amino acid (or nucleic acid) sequence identity of the reference sequence to the candidate sequence.

In particular embodiments, a reference sequence aligned for comparison with a candidate sequence may show that the candidate sequence exhibits from 50% to 100% identity across the full length of the candidate sequence or a selected portion of contiguous amino acid (or nucleic acid) residues of the candidate sequence. The length of the candidate sequence aligned for comparison purpose is at least 30%, e.g., at least 40%, e.g., at least 50%, 60%, 70%, 80%, 90%, or 100% of the length of the reference sequence. When a position in the candidate sequence is occupied by the same amino acid (or nucleic acid) residue as the corresponding position in the reference sequence, then the molecules are identical at that position.

As used herein, the term "serum half-life" refers to, in the context of administering a therapeutic protein to a subject, the time required for plasma concentration of the protein in the subject to be reduced by half. The protein can be redistributed or cleared from the bloodstream, or degraded, e.g., by proteolysis. As described herein, a polypeptide including an extracellular ActRIIa variant (e.g., an extracellular ActRIIa variant having a sequence of any one of SEQ ID NOs: 1-72 (e.g., SEQ ID NOs: 6-72)) displays a serum half-life of 7 days in humans.

As used herein, the term "metabolic disease" refers to a disease, disorder, or syndrome that is related to a subject's metabolism, such as breaking down carbohydrates, proteins, and fats in food to release energy, and converting chemicals into other substances and transporting them inside cells for energy utilization and/or storage. Some symptoms of a metabolic disease include high serum triglycerides, high low-density cholesterol (LDL), low high-density cholesterol (HDL), and/or high fasting insulin levels, elevated fasting plasma glucose, abdominal (central) obesity, and elevated blood pressure. Metabolic diseases increase the risk of developing other diseases, such as cardiovascular disease. In the present invention, metabolic diseases include, but are not limited to, obesity, Type-1 diabetes, and Type-2 diabetes.

As used herein, the term "percentage of body weight gain" refers to the percentage of gained body weight compared to a prior body weight of a subject at a prior time. The percentage of body weight gain can be calculated as follows:

$$100 \times [(\text{body weight at a later time} -$$
$$\text{body weight at a prior time})/(\text{body weight at a prior time})]$$

In the present invention, administration of a polypeptide including an extracellular ActRIIa variant (e.g., an extracellular ActRIIa variant having the sequence of any one of SEQ ID NOs: 1-72 (e.g., SEQ ID NOs: 6-72), a nucleic acid molecule encoding a polypeptide including an extracellular ActRIIa variant (e.g., an extracellular ActRIIa variant having the sequence of any one of SEQ ID NOs: 1-72 (e.g., SEQ ID NOs: 6-72), or vector containing such a nucleic acid molecule to a subject reduces the percentage of body weight gain of the subject.

As used herein, the term "appetite for food intake" refers to a subject's natural desire or need for food. The appetite for food intake of a subject can be monitored by measuring the amount of food consumed after the polypeptide including an extracellular ActRIIa variant (e.g., an extracellular ActAIIa variant having the sequence of any one of SEQ ID NOs: 1-72 (e.g., SEQ ID NOs: 6-72) is administered. In the present invention, administration of a polypeptide including an extracellular ActRIIa variant (e.g., an extracellular ActRIIa variant having the sequence of any one of SEQ ID NOs: 1-72 (e.g., SEQ ID NOs: 6-72), a nucleic acid molecule encoding a polypeptide including an extracellular ActRIIa variant (e.g., an extracellular ActRIIa variant having the sequence of any one of SEQ ID NOs: 1-72 (e.g., SEQ ID NOs: 6-72), or vector containing such a nucleic acid molecule to a subject does not affect the subject's appetite for food intake.

As used herein, the term "adiposity" refers to the fat stored in the adipose tissue of a subject. In the present invention, administration of a polypeptide including an extracellular ActRIIa variant (e.g., an extracellular ActRIIa variant having the sequence of any one of SEQ ID NOs: 1-72 (e.g., SEQ ID NOs: 6-72)), a nucleic acid molecule encoding a polypeptide including an extracellular ActRIIa variant (e.g., an extracellular ActRIIa variant having the sequence of any one of SEQ ID NOs: 1-72 (e.g., SEQ ID NOs: 6-72), or vector containing such a nucleic acid molecule to a subject reduces the subject's adiposity without affecting lean mass.

As used herein, the term "lean mass" refers to a component of body composition which includes, e.g., lean mass, body fat, and body fluid. Normally lean mass is calculated by subtracting the weights of body fat and body fluid from total body weight. Typically, a subject's lean mass is between 60% and 90% of totally body weight. In the present invention, administration of a polypeptide including an extracellular ActRIIa variant (e.g., an extracellular ActAIIa variant having the sequence of any one of SEQ ID NOs: 1-72 (e.g., SEQ ID NOs: 6-72)), a nucleic acid molecule encoding a polypeptide including an extracellular ActRIIa variant (e.g., an extracellular ActAIIa variant having the sequence of any one of SEQ ID NOs: 1-72 (e.g., SEQ ID NOs: 6-72)), or vector containing such a nucleic acid molecule to a subject reduces the subject's adiposity (i.e., fat) without affecting lean mass.

As used herein, the term "epididymal and perirenal fat pads" refers to the tightly packed fat cells in the epididymis and around the kidney. In the present invention, administration of a polypeptide including an extracellular ActRIIa variant (e.g., an extracellular ActRIIa variant having the sequence of any one of SEQ ID NOs: 1-72 (e.g., SEQ ID NOs: 6-72), a nucleic acid molecule encoding a polypeptide including an extracellular ActRIIa variant (e.g., an extracellular ActRIIa variant having the sequence of any one of SEQ ID NOs: 1-72 (e.g., SEQ ID NOs: 6-72), or vector containing such a nucleic acid molecule to a subject reduces the weights of epididymal and perirenal fat pads of the subject.

As used herein, the term "fasting insulin" refers to a subject's level of insulin while the subject has not had any food intake for a length of time (i.e., 12-24 hours). Fasting insulin level is used in diagnosing metabolic diseases. Fasting insulin level is also used as an indication of whether a subject is at the risk of developing a metabolic disease. Normally, in a subject suffering from Type-1 diabetes, the subject's fasting insulin level is low compared to that of a healthy subject. In a subject suffering from insulin resistance (i.e., Type-2 diabetes), the subject's fasting insulin level is high compared to that of a healthy subject. In the present invention, administration of a polypeptide including an extracellular ActRIIa variant (e.g., an extracellular ActRIIa variant having the sequence of any one of SEQ ID NOs: 1-72 (e.g., SEQ ID NOs: 6-72), a nucleic acid molecule encoding a polypeptide including an extracellular ActRIIa variant (e.g., an extracellular ActAIIa variant having the sequence of any one of SEQ ID NOs: 1-72 (e.g., SEQ ID NOs: 6-72)), or vector containing such a nucleic acid molecule to a subject lowers the subject's fasting insulin level.

As used herein, the term "rate of glucose clearance" refers to the rate at which glucose is being cleared from the blood. The rate of glucose clearance can be measured in a glucose tolerance test (GTT). In a GTT, a subject is given a certain amount of glucose and blood samples are taken afterward to determine how quickly it is cleared from the blood. The rate of glucose clearance can be used as a parameter in diagnosing and/or determining the risk of developing metabolic diseases such as obesity, diabetes, and insulin resistance.

As used herein, the term "serum lipid profile" refers to the measurement of the distribution of different types of lipids and lipoproteins in a subject's serum. Such measurement can be accomplished by a panel of blood tests. The types of lipids and lipoproteins in a subject's serum include, but are not limited to, cholesterol (e.g., high-density lipoprotein (HDL) and low-density lipoprotein (LDL)), triglyceride, and free fatty acid (FFA). The distribution of the different types of lipids and lipoproteins can be used as a parameter in diagnosing and/or determining the risk of developing metabolic diseases such as obesity, diabetes, and insulin resistance. High levels of cholesterol, especially low-density lipoprotein, is generally regarded as an indication or risk factor for developing certain metabolic diseases, or in some severe medical cases, cardiovascular diseases. In the present invention, administration of a polypeptide including an extracellular ActRIIa variant (e.g., an extracellular ActRIIa variant having the sequence of any one of SEQ ID NOs: 1-72 (e.g., SEQ ID NOs: 6-72), a nucleic acid molecule encoding a polypeptide including an extracellular ActRIIa variant (e.g., an extracellular ActRIIa variant having the sequence of any one of SEQ ID NOs: 1-72 (e.g., SEQ ID NOs: 6-72), or vector containing such a nucleic acid molecule to a subject improves the subject's serum lipid profile such that the levels of cholesterol (especially low-density lipoprotein) and triglyceride are lowered.

As used herein, the term "affinity" or "binding affinity" refers to the strength of the binding interaction between two molecules. Generally, binding affinity refers to the strength of the sum total of non-covalent interactions between a molecule and its binding partner, such as an extracellular ActRIIa variant and BMP9 or activin A. Unless indicated otherwise, binding affinity refers to intrinsic binding affinity, which reflects a 1:1 interaction between members of a binding pair. The binding affinity between two molecules is commonly described by the dissociation constant ($K_D$) or the affinity constant ($K_A$). Two molecules that have low binding affinity for each other generally bind slowly, tend to dissociate easily, and exhibit a large $K_D$. Two molecules that have high affinity for each other generally bind readily, tend to remain bound longer, and exhibit a small $K_D$. The $K_D$ of two interacting molecules may be determined using methods and techniques well known in the art, e.g., surface plasmon resonance. $K_D$ is calculated as the ratio of $K_{off}/K_{on}$.

As used herein, the term "muscle mass" refers to a component of body composition. Normally muscle mass is calculated by subtracting the weights of body fat and body fluid from total body weight. The percentage of muscle mass may vary greatly among individuals depending on a subject's genetic makeup, age, race, and health status, etc. Typically, a subject's muscle mass may be between 20% and 50% of totally body weight.

As used herein, the phrase "affecting myostatin, activin, and/or BMP9 signaling" means changing the binding of myostatin, activin, and/or BMP9 to their receptors, e.g., ActRIIa, ActRIIb, and BMPRII (e.g., ActRIIa). In some embodiments, a polypeptide including an extracellular ActRIIa variant described herein reduces or inhibits the binding of myostatin, activin, and/or BMP9 to their receptors, e.g., ActRIIa, ActRIIb, and BMPRII (e.g., ActRIIa). As described herein, a polypeptide of the invention including an extracellular ActAIIa variant (e.g., an extracellular ActRIIa variant having the sequence of any one of SEQ ID NOs: 1-72 (e.g., SEQ ID NOs: 6-72) may have weak binding affinity to BMP9 (e.g., $K_D$ of 200 pM or higher).

As used herein, the term "vascular complication" refers to a vascular disorder or any damage to the blood vessels, such as damage to the blood vessel walls. Damage to the blood vessel walls may cause an increase in vascular permeability or leakage. The term "vascular permeability or leakage" refers to the capacity of the blood vessel walls to allow the flow of small molecules, proteins, and cells in and out of blood vessels. An increase in vascular permeability or leakage may be caused by an increase in the gaps (e.g., an increase in the size and/or number of the gaps) between endothelial cells that line the blood vessel walls and/or thinning of the blood vessel walls.

As used herein, the term "polypeptide" describes a single polymer in which the monomers are amino acid residues which are covalently conjugated together through amide bonds. A polypeptide is intended to encompass any amino acid sequence, either naturally occurring, recombinant, or synthetically produced.

As used herein, the term "homodimer" refers to a molecular construct formed by two identical macromolecules, such as proteins or nucleic acids. The two identical monomers may form a homodimer by covalent bonds or non-covalent bonds. For example, an Fc domain may be a homodimer of two Fc domain monomers if the two Fc domain monomers contain the same sequence. In another example, a polypeptide described herein including an extracellular ActRIIa variant fused to an Fc domain monomer may form a homodimer through the interaction of two Fc domain monomers, which form an Fc domain in the homodimer.

As used herein, the term "heterodimer" refers to a molecular construct formed by two different macromolecules, such as proteins or nucleic acids. The two monomers may form a heterodimer by covalent bonds or non-covalent bonds. For example, a polypeptide described herein including an extracellular ActRIIa variant fused to an Fc domain monomer may form a heterodimer through the interaction of two Fc domain monomers, each fused to a different ActRIIa variant, which form an Fc domain in the heterodimer.

As used herein, the term "host cell" refers to a vehicle that includes the necessary cellular components, e.g., organelles, needed to express proteins from their corresponding nucleic acids. The nucleic acids are typically included in nucleic acid vectors that can be introduced into the host cell by conventional techniques known in the art (transformation, transfection, electroporation, calcium phosphate precipitation, direct microinjection, etc.). A host cell may be a prokaryotic cell, e.g., a bacterial cell, or a eukaryotic cell, e.g., a mammalian cell (e.g., a CHO cell or a HEK293 cell).

As used herein, the term "therapeutically effective amount" refers an amount of a polypeptide, nucleic acid, or vector of the invention or a pharmaceutical composition containing a polypeptide, nucleic acid, or vector of the invention effective in achieving the desired therapeutic effect in treating a patient having a disease, such as a muscle disease, or a condition involving weakness and atrophy of muscles, e.g., Duchenne muscular dystrophy (DMD), lacioscapulohumeral muscular dystrophy (FSHD), inclusion body myositis (IBM), amyotrophic lateral sclerosis (ALS), sarcopenia, or cancer cachexia. The term "therapeutically effective amount" also refers an amount of a polypeptide, nucleic acid, or vector of the invention or a pharmaceutical composition containing a polypeptide, nucleic acid, or vector of the invention effective in achieving the desired therapeutic effect in treating a patient having a disease, such as a metabolic disease, or a condition involving excess body weight, excess body fat, high blood glucose, high fasting insulin levels, or insulin resistance, e.g., obesity, Type-1 diabetes, or Type-2 diabetes. In particular, the therapeutically effective amount of the polypeptide, nucleic acid, or vector avoids adverse side effects.

As used herein, the term "pharmaceutical composition" refers to a medicinal or pharmaceutical formulation that includes an active ingredient as well as excipients and diluents to enable the active ingredient suitable for the method of administration. The pharmaceutical composition of the present invention includes pharmaceutically acceptable components that are compatible with the polypeptide, nucleic acid, or vector. The pharmaceutical composition may be in tablet or capsule form for oral administration or in aqueous form for intravenous or subcutaneous administration.

As used herein, the term "pharmaceutically acceptable carrier or excipient" refers to an excipient or diluent in a pharmaceutical composition. The pharmaceutically acceptable carrier must be compatible with the other ingredients of the formulation and not deleterious to the recipient. In the present invention, the pharmaceutically acceptable carrier or excipient must provide adequate pharmaceutical stability to the polypeptide including an extracellular ActRIIa variant, the nucleic acid molecule(s) encoding the polypeptide, or a vector containing such nucleic acid molecule(s). The nature of the carrier or excipient differs with the mode of administration. For example, for intravenous administration, an aqueous solution carrier is generally used; for oral administration, a solid carrier is preferred.

As used herein, the term "treating and/or preventing" refers to the treatment and/or prevention of a disease, e.g., a metabolic disease (e.g., obesity, Type1 and Type-2 diabetes) or a muscle disease (e.g., DMD, FSHD, IBM, and ALS), using methods and compositions of the invention. Generally, treating a metabolic or muscle disease occurs after a subject has developed the metabolic or muscle disease and/or is already diagnosed with the metabolic or muscle disease. Preventing a metabolic or muscle disease refers to steps or procedures taken when a subject is at risk of developing the metabolic or muscle disease. The subject may show signs or mild symptoms that are judged by a physician to be indications or risk factors for developing the metabolic or muscle disease or have a family history or genetic predisposition of developing the metabolic or muscle disease, but has not yet developed the disease.

As used herein, the term "subject" refers to a mammal, e.g., preferably a human. Mammals include, but are not limited to, humans and domestic and farm animals, such as monkeys (e.g., a cynomolgus monkey), mice, dogs, cats, horses, and cows, etc.

DESCRIPTION OF THE DRAWINGS

Figure 1:
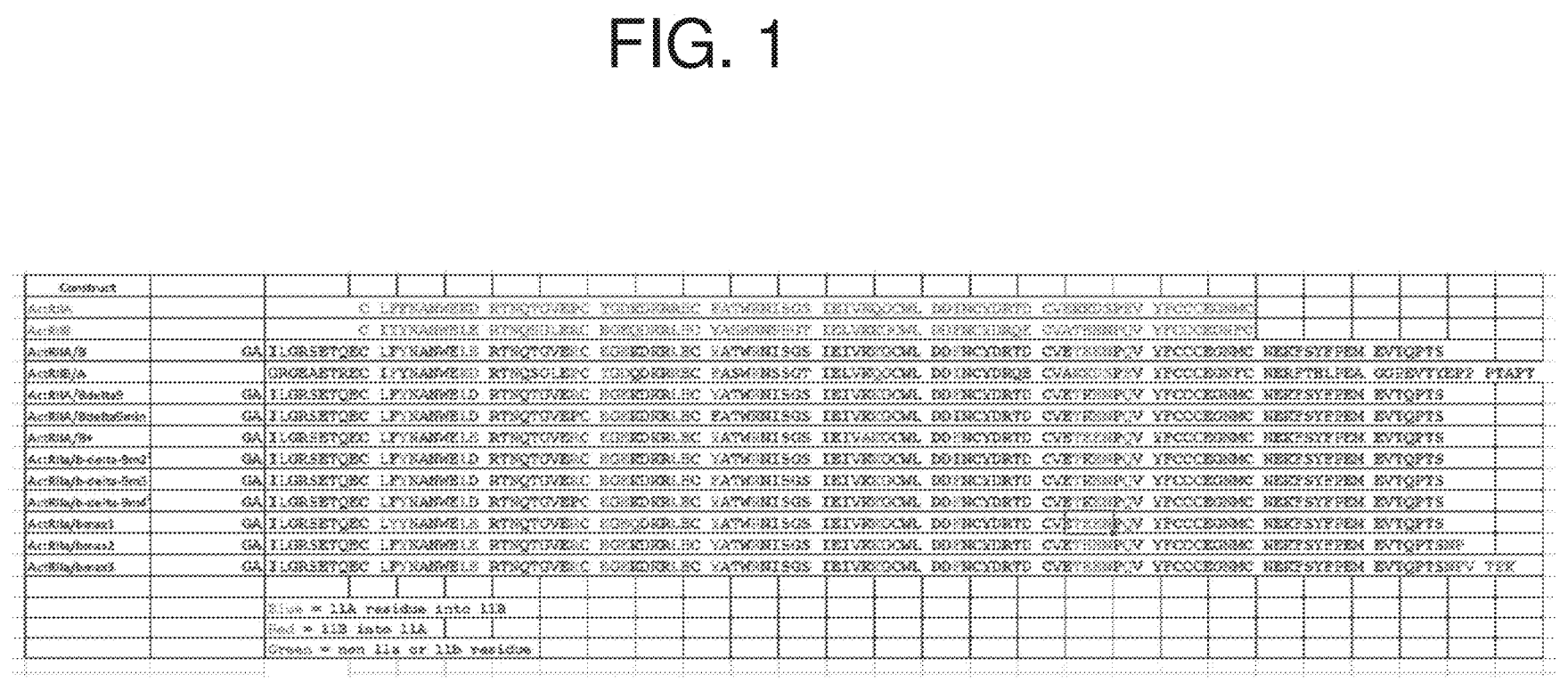

FIG. 1 is a sequence alignment showing the wild-type sequences of extracellular ActRIIa and ActRIIb and the amino acid substitutions in ActRIIa variants.

DETAILED DESCRIPTION OF THE INVENTION

Figure 2B:
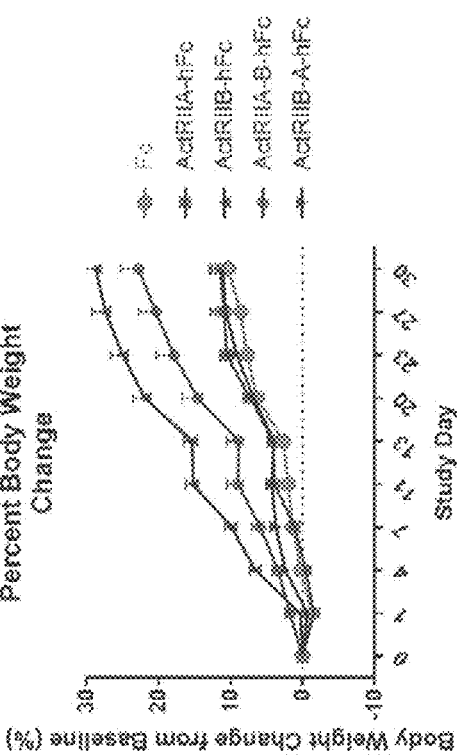
FIGS. 2A and 2B are scatter plots showing the effects of extracellular ActRIIa variants on body weight. Mice received a single hydrodynamic injection of a plasmid construct encoding the indicated ActRIIa variant or a control plasmid.

The invention features polypeptides that include an extracellular activin receptor type IIa (ActRIIa) variant. In some embodiments, a polypeptide of the invention includes an extracellular ActRIIa variant fused to a moiety (e.g., Fc domain monomer, a wild-type Fc domain, an Fc domain with amino acid substitutions (e.g., one or more substitutions that reduce dimerization), an albumin-binding peptide, a fibronectin domain, or a human serum albumin). A polypeptide including an extracellular ActRIIa variant fused to an Fc domain monomer may also form a dimer (e.g., homodimer or heterodimer) through the interaction between two Fc domain monomers. The ActRIIa variants described herein have weak binding affinity or no binding affinity to bone morphogenetic protein 9 (BMP9) compared to activins and myostatin. The invention also includes methods of treating diseases and conditions involving weakness and atrophy of muscles by increasing muscle mass and strength, methods of treating or preventing metabolic diseases, or methods of affecting myostatin, activin, and/or BMP9 signaling in a subject by administering to the subject a polypeptide including an extracellular ActRIIa variant described herein.

I. Extracellular Activin Receptor Type IIa (ActRIIa) Variants

Activin type II receptors are single transmembrane domain receptors that modulate signals for ligands in the transforming growth factor β (TGF-β) superfamily. Ligands in the TGF-β superfamily are involved in a host of physiological processes, such as muscle growth, vascular growth, cell differentiation, homeostasis, and osteogenesis. Examples of ligands in the TGF-β superfamily include, e.g., activin, inhibin, growth differentiation factors (GDFs) (e.g., GDF8, also known as myostatin), and bone morphogenetic proteins (BMPs) (e.g., BMP9). Myostatin and activins are known to play a role in the regulation of skeletal muscle growth. For example, mice without myostatin show a large increase in skeletal muscle mass.

Activins are also highly expressed in adipose tissue, and increased myostatin levels and activin receptor levels have been observed in subcutaneous and visceral fat of obese mice. Additionally, myostatin has been shown to be elevated in skeletal muscle and plasma of obese and insulin resistant women, and both type I and type II activin receptors have been linked to pancreatic function and diabetes. These data suggest that increased signaling through activin receptors, either due to increased expression of activin ligands (e.g., activin, myostatin) or increased expression of activin receptors themselves, could lead to obesity and metabolic disorders, such as Type-1 and Type-2 diabetes. Methods that reduce or inhibit this signaling could, therefore, be used in the treatment of obesity and metabolic disorders.

There exist two types of activin type II receptors: ActRIIa and ActRIIb. Studies have shown that BMP9 binds ActRIIb with about 300-fold higher binding affinity than ActRIIa (see, e.g., Townson et al., *J. Biol. Chem.* 287:27313, 2012). ActRIIa is known to have a longer half-life compared to ActRIIb. The present invention describes extracellular ActRIIa variants that are constructed by introducing amino acid residues of ActRIIb to ActRIIa, with the goal of imparting physiological properties conferred by ActRIIb, while also maintaining beneficial physiological and pharmacokinetic properties of ActAIIa. The optimum peptides confer significant increases in muscle mass, while retaining longer serum hall-life and low binding-affinity to BMP9, for example. The preferred ActRIIa variants also exhibit improved binding to activins and/or myostatin compared to wild-type ActRIIa, which allows them to compete with endogenous activin receptors for ligand binding and reduce or inhibit endogenous activin receptor signaling. These variants can be used to treat disorders in which activin receptor signaling is elevated, such as metabolic disorders, leading to a reduction in body fat, body weight, or insulin resistance (e.g., an increase in insulin sensitivity). In some embodiments, amino acid substitutions may be introduced to an extracellular ActRIIa variant to reduce or remove the binding affinity of the variant to BMP9. The wild-type amino acid sequences of the extracellular portions of human ActRIIa and ActRIIb are shown below.

```
Human ActRIIa, extracellular portion (SEQ ID NO:
73):
GAILGRSETQECLFFNANWEKDRTNQTGVEPCYGDKDKRRHCFATWKNI
SGSIEIVKQGCWLDDINCYDRTDCVEKKDSPEVYFCCCEGNMCNEKFSY
FPEMEVTQPTS Human ActRIIb, extracellular portion (SEQ ID NO:
74):
GRGEAETRECIYYNANWELERTNQSGLERCEGEQDKRLHCYASWRNSSG
TIELVKKGCWLDDFNCYDRQECVATEENPQVYFCCCEGNFCNERFTHLP
EAGGPEVTYEPPPTAPT
```

Polypeptides described herein include an extracellular ActAIIa variant having at least one amino acid substitution relative to the wild-type extracellular ActRIIa having the sequence of SEQ ID NO: 73 or the extracellular ActRIIa having any one of the sequences of SEQ ID NOs: 76-96. Possible amino acid substitutions at 27 different positions may be introduced to an extracellular ActRIIa variant (Table 1). In some embodiments, an extracellular ActAIIa variant may have at least 85% (e.g., at least 85%, 87%, 90%, 92%, 95%, 97%, or greater) amino acid sequence identity to the sequence of a wild-type extracellular ActRIIa (SEQ ID NO: 73). An extracellular ActRIIa variant may have one or more (e.g., 1-27, 1-25, 1-23, 1-21, 1-19, 1-17, 1-15, 1-13, 1-11, 1-9, 1-7, 1-5, 1-3, or 1-2; e.g., 1, 2, 3, 4, 5, 6, 7, 8, 9, 10, 11, 12, 13, 14, 15, 16, 17, 18, 19, 20, 21, 22, 23, 24, 25, 26, or 27) amino acid substitutions relative the sequence of a wild-type extracellular ActRIIa (SEQ ID NO: 73). In some embodiments, an extracellular ActRIIa variant (e.g., an extracellular ActRIIa variant having a sequence of SEQ ID NO: 1) may include amino acid substitutions at all of the 27 positions as listed in Table 1. In some embodiments, an extracellular ActRIIa variant may include amino acid substitutions at a number of positions, e.g., at 2, 4, 6, 8, 10, 12, 14, 16, 18, 20, 22, 24, or 26 out of the 27 positions, as listed in Table 1.

Amino acid substitutions can worsen or improve the activity and/or binding affinity of the ActRIIa variants of the invention. To maintain polypeptide function, it is important that the lysine (K) at position $X_{17}$ in the sequences shown in Tables 1 and 2 (SEQ ID NOs: 1-72 (e.g., SEQ ID NOs: 6-72) be retained. Substitutions at that position can lead to a loss of activity. For example, an ActRIIa variant having the sequence GAILGRSETQECLFYNANWEL-ERTNQTGVERCEGEKDKRLHCYATWRNISGSIEI-VAKGCWLDDENCYD RTDCVETEENPQVYFCC-CEGNMCNEKFSYFPEMEVTQPTS (SEQ ID NO: 150) has reduced activity in vivo, indicating that the substitution of alanine (A) for lysine (K) at $X_{17}$ is not tolerated. ActAIIa variants of the invention, including variants in Tables 1 and 2 (e.g., SEQ ID NOs: 1-72 (e.g., SEQ ID NOs: 6-72), therefore, retain amino acid K at position $X_{17}$.

The ActAIIa variants of the invention preferably have reduced, weak, or no substantial binding to BMP9. BMP9 binding is reduced in ActRIIa variants containing the amino acid sequence TEEN at positions $X_{23}$, $X_{24}$, $X_{25}$, and $X_{26}$, as well as in variants that maintain the amino acid K at position X24 and have the amino acid sequence TKEN at positions $X_{23}$, $X_{24}$, $X_{25}$, and $X_{26}$. The sequences TEEN and TKEN can be employed interchangeably in the ActRIIa variants (e.g., the variants in Tables 1 and 2, e.g., SEQ ID NOs: 1-72 (e.g., SEQ ID NOs: 6-72) of the invention to provide reduced BMP9 binding.

The ActRIIa variants of the invention may further include a C-terminal extension (e.g., additional amino acids at the C-terminus). The C-terminal extension can add one to six additional amino acids at the C-terminus (e.g., 1, 2, 3, 4, 5, 6 or more additional amino acids) to any of the variants shown in Tables 1 and 2 (e.g., SEQ ID NOs: 1-70 (e.g., SEQ ID NOs: 6-70)). One potential C-terminal extension that can be included in the ActRIIa variants of the invention is amino acid sequence NP. For example, the sequence including the C-terminal extension is SEQ ID NO: 71 (e.g., SEQ ID NO: 69 with a C-terminal extension of NP). Another exemplary C-terminal extension that can be included in the ActRIIa variants of the invention is amino acid sequence NPVTPK (SEQ ID NO: 155). For example, the sequence including the C-terminal extension is SEQ ID NO: 72 (e.g., SEQ ID NO: 69 with a C-terminal extension of NPVTPK).

TABLE 1

Amino acid substitutions in an extracellular ActRIIa variant having
a sequence of any one of SEQ ID NOs: 1-5

GAILGRSETQECLX$_1$X$_2$NANWX$_3$X$_4$X$_5$X$_6$TNQTGVEX$_7$CX$_8$GX$_9$X$_{10}$X$_{11}$X$_{12}$X$_{13}$X$_{14}$HCX$_{15}$ATWX$_{16}$NISGSIEIV
X$_{17}$X$_{18}$GCX$_{19}$X$_{20}$X$_{21}$DX$_{22}$NCYDRTDCVEX$_{23}$X$_{24}$X$_{25}$X$_{26}$PX$_{27}$VYFCCCEGNMCNEKFSYFPEMEVTQPTS
(SEQ ID NO: 1)

GAILGRSETQECLFX$_2$NANWX$_3$X$_4$X$_5$X$_6$TNQTGVEX$_7$CX$_8$GX$_9$KX$_{11}$X$_{12}$X$_{13}$X$_{14}$HCX$_{15}$ATWX$_{16}$NISGSIEIVX$_{17}$
X$_{18}$GCX$_{19}$X$_{20}$X$_{21}$DX$_{22}$NCYDRTDCVEX$_{23}$X$_{24}$X$_{25}$X$_{26}$PX$_{27}$VYFCCCEGNMCNEKFSYFPEMEVTQPTS
(SEQ ID NO: 2)

GAILGRSETQECLFX$_2$NANWEX$_4$X$_5$RTNQTGVEX$_7$CX$_8$GX$_9$KDKRX$_{14}$HCX$_{15}$ATWX$_{16}$NISGSIEIVKX$_{18}$GC
WLDDX$_{22}$NCYDRTDCVEX$_{23}$X$_{24}$X$_{25}$X$_{26}$PX$_{27}$VYFCCCEGNMCNEKFSYFPEMEVTQPTS (SEQ ID NO: 3)

GAILGRSETQECLFX$_2$NANWEX$_4$DRTNQTGVEX$_7$CX$_8$GX$_9$KDKRX$_{14}$HCX$_{15}$ATWX$_{16}$NISGSIEIVKX$_{18}$GC
WLDDX$_{22}$NCYDRTDCVEX$_{23}$KX$_{25}$X$_{26}$PX$_{27}$VYFCCCEGNMCNEKFSYFPEMEVTQPTS (SEQ ID NO: 4)

GAILGRSETQECLFX$_2$NANWEX$_4$DRTNQTGVEPCX$_8$GX$_9$KDKRX$_{14}$HCFATWKNISGSIEIVKX$_{18}$GCWLD
DINCYDRTDCVEX$_{23}$KX$_{25}$X$_{26}$PX$_{27}$VYFCCCEGNMCNEKFSYFPEMEVTQPTS (SEQ ID NO: 5)

| | | | |
|---|---|---|---|
| X$_1$ | F or Y | X$_{15}$ | F or Y |
| X$_2$ | F or Y | X$_{16}$ | K, R, or A |
| X$_3$ | E or A | X$_{17}$ | K, A, Y, F, or I |
| X$_4$ | K or L | X$_{18}$ | Q or K |
| X$_5$ | D or E | X$_{19}$ | W or A |
| X$_6$ | R or A | X$_{20}$ | L or A |
| X$_7$ | P or R | X$_{21}$ | D, K, R, A, F, G, M, N, or I |
| X$_8$ | Y or E | X$_{22}$ | I, F, or A |
| X$_9$ | D or E | X$_{23}$ | K or T |
| X$_{10}$ | K or Q | X$_{24}$ | K or E |
| X$_{11}$ | D or A | X$_{25}$ | D or E |
| X$_{12}$ | K or A | X$_{26}$ | S or N |

GAILGRSETQECLX$_1$X$_2$NANWX$_3$X$_4$X$_5$X$_6$TNQTGVEX$_7$CX$_8$GX$_9$X$_{10}$X$_{11}$X$_{12}$X$_{13}$X$_{14}$HCX$_{15}$ATWX$_{16}$NISGSIEIV
X$_{17}$X$_{18}$GCX$_{19}$X$_{20}$X$_{21}$DX$_{22}$NCYDRTDCVEX$_{23}$X$_{24}$X$_{25}$X$_{26}$PX$_{27}$VYFCCCEGNMCNEKFSYFPEMEVTQPTS
(SEQ ID NO: 1)

GAILGRSETQECLFX$_2$NANWX$_3$X$_4$X$_5$X$_6$TNQTGVEX$_7$CX$_8$GX$_9$KX$_{11}$X$_{12}$X$_{13}$X$_{14}$HCX$_{15}$ATWX$_{16}$NISGSIEIVX$_{17}$
X$_{18}$GCX$_{19}$X$_{20}$X$_{21}$DX$_{22}$NCYDRTDCVEX$_{23}$X$_{24}$X$_{25}$X$_{26}$PX$_{27}$VYFCCCEGNMCNEKFSYFPEMEVTQPTS
(SEQ ID NO: 2)

GAILGRSETQECLFX$_2$NANWEX$_4$X$_5$RTNQTGVEX$_7$CX$_8$GX$_9$KDKRX$_{14}$HCX$_{15}$ATWX$_{16}$NISGSIEIVKX$_{18}$GC
WLDDX$_{22}$NCYDRTDCVEX$_{23}$X$_{24}$X$_{25}$X$_{26}$PX$_{27}$VYFCCCEGNMCNEKFSYFPEMEVTQPTS (SEQ ID NO: 3)

GAILGRSETQECLFX$_2$NANWEX$_4$DRTNQTGVEX$_7$CX$_8$GX$_9$KDKRX$_{14}$HCX$_{15}$ATWX$_{16}$NISGSIEIVKX$_{18}$GC
WLDDX$_{22}$NCYDRTDCVEX$_{23}$KX$_{25}$X$_{26}$PX$_{27}$VYFCCCEGNMCNEKFSYFPEMEVTQPTS (SEQ ID NO: 4)

GAILGRSETQECLFX$_2$NANWEX$_4$DRTNQTGVEPCX$_8$GX$_9$KDKRX$_{14}$HCFATWKNISGSIEIVKX$_{18}$GCWLD
DINCYDRTDCVEX$_{23}$KX$_{25}$X$_{26}$PX$_{27}$VYFCCCEGNMCNEKFSYFPEMEVTQPTS (SEQ ID NO: 5)

| | | | |
|---|---|---|---|
| X$_{13}$ | R or A | X$_{27}$ | E or Q |
| X$_{14}$ | R or L | | |

In some embodiments of the extracellular ActRIIa variant having the sequence of SEQ ID NO: 2, $X_3$ is E, $X_6$ is R, Xu is D, $X_{12}$ is K, $X_{13}$ is R, $X_{16}$ is K or R, $X_{17}$ is K, X is W, $X_{20}$ is L, $X_{21}$ is D, and $X_{22}$ is I or F. In some embodiments of the extracellular ActRIIa variant having the sequence of SEQ ID NO: 1 or 2, $X_{17}$ is K. In some embodiments of the extracellular ActRIIa variant having the sequence of SEQ ID NOs: 1-3, $X_{17}$ is K, $X_{23}$ is T, $X_{24}$ is E, $X_{25}$ is E, and $X_{26}$ is N. In some embodiments of the extracellular ActRIIa variant having the sequence of any one of SEQ ID NOs: 1-5, $X_{17}$ is K, $X_{23}$ is T, $X_{24}$ is K, $X_{25}$ is E, and $X_{26}$ is N.

In some embodiments, a polypeptide described herein includes an extracellular ActRIIa variant having a sequence of any one of SEQ ID NOs: 6-72 (Table 2).

TABLE 2

Extracellular ActRIIa variants having the sequences of SEQ ID NOs: 6-72

| SEQ ID NO | Amino Acid Sequence |
|---|---|
| 6 | GAILGRSETQECLFYNANWELDRTNQTGVEPCEGEKDKRLHCFATWKNISGSIEIV KKGCWLDDINCYDRTDCVETKENPQVYFCCCEGNMCNEKFSYFPEMEVTQPTS |
| 7 | GAILGRSETQECLFYNANWELERTNQTGVEPCEGEKDKRLHCFATWKNISGSIEIV KKGCWLDDINCYDRTDCVETKENPQVYFCCCEGNMCNEKFSYFPEMEVTQPTS |
| 8 | GAILGRSETQECLFYNANWELDRTNQTGVERCEGEKDKRLHCFATWKNISGSIEIV KKGCWLDDINCYDRTDCVETKENPQVYFCCCEGNMCNEKFSYFPEMEVTQPTS |
| 9 | GAILGRSETQECLFYNANWELDRTNQTGVEPCEGEKDKRLHCYATWKNISGSIEIV KKGCWLDDINCYDRTDCVETKENPQVYFCCCEGNMCNEKFSYFPEMEVTQPTS |
| 10 | GAILGRSETQECLFYNANWELDRTNQTGVEPCEGEKDKRLHCFATWRNISGSIEIV KKGCWLDDINCYDRTDCVETKENPQVYFCCCEGNMCNEKFSYFPEMEVTQPTS |
| 11 | GAILGRSETQECLFYNANWELDRTNQTGVEPCEGEKDKRLHCFATWKNISGSIEIV KKGCWLDDFNCYDRTDCVETKENPQVYFCCCEGNMCNEKFSYFPEMEVTQPTS |
| 12 | GAILGRSETQECLFYNANWELDRTNQTGVEPCEGEKDKRLHCFATWKNISGSIEIV KKGCWLDDINCYDRTDCVETEENPQVYFCCCEGNMCNEKFSYFPEMEVTQPTS |
| 13 | GAILGRSETQECLFYNANWELERTNQTGVERCEGEKDKRLHCFATWKNISGSIEIV KKGCWLDDINCYDRTDCVETKENPQVYFCCCEGNMCNEKFSYFPEMEVTQPTS |
| 14 | GAILGRSETQECLFYNANWELERTNQTGVEPCEGEKDKRLHCYATWKNISGSIEIV KKGCWLDDINCYDRTDCVETKENPQVYFCCCEGNMCNEKFSYFPEMEVTQPTS |
| 15 | GAILGRSETQECLFYNANWELERTNQTGVEPCEGEKDKRLHCFATWRNISGSIEIV KKGCWLDDINCYDRTDCVETKENPQVYFCCCEGNMCNEKFSYFPEMEVTQPTS |
| 16 | GAILGRSETQECLFYNANWELERTNQTGVEPCEGEKDKRLHCFATWKNISGSIEIV KKGCWLDDFNCYDRTDCVETKENPQVYFCCCEGNMCNEKFSYFPEMEVTQPTS |
| 17 | GAILGRSETQECLFYNANWELERTNQTGVEPCEGEKDKRLHCFATWKNISGSIEIV KKGCWLDDINCYDRTDCVETEENPQVYFCCCEGNMCNEKFSYFPEMEVTQPTS |
| 18 | GAILGRSETQECLFYNANWELDRTNQTGVERCEGEKDKRLHCYATWKNISGSIEIV KKGCWLDDINCYDRTDCVETKENPQVYFCCCEGNMCNEKFSYFPEMEVTQPTS |
| 19 | GAILGRSETQECLFYNANWELDRTNQTGVERCEGEKDKRLHCFATWRNISGSIEIV KKGCWLDDINCYDRTDCVETKENPQVYFCCCEGNMCNEKFSYFPEMEVTQPTS |
| 20 | GAILGRSETQECLFYNANWELDRTNQTGVERCEGEKDKRLHCFATWKNISGSIEIV KKGCWLDDFNCYDRTDCVETKENPQVYFCCCEGNMCNEKFSYFPEMEVTQPTS |
| 21 | GAILGRSETQECLFYNANWELDRTNQTGVERCEGEKDKRLHCFATWKNISGSIEIV KKGCWLDDINCYDRTDCVETEENPQVYFCCCEGNMCNEKFSYFPEMEVTQPTS |
| 22 | GAILGRSETQECLFYNANWELDRTNQTGVEPCEGEKDKRLHCYATWRNISGSIEIV KKGCWLDDINCYDRTDCVETKENPQVYFCCCEGNMCNEKFSYFPEMEVTQPTS |
| 23 | GAILGRSETQECLFYNANWELDRTNQTGVEPCEGEKDKRLHCYATWKNISGSIEIV KKGCWLDDFNCYDRTDCVETKENPQVYFCCCEGNMCNEKFSYFPEMEVTQPTS |
| 24 | GAILGRSETQECLFYNANWELDRTNQTGVEPCEGEKDKRLHCYATWKNISGSIEIV KKGCWLDDINCYDRTDCVETEENPQVYFCCCEGNMCNEKFSYFPEMEVTQPTS |
| 25 | GAILGRSETQECLFYNANWELDRTNQTGVEPCEGEKDKRLHCFATWRNISGSIEIV KKGCWLDDFNCYDRTDCVETKENPQVYFCCCEGNMCNEKFSYFPEMEVTQPTS |
| 26 | GAILGRSETQECLFYNANWELDRTNQTGVEPCEGEKDKRLHCFATWRNISGSIEIV KKGCWLDDINCYDRTDCVETEENPQVYFCCCEGNMCNEKFSYFPEMEVTQPTS |
| 27 | GAILGRSETQECLFYNANWELDRTNQTGVEPCEGEKDKRLHCFATWKNISGSIEIV KKGCWLDDFNCYDRTDCVETEENPQVYFCCCEGNMCNEKFSYFPEMEVTQPTS |

TABLE 2-continued

Extracellular ActRIIa variants having the sequences of SEQ ID NOs: 6-72

| SEQ ID NO | Amino Acid Sequence |
|---|---|
| 28 | GAILGRSETQECLFYNANWELERTNQTGVERCEGEKDKRLHCYATWKNISGSIEIV<br>KKGCWLDDINCYDRTDCVETKENPQVYFCCCEGNMCNEKFSYFPEMEVTQPTS |
| 29 | GAILGRSETQECLFYNANWELERTNQTGVERCEGEKDKRLHCFATWRNISGSIEIV<br>KKGCWLDDINCYDRTDCVETKENPQVYFCCCEGNMCNEKFSYFPEMEVTQPTS |
| 30 | GAILGRSETQECLFYNANWELERTNQTGVERCEGEKDKRLHCFATWKNISGSIEIV<br>KKGCWLDDFNCYDRTDCVETKENPQVYFCCCEGNMCNEKFSYFPEMEVTQPTS |
| 31 | GAILGRSETQECLFYNANWELERTNQTGVERCEGEKDKRLHCFATWKNISGSIEIV<br>KKGCWLDDINCYDRTDCVETEENPQVYFCCCEGNMCNEKFSYFPEMEVTQPTS |
| 32 | GAILGRSETQECLFYNANWELERTNQTGVEPCEGEKDKRLHCYATWRNISGSIEIV<br>KKGCWLDDINCYDRTDCVETKENPQVYFCCCEGNMCNEKFSYFPEMEVTQPTS |
| 33 | GAILGRSETQECLFYNANWELERTNQTGVEPCEGEKDKRLHCYATWKNISGSIEIV<br>KKGCWLDDFNCYDRTDCVETKENPQVYFCCCEGNMCNEKFSYFPEMEVTQPTS |
| 34 | GAILGRSETQECLFYNANWELERTNQTGVEPCEGEKDKRLHCYATWKNISGSIEIV<br>KKGCWLDDINCYDRTDCVETEENPQVYFCCCEGNMCNEKFSYFPEMEVTQPTS |
| 35 | GAILGRSETQECLFYNANWELERTNQTGVEPCEGEKDKRLHCFATWRNISGSIEIV<br>KKGCWLDDFNCYDRTDCVETKENPQVYFCCCEGNMCNEKFSYFPEMEVTQPTS |
| 36 | GAILGRSETQECLFYNANWELERTNQTGVEPCEGEKDKRLHCFATWRNISGSIEIV<br>KKGCWLDDINCYDRTDCVETEENPQVYFCCCEGNMCNEKFSYFPEMEVTQPTS |
| 37 | GAILGRSETQECLFYNANWELERTNQTGVEPCEGEKDKRLHCFATWKNISGSIEIV<br>KKGCWLDDFNCYDRTDCVETEENPQVYFCCCEGNMCNEKFSYFPEMEVTQPTS |
| 38 | GAILGRSETQECLFYNANWELDRTNQTGVERCEGEKDKRLHCYATWRNISGSIEIV<br>KKGCWLDDINCYDRTDCVETKENPQVYFCCCEGNMCNEKFSYFPEMEVTQPTS |
| 39 | GAILGRSETQECLFYNANWELDRTNQTGVERCEGEKDKRLHCYATWKNISGSIEIV<br>KKGCWLDDFNCYDRTDCVETKENPQVYFCCCEGNMCNEKFSYFPEMEVTQPTS |
| 40 | GAILGRSETQECLFYNANWELDRTNQTGVERCEGEKDKRLHCYATWKNISGSIEIV<br>KKGCWLDDINCYDRTDCVETEENPQVYFCCCEGNMCNEKFSYFPEMEVTQPTS |
| 41 | GAILGRSETQECLFYNANWELDRTNQTGVERCEGEKDKRLHCFATWRNISGSIEIV<br>KKGCWLDDFNCYDRTDCVETKENPQVYFCCCEGNMCNEKFSYFPEMEVTQPTS |
| 42 | GAILGRSETQECLFYNANWELDRTNQTGVERCEGEKDKRLHCFATWRNISGSIEIV<br>KKGCWLDDINCYDRTDCVETEENPQVYFCCCEGNMCNEKFSYFPEMEVTQPTS |
| 43 | GAILGRSETQECLFYNANWELDRTNQTGVERCEGEKDKRLHCFATWKNISGSIEIV<br>KKGC<br>WLDDFNCYDRTDCVETEENPQVYFCCCEGNMCNEKFSYFPEMEVTQPTS |
| 44 | GAILGRSETQECLFYNANWELDRTNQTGVEPCEGEKDKRLHCYATWRNISGSIEIV<br>KKGCWLDDFNCYDRTDCVETKENPQVYFCCCEGNMCNEKFSYFPEMEVTQPTS |
| 45 | GAILGRSETQECLFYNANWELDRTNQTGVEPCEGEKDKRLHCYATWRNISGSIEIV<br>KKGCWLDDINCYDRTDCVETEENPQVYFCCCEGNMCNEKFSYFPEMEVTQPTS |
| 46 | GAILGRSETQECLFYNANWELDRTNQTGVEPCEGEKDKRLHCYATWKNISGSIEIV<br>KKGCWLDDFNCYDRTDCVETEENPQVYFCCCEGNMCNEKFSYFPEMEVTQPTS |
| 47 | GAILGRSETQECLFYNANWELDRTNQTGVEPCEGEKDKRLHCFATWRNISGSIEIV<br>KKGCWLDDFNCYDRTDCVETEENPQVYFCCCEGNMCNEKFSYFPEMEVTQPTS |
| 48 | GAILGRSETQECLFYNANWELERTNQTGVERCEGEKDKRLHCYATWRNISGSIEIV<br>KKGCWLDDINCYDRTDCVETKENPQVYFCCCEGNMCNEKFSYFPEMEVTQPTS |
| 49 | GAILGRSETQECLFYNANWELERTNQTGVERCEGEKDKRLHCYATWKNISGSIEIV<br>KKGCWLDDFNCYDRTDCVETKENPQVYFCCCEGNMCNEKFSYFPEMEVTQPTS |
| 50 | GAILGRSETQECLFYNANWELERTNQTGVERCEGEKDKRLHCYATWKNISGSIEIV<br>KKGCWLDDINCYDRTDCVETEENPQVYFCCCEGNMCNEKFSYFPEMEVTQPTS |
| 51 | GAILGRSETQECLFYNANWELERTNQTGVERCEGEKDKRLHCFATWRNISGSIEIV<br>KKGCWLDDFNCYDRTDCVETKENPQVYFCCCEGNMCNEKFSYFPEMEVTQPTS |
| 52 | GAILGRSETQECLFYNANWELERTNQTGVERCEGEKDKRLHCFATWRNISGSIEIV<br>KKGCWLDDINCYDRTDCVETEENPQVYFCCCEGNMCNEKFSYFPEMEVTQPTS |

TABLE 2-continued

| Extracellular ActRIIa variants having the sequences of SEQ ID NOs: 6-72 |
|---|

| SEQ ID NO | Amino Acid Sequence |
|---|---|
| 53 | GAILGRSETQECLFYNANWELERTNQTGVERCEGEKDKRLHCFATWKNISGSIEIV KKGCWLDDFNCYDRTDCVETEENPQVYFCCCEGNMCNEKFSYFPEMEVTQPTS |
| 54 | GAILGRSETQECLFYNANWELERTNQTGVEPCEGEKDKRLHCYATWRNISGSIEIV KKGCWLDDFNCYDRTDCVETKENPQVYFCCCEGNMCNEKFSYFPEMEVTQPTS |
| 55 | GAILGRSETQECLFYNANWELERTNQTGVEPCEGEKDKRLHCYATWRNISGSIEIV KKGCWLDDINCYDRTDCVETEENPQVYFCCCEGNMCNEKFSYFPEMEVTQPTS |
| 56 | GAILGRSETQECLFYNANWELERTNQTGVEPCEGEKDKRLHCYATWKNISGSIEIV KKGCWLDDFNCYDRTDCVETEENPQVYFCCCEGNMCNEKFSYFPEMEVTQPTS |
| 57 | GAILGRSETQECLFYNANWELERTNQTGVEPCEGEKDKRLHCFATWRNISGSIEIV KKGCWLDDFNCYDRTDCVETEENPQVYFCCCEGNMCNEKFSYFPEMEVTQPTS |
| 58 | GAILGRSETQECLFYNANWELDRTNQTGVERCEGEKDKRLHCYATWRNISGSIEIV KKGCWLDDFNCYDRTDCVETKENPQVYFCCCEGNMCNEKFSYFPEMEVTQPTS |
| 59 | GAILGRSETQECLFYNANWELDRTNQTGVERCEGEKDKRLHCYATWRNISGSIEIV KKGCWLDDINCYDRTDCVETEENPQVYFCCCEGNMCNEKFSYFPEMEVTQPTS |
| 60 | GAILGRSETQECLFYNANWELDRTNQTGVERCEGEKDKRLHCYATWKNISGSIEIV KKGCWLDDFNCYDRTDCVETEENPQVYFCCCEGNMCNEKFSYFPEMEVTQPTS |
| 61 | GAILGRSETQECLFYNANWELDRTNQTGVERCEGEKDKRLHCFATWRNISGSIEIV KKGCWLDDFNCYDRTDCVETEENPQVYFCCCEGNMCNEKFSYFPEMEVTQPTS |
| 62 | GAILGRSETQECLFYNANWELDRTNQTGVEPCEGEKDKRLHCYATWRNISGSIEIV KKGCWLDDFNCYDRTDCVETEENPQVYFCCCEGNMCNEKFSYFPEMEVTQPTS |
| 63 | GAILGRSETQECLFYNANWELERTNQTGVERCEGEKDKRLHCYATWRNISGSIEIV KKGCWLDDFNCYDRTDCVETKENPQVYFCCCEGNMCNEKFSYFPEMEVTQPTS |
| 64 | GAILGRSETQECLFYNANWELERTNQTGVERCEGEKDKRLHCYATWRNISGSIEIV KKGCWLDDINCYDRTDCVETEENPQVYFCCCEGNMCNEKFSYFPEMEVTQPTS |
| 65 | GAILGRSETQECLFYNANWELERTNQTGVERCEGEKDKRLHCYATWKNISGSIEIV KKGCWLDDFNCYDRTDCVETEENPQVYFCCCEGNMCNEKFSYFPEMEVTQPTS |
| 66 | GAILGRSETQECLFYNANWELERTNQTGVERCEGEKDKRLHCFATWRNISGSIEIV KKGCWLDDFNCYDRTDCVETEENPQVYFCCCEGNMCNEKFSYFPEMEVTQPTS |
| 67 | GAILGRSETQECLFYNANWELDRTNQTGVERCEGEKDKRLHCYATWRNISGSIEIV KKGCWLDDFNCYDRTDCVETEENPQVYFCCCEGNMCNEKFSYFPEMEVTQPTS |
| 68 | GAILGRSETQECLFYNANWELERTNQTGVEPCEGEKDKRLHCYATWRNISGSIEIV KKGCWLDDFNCYDRTDCVETEENPQVYFCCCEGNMCNEKFSYFPEMEVTQPTS |
| 69 | GAILGRSETQECLFYNANWELERTNQTGVERCEGEKDKRLHCYATWRNISGSIEIV KKGCWLDDFNCYDRTDCVETEENPQVYFCCCEGNMCNEKFSYFPEMEVTQPTS |
| 70 | GAILGRSETQECLYYNANWELERTNQTGVERCEGEQDKRLHCYATWRNISGSIEIV KKGCWLDDFNCYDRTDCVETEENPQVYFCCCEGNMCNEKFSYFPEMEVTQPTS |
| 71 | GAILGRSETQECLFYNANWELERTNQTGVERCEGEKDKRLHCYATWRNISGSIEIV KKGCWLDDFNCYDRTDCVETEENPQVYFCCCEGNMCNEKFSYFPEMEVTQPTSN P |
| 72 | GAILGRSETQECLFYNANWELERTNQTGVERCEGEKDKRLHCYATWRNISGSIEIV KKGCWLDDFNCYDRTDCVETEENPQVYFCCCEGNMCNEKFSYFPEMEVTQPTSN PVTPK |

In some embodiments, a polypeptide of the invention including an extracellular ActRIIa variant (e.g., any one of SEQ ID NOs: 1-72 (e.g., SEQ ID NOs: 6-72) has amino acid K at position $X_{17}$. Altering the amino acid at position $X_{17}$ can result in reduced activity. For example, an ActRIIa variant having the sequence GAILGRSETQECL-FYNANWELERTNQTGVERCEGEKDKRLHCYA-TWRNISGSIEIVAKGCWLDDFNCYD RTDCVETEEN-PQVYFCCCEGNMCNEKFSYFPEMEVTQPTS (SEQ ID NO: 150) has reduced activity in vivo, indicating that the substitution of A for K at $X_{17}$ is not tolerated.

In some embodiments, a polypeptide of the invention including an extracellular ActRIIa variant (e.g., any one of SEQ ID NOs: 1-72 (e.g., SEQ ID NOs: 6-72) with the sequence TEEN at positions $X_{23}$, $X_{24}$, $X_{25}$, and $X_{26}$ can have a substitution of the amino acid K for the amino acid E at position $X_{24}$. In some embodiments, a polypeptide of the invention including an extracellular ActRIIa variant (e.g., any one of SEQ ID NOs: 1-72 (e.g., SEQ ID NOs: 6-72) with the sequence TKEN at positions $X_{23}$, $X_{24}$, $X_{25}$, and $X_{26}$ can have a substitution of the amino acid E for the amino acid K at position $X_{24}$. Polypeptides having the sequence TEEN or TKEN at positions $X_{23}$, $X_{24}$, $X_{25}$, and $X_{26}$ have reduced or weak binding to BMP9.

In some embodiments, a polypeptide of the invention including an extracellular ActRIIa variant (e.g., any one of SEQ ID NOs: 1-70 (e.g., SEQ ID NOs: 6-70)) may further include a C-terminal extension (e.g., additional amino acids at the C-terminus). In some embodiments, the C-terminal extension is amino acid sequence NP. For example, the sequence including the C-terminal extension is SEQ ID NO: 71 (e.g., SEQ ID NO: 69 with a C-terminal extension of NP). In some embodiments, the C-terminal extension is amino acid sequence NPVTPK (SEQ ID NO: 155). For example, the sequence including the C-terminal extension is SEQ ID NO: 72 (e.g., SEQ ID NO: 69 with a C-terminal extension of NPVTPK). The C-terminal extension can add one to six additional amino acids at the C-terminus (e.g., 1, 2, 3, 4, 5, 6 or more additional amino acids).

In some embodiments, a polypeptide of the invention including an extracellular ActRIIa variant may further include a moiety (e.g., Fc domain monomer, a wild-type Fc domain, an Fc domain with amino acid substitutions (e.g., one or more substitutions that reduce dimerization), an albumin-binding peptide, a fibronectin domain, or a human serum albumin), which may be fused to the N- or C-terminus (e.g., C-terminus) of the extracellular ActRIIa variant by way of a linker or other covalent bonds. A polypeptide including an extracellular ActRIIa variant fused to an Fc domain monomer may form a dimer (e.g., homodimer or heterodimer) through the interaction between two Fc domain monomers, which combine to form an Fc domain in the dimer.

In some embodiments, an extracellular ActAIIa variant described herein does not have the sequence of any one of SEQ ID NOs: 76-96 shown in Table 3 below.

TABLE 3

Excluded Extracellular ActRIIa Variants.

| SEQ ID NO | Amino Acid Sequence |
|---|---|
| 76 | GAILGRSETQECLFFNANWEKDRTNQTGVEPCYGDKDKRRHCFATWANISGSIEIV KQGCWLDDINCYDRTDCVEKKDSPEVYFCCCEGNMCNEKFSYFPEMEVTQPTS |
| 77 | GAILGRSETQECLFFNANWAKDRTNQTGVEPCYGDKDKRRHCFATWKNISGSIEIV KQGCWLDDINCYDRTDCVEKKDSPEVYFCCCEGNMCNEKFSYFPEMEVTQPTS |
| 78 | GAILGRSETQECLFFNANWEKDATNQTGVEPCYGDKDKRRHCFATWKNISGSIEIV KQGCWLDDINCYDRTDCVEKKDSPEVYFCCCEGNMCNEKFSYFPEMEVTQPTS |
| 79 | GAILGRSETQECLFFNANWEKDRTNQTGVEPCYGDKAKRRHCFATWKNISGSIEIV KQGCWLDDINCYDRTDCVEKKDSPEVYFCCCEGNMCNEKFSYFPEMEVTQPTS |
| 80 | GAILGRSETQECLFFNANWEKDRTNQTGVEPCYGDKDARRHCFATWKNISGSIEIV KQGCWLDDINCYDRTDCVEKKDSPEVYFCCCEGNMCNEKFSYFPEMEVTQPTS |
| 81 | GAILGRSETQECLFFNANWEKDRTNQTGVEPCYGDKDKARHCFATWKNISGSIEIV KQGCWLDDINCYDRTDCVEKKDSPEVYFCCCEGNMCNEKFSYFPEMEVTQPTS |
| 82 | GAILGRSETQECLFFNANWEKDRTNQTGVEPCYGDKDKRRHCFATWKNISGSIEIV AQGCWLDDINCYDRTDCVEKKDSPEVYFCCCEGNMCNEKFSYFPEMEVTQPTS |
| 83 | GAILGRSETQECLFFNANWEKDRTNQTGVEPCYGDKDKRRHCFATWKNISGSIEIV YQGCWLDDINCYDRTDCVEKKDSPEVYFCCCEGNMCNEKFSYFPEMEVTQPTS |
| 84 | GAILGRSETQECLFFNANWEKDRTNQTGVEPCYGDKDKRRHCFATWKNISGSIEIV FQGCWLDDINCYDRTDCVEKKDSPEVYFCCCEGNMCNEKFSYFPEMEVTQPTS |
| 85 | GAILGRSETQECLFFNANWEKDRTNQTGVEPCYGDKDKRRHCFATWKNISGSIEIVI QGCWLDDINCYDRTDCVEKKDSPEVYFCCCEGNMCNEKFSYFPEMEVTQPTS |
| 86 | GAILGRSETQECLFFNANWEKDRTNQTGVEPCYGDKDKRRHCFATWKNISGSIEIV KQGCALDDINCYDRTDCVEKKDSPEVYFCCCEGNMCNEKFSYFPEMEVTQPTS |
| 87 | GAILGRSETQECLFFNANWEKDRTNQTGVEPCYGDKDKRRHCFATWKNISGSIEIV KQGCWADDINCYDRTDCVEKKDSPEVYFCCCEGNMCNEKFSYFPEMEVTQPTS |
| 88 | GAILGRSETQECLFFNANWEKDRTNQTGVEPCYGDKDKRRHCFATWKNISGSIEIV KQGCWLKDINCYDRTDCVEKKDSPEVYFCCCEGNMCNEKFSYFPEMEVTQPTS |
| 89 | GAILGRSETQECLFFNANWEKDRTNQTGVEPCYGDKDKRRHCFATWKNISGSIEIV KQGCWLRDINCYDRTDCVEKKDSPEVYFCCCEGNMCNEKFSYFPEMEVTQPTS |
| 90 | GAILGRSETQECLFFNANWEKDRTNQTGVEPCYGDKDKRRHCFATWKNISGSIEIV KQGCWLADINCYDRTDCVEKKDSPEVYFCCCEGNMCNEKFSYFPEMEVTQPTS |
| 91 | GAILGRSETQECLFFNANWEKDRTNQTGVEPCYGDKDKRRHCFATWKNISGSIEIV KQGCWLFDINCYDRTDCVEKKDSPEVYFCCCEGNMCNEKFSYFPEMEVTQPTS |
| 92 | GAILGRSETQECLFFNANWEKDRTNQTGVEPCYGDKDKRRHCFATWKNISGSIEIV KQGCWLGDINCYDRTDCVEKKDSPEVYFCCCEGNMCNEKFSYFPEMEVTQPTS |
| 93 | GAILGRSETQECLFFNANWEKDRTNQTGVEPCYGDKDKRRHCFATWKNISGSIEIV KQGCWLMDINCYDRTDCVEKKDSPEVYFCCCEGNMCNEKFSYFPEMEVTQPTS |

TABLE 3-continued

Excluded Extracellular ActRIIa Variants.

| SEQ ID NO | Amino Acid Sequence |
|---|---|
| 94 | GAILGRSETQECLFFNANWEKDRTNQTGVEPCYGDKDKRRHCFATWKNISGSIEIV<br>KQGCWLNDINCYDRTDCVEKKDSPEVYFCCCEGNMCNEKFSYFPEMEVTQPTS |
| 95 | GAILGRSETQECLFFNANWEKDRTNQTGVEPCYGDKDKRRHCFATWKNISGSIEIV<br>KQGCWLIDINCYDRTDCVEKKDSPEVYFCCCEGNMCNEKFSYFPEMEVTQPTS |
| 96 | GAILGRSETQECLFFNANWEKDRTNQTGVEPCYGDKDKRRHCFATWKNISGSIEIV<br>KQGCWLDDANCYDRTDCVEKKDSPEVYFCCCEGNMCNEKFSYFPEMEVTQPTS |

Furthermore, in some embodiments, a polypeptide described herein has a serum half-life of at least 7 days in humans. The polypeptide may bind to bone morphogenetic protein 9 (BMP9) with a $K_D$ of 200 pM or higher. The polypeptide may bind to activin A with a $K_D$ of 10 pM or higher. In some embodiments, the polypeptide does not bind to BMP9 or activin A. In some embodiments, the polypeptide binds to activin and/or myostatin and exhibits reduced (e.g., weak) binding to BMP9. In some embodiments, the polypeptide that has reduced or weak binding to BMP9 has the sequence TEEN or TKEN at positions $X_{23}, X_{24}, X_{25},$ and $X_{26}$.

Additionally, in some embodiments, the polypeptide may bind to human BMP9 with a $K_D$ of about 200 pM or higher (e.g., a $K_D$ of about 200, 300, 400, 500, 600, 700, 800, or 900 pM or higher, e.g., a $K_D$ of about 1, 2, 3, 4, 5, 6, 7, 8, 9, 10, 20, 30, 40, or 50 nM or higher, e.g., a $K_D$ of between about 200 pM and about 50 nM). In some embodiments, the polypeptide does not substantially bind to human BMP9. In some embodiments, the polypeptide may bind to human activin A with a $K_D$ of about 800 pM or less (e.g., a $K_D$ of about 800, 700, 600, 500, 400, 300, 200, 100, 90, 80, 70, 60, 50, 40, 30, 20, 10, 9, 8, 7, 6, 5, 4, 3, 2, or 1 pM or less, e.g., a $K_D$ of between about 800 pM and about 200 pM). In some embodiments, the polypeptide may bind to human activin B with a $K_D$ of 800 pM or less (e.g., a $K_D$ of about 800, 700, 600, 500, 400, 300, 200, 100, 90, 80, 70, 60, 50, 40, 30, 20, 10, 9, 8, 7, 6, 5, 4, 3, 2, or 1 pM or less, e.g., a $K_D$ of between about 800 pM and about 200 pM) The polypeptide may also bind to growth and differentiation factor 11 (GDF-11) with a $K_D$ of approximately 5 pM or higher (e.g., a $K_D$ of about 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200 pM or higher).

II. Fc Domains

In some embodiments, a polypeptide described herein may include an extracellular ActRIIa variant fused to an Fc domain monomer of an immunoglobulin or a fragment of an Fc domain to increase the serum half-life of the polypeptide. A polypeptide including an extracellular ActRIIa variant fused to an Fc domain monomer may form a dimer (e.g., homodimer or heterodimer) through the interaction between two Fc domain monomers, which form an Fc domain in the dimer. As conventionally known in the art, an Fc domain is the protein structure that is found at the C-terminus of an immunoglobulin. An Fc domain includes two Fc domain monomers that are dimerized by the interaction between the $C_H3$ antibody constant domains. A wild-type Fc domain forms the minimum structure that binds to an Fc receptor, e.g., FcγRI, FcγRIIa, FcγRIIb, FcγRIIIa, FcγRIIIb, FcγRIV.

In some embodiments, an Fc domain may be mutated to lack effector functions, typical of a "dead" Fc domain. For example, an Fc domain may include specific amino acid substitutions that are known to minimize the interaction between the Fc domain and an Fcγ receptor. In some embodiments, an Fc domain is from an IgG1 antibody and includes amino acid substitutions L234A, L235A, and G237A. In some embodiments, an Fc domain is from an IgG1 antibody and includes amino acid substitutions D265A, K322A, and N434A. The aforementioned amino acid positions are defined according to Kabat (Sequences of Proteins of Immunological Interest, 5th Ed. Public Health Service, National Institutes of Health, Bethesda, MD. (1991)). The Kabat numbering of amino acid residues may be determined for a given antibody by alignment at regions of homology of the sequence of the antibody with a "standard" Kabat numbered sequence. Furthermore, in some embodiments, an Fc domain does not induce any immune system-related response. For example, the Fc domain in a dimer of a polypeptide including an extracellular ActRIIa variant fused to an Fc domain monomer may be modified to reduce the interaction or binding between the Fc domain and an Fcγ receptor. The sequence of an Fc domain monomer that may be fused to an extracellular ActAIIa variant is shown below (SEQ ID NO: 97):

THTCPPCPAPELLGGPSVFLFPPKPKDTLMISRTPEVTCVVVDVSHEDP

EVKFNWYVDGVEVHNAKTKPREEQYNSTYRVVSVLTVLHQDWLNGKEYK

CKVSNKALPVPIEKTISKAKGQPREPQVYTLPPSREEMTKNQVSLTCLV

KGFYPSDIAVEWESNGQPENNYKTTPPVLDSDGPFFLYSKLTVDKSRWQ

QGNVFSCSVMHEALHNHYTQKSLSLSPGK

In some embodiments, an Fc domain is from an IgG1 antibody and includes amino acid substitutions L12A, L13A, and G15A, relative to the sequence of SEQ ID NO: 97. In some embodiments, an Fc domain is from an IgG1 antibody and includes amino acid substitutions D43A, K100A, and N212A, relative to the sequence of SEQ ID NO: 97. In some embodiments, an extracellular ActRIIa variant described herein (e.g., an extracellular ActRIIa variant having the sequence of any one of SEQ ID NOs: 1-72 (e.g., SEQ ID NOs: 6-72) may be fused to the N- or C-terminus of an Fc domain monomer (e.g., SEQ ID NO: 97) through conventional genetic or chemical means, e.g., chemical conjugation. If desired, a linker (e.g., a spacer) can be inserted between the extracellular ActRIIa variant and the Fc domain monomer. The Fc domain monomer can be fused to the N- or C-terminus (e.g., C-terminus) of the extracellular ActRIIa variant.

In some embodiments, a polypeptide described herein may include an extracellular ActRIIa variant fused to an Fc domain. In some embodiments, the Fc domain contains one or more amino acid substitutions that reduce or inhibit Fc domain dimerization. In some embodiments, the Fc domain contains a hinge domain. The Fc domain can be of immunoglobulin antibody isotype IgG, IgE, IgM, IgA, or IgD. Additionally, the Fc domain can be an IgG subtype (e.g., IgG1, IgG2a, IgG2b, IgG3, or IgG4). The Fc domain can also be a non-naturally occurring Fc domain, e.g., a recombinant Fc domain.

Methods of engineering Fc domains that have reduced dimerization are known in the art. In some embodiments, one or more amino acids with large side-chains (e.g., tyrosine or tryptophan) may be introduced to the $C_H3$-$C_H3$ dimer interface to hinder dimer formation due to steric clash. In other embodiments, one or more amino acids with small side-chains (e.g., alanine, valine, or threonine) may be introduced to the $C_H3$-$C_H3$ dimer interface to remove favorable interactions. Methods of introducing amino acids with large or small side-chains in the $C_H3$ domain are described in, e.g., Ying et al. (*J Biol Chem.* 287:19399-19408, 2012), U.S. Patent Publication No. 2006/0074225, U.S. Pat. Nos. 8,216,805 and 5,731,168, Ridgway et al. (*Protein Eng.* 9:617-612, 1996), Atwell et al. (*J Mol Biol.* 270:26-35, 1997), and Merchant et al. (*Nat Biotechnol.* 16:677-681, 1998), all of which are incorporated herein by reference in their entireties.

In yet other embodiments, one or more amino acid residues in the $C_H3$ domain that make up the $C_H3$-$C_H3$ interface between two Fc domains are replaced with positively-charged amino acid residues (e.g., lysine, arginine, or histidine) or negatively-charged amino acid residues (e.g., aspartic acid or glutamic acid) such that the interaction becomes electrostatically unfavorable depending on the specific charged amino acids introduced. Methods of introducing charged amino acids in the $C_H3$ domain to disfavor or prevent dimer formation are described in, e.g., Ying et al. (*J Biol Chem.* 287:19399-19408, 2012), U.S. Patent Publication Nos. 2006/0074225, 2012/0244578, and 2014/0024111, all of which are incorporated herein by reference in their entireties.

In some embodiments of the invention, an Fc domain includes one or more of the following amino acid substitutions: T366W, T366Y, T394W, F405W, Y349T, Y349E, Y349V, L351T, L351H, L351N, L352K, P353S, S354D, D356K, D356R, D356S, E357K, E357R, E357Q, S364A, T366E, L368T, L368Y, L368E, K370E, K370D, K370Q, K392E, K392D, T394N, P395N, P396T, V397T, V397Q, L398T, D399K, D399R, D399N, F405T, F405H, F405R, Y407T, Y407H, Y4071, K409E, K409D, K409T, and K4091, relative to the sequence of human IgG1. In one particular embodiment, an Fc domain includes the amino acid substitution T366W, relative to the sequence of human IgG1. The sequence of wild-type Fc domain is shown in SEQ ID NO: 151.

III. Albumin-Binding Peptide

In some embodiments, a polypeptide described herein may include an extracellular ActRIIa variant fused to a serum protein-binding peptide. Binding to serum protein peptides can improve the pharmacokinetics of protein pharmaceuticals.

As one example, albumin-binding peptides that can be used in the methods and compositions described here are generally known in the art. In one embodiment, the albumin binding peptide includes the sequence DICLPRWGCLW (SEQ ID NO: 152).

In the present invention, albumin-binding peptides may be joined to the N- or C-terminus (e.g., C-terminus) of an extracellular ActRIIa variant described herein (e.g., an extracellular ActRIIa variant having the sequence of any one of SEQ ID NOs: 1-72 (e.g., SEQ ID NOs: 6-72) to increase the serum half-life of the extracellular ActRIIa variant. In some embodiments, an albumin-binding peptide is joined, either directly or through a linker, to the N- or C-terminus of an extracellular ActRIIa variant.

In some embodiments, an extracellular ActRIIa variant described herein (e.g., an extracellular ActRIIa variant having the sequence of any one of SEQ ID NOs: 1-72 (e.g., SEQ ID NOs: 6-72)) may be fused to the N- or C-terminus of albumin-binding peptide (e.g., SEQ ID NO: 152) through conventional genetic or chemical means, e.g., chemical conjugation. If desired, a linker (e.g., a spacer) can be inserted between the extracellular ActAIIa variant and the albumin-binding peptide. Without being bound to a theory, it is expected that inclusion of an albumin-binding peptide in an extracellular ActAIIa variant described herein may lead to prolonged retention of the therapeutic protein through its binding to serum albumin.

IV. Fibronectin Domain

In some embodiments, a polypeptide described herein may include an extracellular ActRIIa variant fused to fibronectin domains. Binding to fibronectin domains can improve the pharmacokinetics of protein pharmaceuticals.

Fibronectin domain is a high molecular weight glycoprotein of the extracellular matrix, or a fragment thereof, that binds to, e.g., membrane-spanning receptor proteins such as integrins and extracellular matrix components such as collagens and fibrins. In some embodiments of the present invention, a fibronectin domain is joined to the N- or C-terminus (e.g., C-terminus) of an extracellular ActRIIa variant described herein (e.g., an extracellular ActRIIa variant having the sequence of any one of SEQ ID NOs: 1-72 (e.g., SEQ ID NOs: 6-72) to increase the serum half-life of the extracellular ActRIIa variant. A fibronectin domain can be joined, either directly or through a linker, to the N- or C-terminus of an extracellular ActRIIa variant.

As one example, fibronectin domains that can be used in the methods and compositions described here are generally known in the art. In one embodiment, the fibronectin domain is a fibronectin type III domain (SEQ ID NO: 153) having amino acids 610-702 of the sequence of UniProt ID NO: P02751. In another embodiment, the fibronectin domain is an adnectin protein.

In some embodiments, an extracellular ActRIIa variant described herein (e.g., an extracellular ActRIIa variant having the sequence of any one of SEQ ID NOs: 1-72 (e.g., SEQ ID NOs: 6-72) may be fused to the N- or C-terminus of a fibronectin domain (e.g., SEQ ID NO: 153) through conventional genetic or chemical means, e.g., chemical conjugation. If desired, a linker (e.g., a spacer) can be inserted between the extracellular ActRIIa variant and the fibronectin domain. Without being bound to a theory, it is expected that inclusion of a fibronectin domain in an extracellular ActRIIa variant described herein may lead to prolonged retention of the therapeutic protein through its binding to integrins and extracellular matrix components such as collagens and fibrins.

V. Serum Albumin

In some embodiments, a polypeptide described herein may include an extracellular ActRIIa variant fused to serum albumin. Binding to serum albumins can improve the pharmacokinetics of protein pharmaceuticals.

Serum albumin is a globular protein that is the most abundant blood protein in mammals. Serum albumin is produced in the liver and constitutes about half of the blood serum proteins. It is monomeric and soluble in the blood. Some of the most crucial functions of serum albumin include transporting hormones, fatty acids, and other proteins in the body, buffering pH, and maintaining osmotic pressure needed for proper distribution of bodily fluids between blood vessels and body tissues. In preferred embodiments, serum albumin is human serum albumin. In some embodiments of the present invention, a human serum albumin is joined to the N- or C-terminus (e.g., C-terminus) of an extracellular ActRIIa variant described herein (e.g., an extracellular ActRIIa variant having the sequence of any one of SEQ ID NOs: 1-72 (e.g., SEQ ID NOs: 6-72)) to increase the serum half-life of the extracellular ActRIIa variant. A human serum albumin can be joined, either directly or through a linker, to the N- or C-terminus of an extracellular ActRIIa variant.

As one example, serum albumins that can be used in the methods and compositions described herein are generally known in the art. In one embodiment, the serum albumin includes the sequence of UniProt ID NO: P02768 (SEQ ID NO: 154).

In some embodiments, an extracellular ActRIIa variant described herein (e.g., an extracellular ActRIIa variant having the sequence of any one of SEQ ID NOs: 1-72 (e.g., SEQ ID NOs: 6-72) may be fused to the N- or C-terminus of a human serum albumin (e.g., SEQ ID NO: 154) through conventional genetic or chemical means, e.g., chemical conjugation. Il desired, a linker (e.g., a spacer) can be inserted between the extracellular ActRIIa variant and the human serum albumin. Without being bound to a theory, it is expected that inclusion of a human serum albumin in an extracellular ActRIIa variant described herein may lead to prolonged retention of the therapeutic protein.

VI. Linkers

A polypeptide described herein may include an extracellular ActRIIa variant (e.g., an extracellular ActRIIa variant having a sequence of any one of SEQ ID NOs: 1-72 (e.g., SEQ ID NOs: 6-72)) fused to a moiety by way of a linker. In some embodiments, the moiety increases stability of the polypeptide. Exemplary moieties include an Fc domain monomer, a wild-type Fc domain, an Fc domain with amino acid substitutions (e.g., one or more substitutions that reduce dimerization), an albumin-binding peptide, a fibronectin domain, or a human serum albumin. In the present invention, a linker between a moiety (e.g., an Fc domain monomer (e.g., the sequence of SEQ ID NO: 97), a wild-type Fc domain (e.g., SEQ ID NO: 151), an Fc domain with amino acid substitutions (e.g., one or more substitutions that reduce dimerization), an albumin-binding peptide (e.g., SEQ ID NO: 152), a fibronectin domain (e.g., SEQ ID NO: 153), or a human serum albumin (e.g., SEQ ID NO: 154) and an extracellular ActRIIa variant (e.g., an extracellular ActRIIa variant having the sequence of any one of SEQ ID NOs: 1-72 (e.g., SEQ ID NOs: 6-72), can be an amino acid spacer including 1-200 amino acids. Suitable peptide spacers are known in the art, and include, for example, peptide linkers containing flexible amino acid residues such as glycine, alanine, and serine. In some embodiments, a spacer can contain motifs, e.g., multiple or repeating motifs, of GA, GS, GG, GGA, GGS, GGG, GGGA (SEQ ID NO: 98), GGGS (SEQ ID NO: 99), GGGG (SEQ ID NO: 100), GGGGA (SEQ ID NO: 101), GGGGS (SEQ ID NO: 102), GGGGG (SEQ ID NO: 103), GGAG (SEQ ID NO: 104), GGSG (SEQ ID NO: 105), AGGG (SEQ ID NO: 106), or SGGG (SEQ ID NO: 107). In some embodiments, a spacer can contain 2 to 12 amino acids including motifs of GA or GS, e.g., GA, GS, GAGA (SEQ ID NO: 108), GSGS (SEQ ID NO: 109), GAGAGA (SEQ ID NO: 110), GSGSGS (SEQ ID NO: 111), GAGAGAGA (SEQ ID NO: 112), GSGSGSGS (SEQ ID NO: 113), GAGAGAGAGA (SEQ ID NO: 114), GSGSGSGSGS (SEQ ID NO: 115), GAGAGAGAGAGA (SEQ ID NO: 116), and GSGSGSGSGSGS (SEQ ID NO: 117). In some embodiments, a spacer can contain 3 to 12 amino acids including motifs of GGA or GGS, e.g., GGA, GGS, GGAGGA (SEQ ID NO: 118), GGSGGS (SEQ ID NO: 119), GGAGGAGGA (SEQ ID NO: 120), GGSGGSGGS (SEQ ID NO: 121), GGAGGAGGAGGA (SEQ ID NO: 122), and GGSGGSGGSGGS (SEQ ID NO: 123). In yet some embodiments, a spacer can contain 4 to 12 amino acids including motifs of GGAG (SEQ ID NO: 104), GGSG (SEQ ID NO: 105), e.g., GGAG (SEQ ID NO: 104), GGSG (SEQ ID NO: 105), GGAGGGAG (SEQ ID NO: 124), GGSGGGSG (SEQ ID NO: 125), GGAGGGAGG-GAG (SEQ ID NO: 126), and GGSGGGSGGGSG (SEQ ID NO: 127). In some embodiments, a spacer can contain motifs of GGGGA (SEQ ID NO: 101) or GGGGS (SEQ ID NO: 102), e.g., GGGGAGGGGAGGGGA (SEQ ID NO: 128) and GGGGGGGGSGGGGS (SEQ ID NO: 129). In some embodiments of the invention, an amino acid spacer between a moiety (e.g., an Fc domain monomer, a wild-type Fc domain, an Fc domain with amino acid substitutions (e.g., one or more substitutions that reduce dimerization), an albumin-binding peptide, a fibronectin domain, or a human serum albumin) and an extracellular ActRIIa variant (e.g., an extracellular ActAIIa variant having the sequence of any one of SEQ ID NOs: 1-72 (e.g., SEQ ID NOs: 6-72)) may be GGG, GGGA (SEQ ID NO: 98), GGGG (SEQ ID NO: 100), GGGAG (SEQ ID NO: 130), GGGAGG (SEQ ID NO: 131), or GGGAGGG (SEQ ID NO: 132).

In some embodiments, a spacer can also contain amino acids other than glycine, alanine, and serine, e.g., AAAL (SEQ ID NO: 133), AAAK (SEQ ID NO: 134), AAAR (SEQ ID NO: 135), EGKSSGSGSESKST (SEQ ID NO: 136), GSAGSAAGSGEF (SEQ ID NO: 137), AEAAAKEAAAKA (SEQ ID NO: 138), KESGSVSSE-QLAQFRSLD (SEQ ID NO: 139), GENLYFQSGG (SEQ ID NO: 140), SACYCELS (SEQ ID NO: 141), RSIAT (SEQ ID NO: 142), RPACKIPNDLKQKVMNH (SEQ ID NO: 143), GGSAGGSGSGSSGGSS-GASGTGTAGGTGSGSGTGSG (SEQ ID NO: 144), AAANSSIDLISVPVDSR (SEQ ID NO: 145), or GGSGGGSEGGGSEGGGSEGGGSEGGGSEGGGSGGGS (SEQ ID NO: 146). In some embodiments, a spacer can contain motifs, e.g., multiple or repeating motifs, of EAAAK (SEQ ID NO: 147). In some embodiments, a spacer can contain motifs, e.g., multiple or repeating motifs, of proline-rich sequences such as $(XP)_n$, in which X may be any amino acid (e.g., A, K, or E) and n is from 1-5, and PAPAP (SEQ ID NO: 148).

The length of the peptide spacer and the amino acids used can be adjusted depending on the two protein involved and the degree of flexibility desired in the final protein fusion polypeptide. The length of the spacer can be adjusted to ensure proper protein folding and avoid aggregate formation.

VII. Vectors, Host Cells, and Protein Production

The polypeptides of the invention can be produced from a host cell. A host cell refers to a vehicle that includes the necessary cellular components, e.g., organelles, needed to express the polypeptides and fusion polypeptides described herein from their corresponding nucleic acids. The nucleic acids may be included in nucleic acid vectors that can be introduced into the host cell by conventional techniques known in the art (e.g., transformation, transfection, electroporation, calcium phosphate precipitation, direct micro-injection, infection, or the like). The choice of nucleic acid vectors depends in part on the host cells to be used. Generally, preferred host cells are of either eukaryotic (e.g., mammalian) or prokaryotic (e.g., bacterial) origin.

Nucleic Acid Vector Construction and Host Cells

A nucleic acid sequence encoding the amino acid sequence of a polypeptide of the invention may be prepared by a variety of methods known in the art. These methods include, but are not limited to, oligonucleotide-mediated (or site-directed) mutagenesis and PCR mutagenesis. A nucleic acid molecule encoding a polypeptide of the invention may be obtained using standard techniques, e.g., gene synthesis. Alternatively, a nucleic acid molecule encoding a wild-type extracellular ActRIIa may be mutated to include specific amino acid substitutions using standard techniques in the art, e.g., QuikChange™ mutagenesis. Nucleic acid molecules can be synthesized using a nucleotide synthesizer or PCR techniques.

A nucleic acid sequence encoding a polypeptide of the invention may be inserted into a vector capable of replicating and expressing the nucleic acid molecule in prokaryotic or eukaryotic host cells.

Many vectors are available in the art and can be used for the purpose of the invention. Each vector may include various components that may be adjusted and optimized for compatibility with the particular host cell. For example, the vector components may include, but are not limited to, an origin of replication, a selection marker gene, a promoter, a ribosome binding site, a signal sequence, the nucleic acid sequence encoding protein of interest, and a transcription termination sequence.

In some embodiments, mammalian cells may be used as host cells for the invention. Examples of mammalian cell types include, but are not limited to, human embryonic kidney (HEK) (e.g., HEK293, HEK 293F), Chinese hamster ovary (CHO), HeLa, COS, PC3, Vero, MC3T3, NS0, Sp2/0, VERY, BHK, MDCK, W138, BT483, Hs578T, HTB2, BT20, T47D, NS0 (a murine myeloma cell line that does not endogenously produce any immunoglobulin chains), CRL7O3O, and HsS78Bst cells. In some embodiments, E. coli cells may also be used as host cells for the invention. Examples of E. coli strains include, but are not limited to, E. coli 294 (ATCC® 31,446), E. coli λ 1776 (ATCC® 31,537, E. coli BL21 (DE3) (ATCC® BAA-1025), and E. coli RV308 (ATCC® 31,608). Different host cells have characteristic and specific mechanisms for the posttranslational processing and modification of protein products (e.g., glycosylation). Appropriate cell lines or host systems may be chosen to ensure the correct modification and processing of the polypeptide expressed. The above-described expression vectors may be introduced into appropriate host cells using conventional techniques in the art, e.g., transformation, transfection, electroporation, calcium phosphate precipitation, and direct microinjection. Once the vectors are introduced into host cells for protein production, host cells are cultured in conventional nutrient media modified as appropriate for inducing promoters, selecting transformants, or amplifying the genes encoding the desired sequences. Methods for expression of therapeutic proteins are known in the art, see, for example, Paulina Balbas, Argelia Lorence (eds.) *Recombinant Gene Expression: Reviews and Protocols* (*Methods in Molecular Biology*), Humana Press: 2nd ed. 2004 and Vladimir Voynov and Justin A. Caravella (eds.) *Therapeutic Proteins: Methods and Protocols* (*Methods in Molecular Biology*) Humana Press; 2nd ed. 2012.

Protein Production, Recovery, and Purification

Host cells used to produce the polypeptides of the invention may be grown in media known in the art and suitable for culturing of the selected host cells. Examples of suitable media for mammalian host cells include Minimal Essential Medium (MEM), Dulbecco's Modified Eagle's Medium (DMEM), Expi293™ Expression Medium, DMEM with supplemented fetal bovine serum (FBS), and RPMI-1640. Examples of suitable media for bacterial host cells include Luria broth (LB) plus necessary supplements, such as a selection agent, e.g., ampicillin. Host cells are cultured at suitable temperatures, such as from about 20° C. to about 39° C., e.g., from 25° C. to about 37° C., preferably 37° C., and $CO_2$ levels, such as 5 to 10%. The pH of the medium is generally from about 6.8 to 7.4, e.g., 7.0, depending mainly on the host organism. If an inducible promoter is used in the expression vector of the invention, protein expression is induced under conditions suitable for the activation of the promoter.

In some embodiments, depending on the expression vector and the host cells used, the expressed protein may be secreted from the host cells (e.g., mammalian host cells) into the cell culture media. Protein recovery may involve filtering the cell culture media to remove cell debris. The proteins may be further purified. A polypeptide of the invention may be purified by any method known in the art of protein purification, for example, by chromatography (e.g., ion exchange, affinity, and size-exclusion column chromatography), centrifugation, differential solubility, or by any other standard technique for the purification of proteins. For example, the protein can be isolated and purified by appropriately selecting and combining affinity columns such as Protein A column (e.g., POROS Protein A chromatography) with chromatography columns (e.g., POROS HS-50 cation exchange chromatography), filtration, ultra filtration, salting-out and dialysis procedures.

In other embodiments, host cells may be disrupted, e.g., by osmotic shock, sonication, or lysis, to recover the expressed protein. Once the cells are disrupted, cell debris may be removed by centrifugation or filtration. In some instances, a polypeptide can be conjugated to marker sequences, such as a peptide to facilitate purification. An example of a marker amino acid sequence is a hexa-histidine peptide (His-tag), which binds to nickel-functionalized agarose affinity column with micromolar affinity. Other peptide tags useful for purification include, but are not limited to, the hemagglutinin "HA" tag, which corresponds to an epitope derived from Influenza hemagglutinin protein (Wilson et al., *Cell* 37:767, 1984).

Alternatively, the polypeptides of the invention can be produced by the cells of a subject (e.g., a human), e.g., in the context of gene therapy, by administrating a vector (such as a viral vector (e.g., a retroviral vector, adenoviral vector, poxviral vector (e.g., vaccinia viral vector, such as Modified Vaccinia Ankara (MVA)), adeno-associated viral vector, and alphaviral vector) containing a nucleic acid molecule encoding the polypeptide of the invention. The vector, once inside a cell of the subject (e.g., by transformation, transfection, electroporation, calcium phosphate precipitation, direct microinjection, infection, etc.) will promote expression of the polypeptide, which is then secreted from the cell. If treatment of a disease or disorder is the desired outcome, no further action may be required. If collection of the protein is desired, blood may be collected from the subject and the protein purified from the blood by methods known in the art.

VIII. Pharmaceutical Compositions and Preparations

The invention features pharmaceutical compositions that include the polypeptides described herein (e.g., a polypeptide including an extracellular ActRIIa variant (e.g., an extracellular ActRIIa variant having the sequence of any one of SEQ ID NOs: 1-72 (e.g., SEQ ID NOs: 6-72). In some embodiments, a pharmaceutical composition of the invention includes a polypeptide including an extracellular ActRIIa variant (e.g., an extracellular ActAIIa variant having the sequence of any one of SEQ ID NOs: 1-70 (e.g., SEQ ID NOs: 6-70) with a C-terminal extension (e.g., 1, 2, 3, 4, 5, 6 or more additional amino acids) as the therapeutic protein. In some embodiments, a pharmaceutical composition of the invention includes a polypeptide including an extracellular ActRIIa variant (e.g., an extracellular ActRIIa variant having the sequence of any one of SEQ ID NOs: 1-72 (e.g., SEQ ID NOs: 6-72)) fused to a moiety (e.g., Fc domain monomer, or a dimer thereof, a wild-type Fc domain, an Fc domain with amino acid substitutions (e.g., one or more substitutions that reduce dimerization), an albumin-binding peptide, a fibronectin domain, or a human serum albumin) as the therapeutic protein. In some embodiments, a pharmaceutical composition of the invention including a polypeptide of the invention may be used in combination with other agents (e.g., therapeutic biologics and/or small molecules) or compositions in a therapy. In addition to a therapeutically effective amount of the polypeptide, the pharmaceutical composition may include one or more pharmaceutically acceptable carriers or excipients, which can be formulated by methods known to those skilled in the art. In some embodiments, a pharmaceutical composition of the invention includes a nucleic acid molecule (DNA or RNA, e.g., mRNA) encoding a polypeptide of the invention, or a vector containing such a nucleic acid molecule.

Acceptable carriers and excipients in the pharmaceutical compositions are nontoxic to recipients at the dosages and concentrations employed. Acceptable carriers and excipients may include buffers such as phosphate, citrate, HEPES, and TAE, antioxidants such as ascorbic acid and methionine, preservatives such as hexamethonium chloride, octadecyldimethylbenzyl ammonium chloride, resorcinol, and benzalkonium chloride, proteins such as human serum albumin, gelatin, dextran, and immunoglobulins, hydrophilic polymers such as polyvinylpyrrolidone, amino acids such as glycine, glutamine, histidine, and lysine, and carbohydrates such as glucose, mannose, sucrose, and sorbitol. Pharmaceutical compositions of the invention can be administered parenterally in the form of an injectable formulation. Pharmaceutical compositions for injection can be formulated using a sterile solution or any pharmaceutically acceptable liquid as a vehicle. Pharmaceutically acceptable vehicles include, but are not limited to, sterile water, physiological saline, and cell culture media (e.g., Dulbecco's Modified Eagle Medium (DMEM), $\alpha$-Modified Eagles Medium ($\alpha$-MEM), F-12 medium). Formulation methods are known in the art, see e.g., Banga (ed.) *Therapeutic Peptides and Proteins: Formulation, Processing and Delivery Systems* (3rd ed.) Taylor & Francis Group, CRC Press (2015).

The pharmaceutical compositions of the invention may be prepared in microcapsules, such as hydroxylmethylcellulose or gelatin-microcapsule and poly-(methylmethacrylate) microcapsule. The pharmaceutical compositions of the invention may also be prepared in other drug delivery systems such as liposomes, albumin microspheres, microemulsions, nano-particles, and nanocapsules. Such techniques are described in Remington: The Science and Practice of Pharmacy $22^{th}$ edition (2012). The pharmaceutical compositions to be used for in vivo administration must be sterile. This is readily accomplished by filtration through sterile filtration membranes.

The pharmaceutical compositions of the invention may also be prepared as a sustained-release formulation. Suitable examples of sustained-release preparations include semipermeable matrices of solid hydrophobic polymers containing the polypeptides of the invention. Examples of sustained release matrices include polyesters, hydrogels, polyactides, copolymers of L-glutamic acid and $\gamma$ ethyl-L-glutamate, non-degradable ethylene-vinyl acetate, degradable lactic acid-glycolic acid copolymers such as LUPRON DEPOT™, and poly-D-(−)-3-hydroxybutyric acid. Some sustained-release formulations enable release of molecules over a few months, e.g., one to six months, while other formulations release pharmaceutical compositions of the invention for shorter time periods, e.g., days to weeks.

The pharmaceutical composition may be formed in a unit dose form as needed. The amount of active component, e.g., a polypeptide of the invention, included in the pharmaceutical preparations is such that a suitable dose within the designated range is provided (e.g., a dose within the range of 0.01-100 mg/kg of body weight).

The pharmaceutical composition for gene therapy can be in an acceptable diluent, or can include a slow release matrix in which the gene delivery vehicle is imbedded. If hydrodynamic injection is used as the delivery method, the pharmaceutical composition containing a nucleic acid molecule encoding a polypeptide described herein or a vector (e.g., a viral vector) containing the nucleic acid molecule is delivered rapidly in a large fluid volume intravenously. Vectors that may be used as in vivo gene delivery vehicle include, but are not limited to, retroviral vectors, adenoviral vectors, poxviral vectors (e.g., vaccinia viral vectors, such as Modified Vaccinia Ankara), adeno-associated viral vectors, and alphaviral vectors.

IX. Routes, Dosage, and Administration

Pharmaceutical compositions that include the polypeptides of the invention as the therapeutic proteins may be formulated for, e.g., intravenous administration, parenteral administration, subcutaneous administration, intramuscular administration, intra-arterial administration, intrathecal administration, or intraperitoneal administration. The pharmaceutical composition may also be formulated for, or administered via, oral, nasal, spray, aerosol, rectal, or vaginal administration. For injectable formulations, various effective pharmaceutical carriers are known in the art. See, e.g., ASHP Handbook on Injectable Drugs, Toissel, 18th ed. (2014).

In some embodiments, a pharmaceutical composition that includes a nucleic acid molecule encoding a polypeptide of the invention or a vector containing such nucleic acid molecule may be administered by way of gene delivery. Methods of gene delivery are well-known to one of skill in the art. Vectors that may be used for in vivo gene delivery and expression include, but are not limited to, retroviral vectors, adenoviral vectors, poxviral vectors (e.g., vaccinia viral vectors, such as Modified Vaccinia Ankara (MVA), adeno-associated viral vectors, and alphaviral vectors. In some embodiments, mRNA molecules encoding polypeptides of the invention may be administered directly to a subject.

In some embodiments of the present invention, nucleic acid molecules encoding a polypeptide described herein or vectors containing such nucleic acid molecules may be administered using a hydrodynamic injection platform. In the hydrodynamic injection method, a nucleic acid molecule encoding a polypeptide described herein is put under the control of a strong promoter in an engineered plasmid (e.g., a viral plasmid). The plasmid is often delivered rapidly in a large fluid volume intravenously. Hydrodynamic injection uses controlled hydrodynamic pressure in veins to enhance cell permeability such that the elevated pressure from the rapid injection of the large fluid volume results in fluid and plasmid extravasation from the vein. The expression of the nucleic acid molecule is driven primarily by the liver. In mice, hydrodynamic injection is often performed by injection of the plasmid into the tail vein. In certain embodiments, mRNA molecules encoding a polypeptide described herein may be administered using hydrodynamic injection.

The dosage of the pharmaceutical compositions of the invention depends on factors including the route of administration, the disease to be treated, and physical characteristics, e.g., age, weight, general health, of the subject. A pharmaceutical composition of the invention may include a dosage of a polypeptide of the invention ranging from 0.01 to 500 mg/kg (e.g., 0.01, 0.1, 0.2, 0.3, 0.4, 0.5, 1, 2, 3, 4, 5, 10, 15, 20, 25, 30, 35, 40, 45, 50, 100, 150, 200, 250, 300, 350, 400, 450, or 500 mg/kg) and, in a more specific embodiment, about 0.1 to about 30 mg/kg and, in a more specific embodiment, about 0.3 to about 30 mg/kg. The dosage may be adapted by the physician in accordance with conventional factors such as the extent of the disease and different parameters of the subject.

The pharmaceutical compositions are administered in a manner compatible with the dosage formulation and in such amount as is therapeutically effective to result in an improvement or remediation of the symptoms. The pharmaceutical compositions are administered in a variety of dosage forms, e.g., intravenous dosage forms, subcutaneous dosage forms, and oral dosage forms (e.g., ingestible solutions, drug release capsules). Generally, therapeutic proteins are dosed at 0.1-100 mg/kg, e.g., 1-50 mg/kg. Pharmaceutical compositions that include a polypeptide of the invention may be administered to a subject in need thereof, for example, one or more times (e.g., 1-10 times or more) daily, weekly, biweekly, monthly, bimonthly, quarterly, biannually, annually, or as medically necessary. In some embodiments, pharmaceutical compositions that include a polypeptide of the invention may be administered to a subject in need thereof weekly, biweekly, monthly, bimonthly, or quarterly. Dosages may be provided in either a single or multiple dosage regimens. The timing between administrations may decrease as the medical condition improves or increase as the health of the patient declines.

X. Methods of Treatment

The invention is based on the discovery that substituting amino acids from the extracellular portion of ActRIIb into the extracellular portion ActRIIa yields ActRIIa variants with improved properties. The ActAIIa variants generated by introducing residues from ActRIIb into ActRIIa retain the beneficial properties of ActRIIa, such as longer serum half-life and low binding affinity to BMP9, and gain some of the beneficial properties of ActRIIb, such as increased binding to activins A and B (see Table 4) and an ability to increase muscle mass (see Examples 1-3 and 5-6). These ActRIIa variant properties make for a useful therapeutic that can compete with endogenous activin receptors for ligand binding. As the ActRIIa variants contain the extracellular portion of the receptor, they will be soluble and able to bind to and sequester ligands (e.g., activins A and B, myostalin, GDF11) without activating intracellular signaling pathways. Therefore, the extracellular ActRIIa variants can be used to treat diseases or conditions in which elevated activin signaling has been implicated (e.g., associated with increased expression of activin receptors or activin receptor ligands). For example, loss of myostalin has been shown to increase skeletal muscle mass, suggesting that myostatin inhibits skeletal muscle growth. It follows that treatment with a therapeutic agent that binds to myostatin and reduces its interaction with endogenous receptors could be a viable approach for increasing muscle mass. Indeed, extracellular ActRIIa variants of the invention increase muscle mass in mice (see Examples 1-3 and 5-6). These data indicate that the extracellular ActAIIa variants described herein can be used to increase muscle mass and treat subjects with diseases or conditions that result in muscle weakness or atrophy.

Moreover, these data provide a compelling reason to use the extracellular ActAIIa variants of the invention to treat other diseases or conditions associated with elevated expression of activin receptors or activin receptor ligands, such as metabolic diseases (e.g., obesity, Type-1 diabetes, and Type-2 diabetes). Many studies have shown that increasing muscle mass is one way to reduce body fat and/or body weight, indicating that the extracellular ActAIIa variants described herein can be used to treat metabolic diseases (e.g., obesity, Type-1 diabetes, and Type-2 diabetes) indirectly by increasing muscle mass. However, as activin receptors and activin receptor ligands have been shown to be increased in in obese mice and humans, the extracellular ActAIIa variants described herein can be used to treat obesity by reducing elevated activin receptor signaling (e.g., by binding to and sequestering endogenous activin receptor ligands, e.g., activins and myostatin).

The invention provides compositions and methods of treatment that may be used to increase muscle mass and strength in a subject in need thereof. In some embodiments, the subject may have a disease that results in muscle weakness or atrophy (e.g., skeletal muscle weakness or atrophy). In some embodiments, the methods described herein are directed to affecting myostatin, activin, and/or BMP9 signaling in a subject having a disease or condition involving weakness and atrophy of muscles. In some embodiments, a polypeptide including an extracellular ActRIIa variant described herein reduces or inhibits the binding of myostatin, activin, and/or BMP9 to their receptors, e.g., ActRIIa, ActRIIb, and BMPRII (e.g., ActRIIa). In some embodiments, affecting myostatin, activin, and/or BMP9 signaling (e.g., reducing or inhibiting the binding of myostatin, activin, and/or BMP9 to their receptors, e.g., ActRIIa, ActRIIb, and BMPRII (e.g., ActRIIa)) results in an increase in the subject's muscle mass.

In some embodiments, the polypeptides described herein (e.g., a polypeptide including an extracellular ActRIIa variant (e.g., an extracellular ActRIIa variant having the sequence of any one of SEQ ID NOs: 1-72 (e.g., SEQ ID NOs: 6-72)) may be administered to a subject to increase muscle mass, or to affect myostatin, activin, and/or BMP9 signaling in the subject. In some embodiments, the methods described herein increase bone mineral density of the subject. In some embodiments, the methods described herein do not cause any vascular complications in the subject, such as increased vascular permeability or leakage. In some embodiments of the methods described herein, the subject has a disease or condition involving weakness and atrophy of muscles (e.g., Duchenne muscular dystrophy (DMD), facioscapulohumeral muscular dystrophy (FSHD), inclusion body myositis (IBM), amyotrophic lateral sclerosis (ALS), sarcopenia, or cancer cachexia).

The invention also includes methods of treating a subject having Duchenne muscular dystrophy (DMD), lacioscapulohumeral muscular dystrophy (FSHD), inclusion body myositis (IBM), amyotrophic lateral sclerosis (ALS), sarcopenia, or cancer cachexia by administering to the subject a polypeptide described herein (e.g., a polypeptide including an extracellular ActRIIa variant (e.g., an extracellular ActRIIa variant having the sequence of any one of SEQ ID NOs: 1-72 (e.g., SEQ ID NOs: 6-72)).

The compositions and methods described herein can also be used to treat and/or prevent medical conditions, such as metabolic diseases, e.g., obesity and diabetes (Type-1 and Type-2 diabetes). In some embodiments, the subject may have a disease that results in obesity. In some embodiments, the methods described herein are directed to affecting myostatin, activin, and/or BMP9 signaling in a subject having obesity, diabetes (Type-1 and Type-2 diabetes), or a disease or condition that results in obesity. In some embodiments, a polypeptide including an extracellular ActRIIa variant described herein reduces or inhibits the binding of myostatin, activin, and/or BMP9 to their receptors, e.g., ActRIIa, ActRIIb, and BMPRII (e.g., ActRIIa). In some embodiments, affecting myostatin, activin, and/or BMP9 signaling (e.g., reducing or inhibiting the binding of myostatin, activin, and/or BMP9 to their receptors, e.g., ActRIIa, ActRIIb, and BMPRII (e.g., ActRIIa) results in a reduction in the subject's body fat (e.g., amount of body fat or body fat percentage), a reduction in the subject's body weight or body weight gain, a reduction in fasting insulin levels, an increase in glucose clearance, or an increase in insulin sensitivity (e.g., a reduction in insulin resistance).

In some embodiments, the polypeptides described herein (e.g., a polypeptide including an extracellular ActRIIa variant (e.g., an extracellular ActRIIa variant having the sequence of any one of SEQ ID NOs: 1-72 (e.g., SEQ ID NOs: 6-72)) may be administered to a subject to prevent the development of obesity (e.g., in patients at risk of developing obesity, e.g., patients who are overweight, who have a family history of obesity, or who have other medical conditions or genetic risk factors linked to increased risk of obesity) and/or to treat patients already diagnosed with obesity. For example, administration of the extracellular ActRIIa variant (e.g., an extracellular ActRIIa variant having the sequence of any one of SEQ ID NOs: 1-72 (e.g., SEQ ID NOs: 6-72)) to a subject may help to reduce the body weight of the subject by decreasing the amount of fat. In some embodiments, the extracellular ActRIIa variant decreases the amount of fat while maintaining or increasing the amount of lean mass.

In some embodiments, the polypeptides described herein (e.g., a polypeptide including an extracellular ActRIIa variant (e.g., an extracellular ActRIIa variant having the sequence of any one of SEQ ID NOs: 1-72 (e.g., SEQ ID NOs: 6-72) may be used to prevent the development of diabetes (e.g., Type-1 and Type-2 diabetes) and/or to treat patients already diagnosed with diabetes. Patients who are likely to develop diabetes, e.g., individuals with genetic predisposition, family history of diabetes, prediabetes, association with other autoimmune diseases, or other metabolic diseases, may be administered the polypeptides described herein (e.g., a polypeptide including an extracellular ActRIIa variant (e.g., an extracellular ActRIIa variant having the sequence of any one of SEQ ID NOs: 1-72 (e.g., SEQ ID NOs: 6-72)) prophylactically, such that the extracellular ActRIIa polypeptides may maintain the normal function and health of B-cells and prevent or delay the autoimmune inflammatory damage to B-cells. In other embodiments, the polypeptides described herein (e.g., a polypeptide including an extracellular ActAIIa variant (e.g., an extracellular ActRIIa variant having the sequence of any one of SEQ ID NOs: 1-72 (e.g., SEQ ID NOs: 6-72)) may be administered to individuals before they would be diagnosed with diabetes (e.g., Type-1 and Type-2 diabetes) or develop clinical symptoms of diabetes, e.g., high blood glucose level, high fasting insulin level, insulin resistance, polyuria, polydipsia, and polyphagia. In some embodiments, the extracellular ActAIIa polypeptides may be administered to patients prior to the patients needing insulin. In yet other embodiments, the administration of extracellular ActAIIa polypeptides may delay or postpone the need for insulin treatment in diabetic patients. For example, administration of the extracellular ActRIIa polypeptides of the invention to a subject may help to increase the rate of glucose clearance from the blood.

In some embodiments, the polypeptides described herein (e.g., a polypeptide including an extracellular ActRIIa variant (e.g., an extracellular ActRIIa variant having the sequence of any one of SEQ ID NOs: 1-72 (e.g., SEQ ID NOs: 6-72)) may be administered to a subject to prevent the development of and/or treat patients with obesity or diabetes (e.g., Type-1 and Type-2 diabetes), or to affect myostatin, activin, and/or BMP9 signaling in the subject (e.g., to reduce or inhibit the binding of activin, myostatin, and/or BMP9 to their receptors). In some embodiments, the methods described herein reduce body fat (e.g., reduce the amount of subcutaneous and/or visceral fat, reduce adiposity, reduce the weights of epididymal and perirenal fat pads, or reduce body fat percentage). In some embodiments, the methods described herein reduce body weight or reduce body weight gain (e.g., reduce the percentage of body weight gain). In some embodiments, the methods described herein reduce the proliferation of adipose cells. In some embodiments, the methods described herein reduce LDL. In some embodiments, the methods described herein reduce triglycerides. In some embodiments, the methods described herein improve the serum lipid profile of the subject. In some embodiments, the methods described herein reduce body fat without reducing lean mass (e.g., do not affect lean mass or increase lean mass). In some embodiments, the methods described herein reduce body fat and increase muscle mass. In some embodiments, the methods described herein reduce blood glucose levels (e.g., fasting glucose levels) or and/or increase glucose clearance. In some embodiments, the methods described herein reduce fasting insulin levels and/or improve insulin sensitivity (e.g., reduce insulin resistance). In some embodiments, the methods described herein regulate insulin biosynthesis and/or secretion from β-cells. In some embodiments, the methods described herein do not affect the appetite for food intake. In some embodiments, the methods described herein do not cause any vascular complications in the subject, such as increased vascular permeability or leakage.

In some embodiments, the polypeptides described herein (e.g., a polypeptide including an extracellular ActRIIa variant (e.g., an extracellular ActRIIa variant having the sequence of any one of SEQ ID NOs: 1-72 (e.g., SEQ ID NOs: 6-72) decrease body fat, decrease body weight, or increase insulin sensitivity and/or glucose clearance by increasing muscle mass.

In any of the methods described herein, a polypeptide including an extracellular ActRIIa variant (e.g., an extracellular ActAIIa variant having the sequence of any one of SEQ ID NOs: 1-71 (e.g., SEQ ID NOs: 6-71)) that further includes a C-terminal extension of one to six amino acids (e.g., 1, 2, 3, 4, 5, 6 or more amino acids) may be used as the therapeutic protein. In any of the methods described herein, a dimer (e.g., homodimer or heterodimer) of a polypeptide including an extracellular ActRIIa variant (e.g., an extracellular ActRIIa variant having the sequence of any one of SEQ ID NOs: 1-72 (e.g., SEQ ID NOS: 6-72) fused to a moiety (e.g., an Fc domain monomer, a wild-type Fc domain, an Fc domain with amino acid substitutions (e.g., one more substitutions that reduce dimerization), an albumin-binding peptide, a fibronectin domain, or a human serum albumin) may be used as the therapeutic protein. Nucleic acids encoding the polypeptides described herein, or vectors containing said nucleic acids can also be administered according to any of the methods described herein. In any of the methods described herein, the polypeptide, nucleic acid, or vector can be administered as part of a pharmaceutical composition.

EXAMPLES

Example 1—Effect of Extracellular ActAIIa Variants on Body Weight

C57Bl/6 mice received a single hydrodynamic injection of a plasmid construct encoding one of the following six polypeptides (n=10/group):
  (1) human Fc (hFc),
  (2) extracellular ActRIIa (SEQ ID NO: 73) fused to the N-terminus of hFc through a GGG linker;
  (3) extracellular ActRIIb (SEQ ID NO: 74) fused to the N-terminus of hFc through a GGG linker;
  (4) extracellular ActRIIa variant (SEQ ID NO: 69) fused to the N-terminus of hFc through a GGG linker; and
  (5) extracellular ActRIIb variant (SEQ ID NO: 149) fused to the N-terminus of hFc through a GGG linker.

Figure 2A:
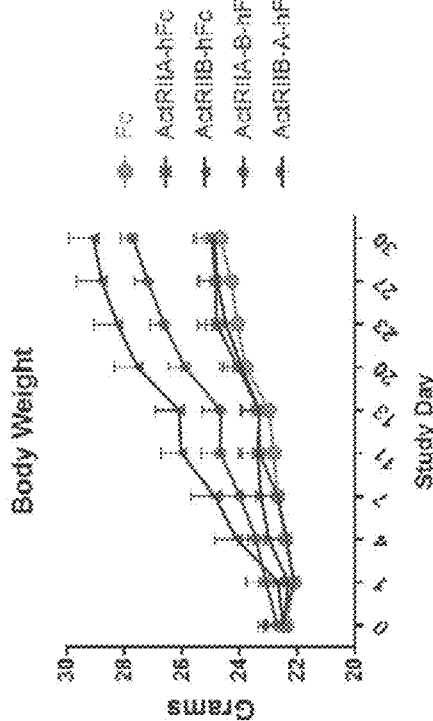

100 μg of plasmid construct was delivered in a volume of 10% body weight over 5-8 seconds. The high volume and short period of injection provides the pressure needed to introduce the plasmid into the liver cells where the plasmid will be expressed, specifically the proteins of interest are expressed under a strong and ubiquitous promoter. The protein of interest is secreted under the endogenous machinery of the liver cells and circulates freely. Mice were weighted twice weekly for 30 days and measurements were recorded as absolute body weight (BW) in grams and as a percent of body weight change from baseline measurements (FIGS. 2A and 2B, respectively).

Example 2—Effect of Extracellular ActAIIa Variants on Muscle Mass

Mice received a single hydrodynamic injection of a plasmid construct encoding one of the following six polypeptides (n=10/group):
  (1) human Fc (hFc),
  (2) extracellular ActRIIa (SEQ ID NO: 73) fused to the N-terminus of hFc through a GGG linker;
  (3) extracellular ActRIIb (SEQ ID NO: 74) fused to the N-terminus of hFc through a GGG linker;
  (4) extracellular ActRIIa variant (SEQ ID NO: 69) fused to the N-terminus of hFc through a GGG linker; and
  (5) extracellular ActRIIb variant (SEQ ID NO: 149) fused to the N-terminus of hFc through a GGG linker.

Figure 3A:
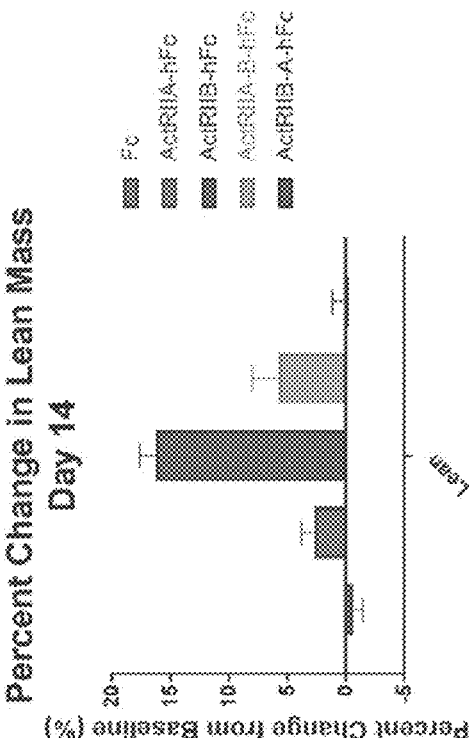
FIGS. 3A and 3B are bar graphs showing the effects of extracellular ActRIIa variants on muscle mass.
Figure 3B:
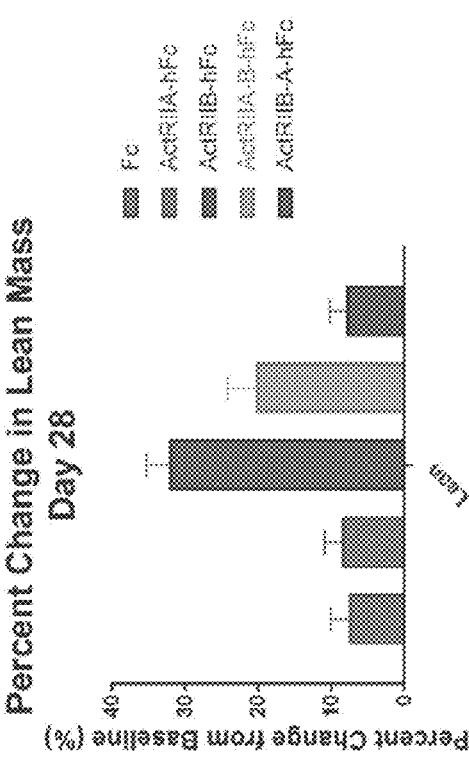

100 μg of plasmid construct was delivered in a volume of 10% body weight over 5-8 seconds. The high volume and short period of injection provides the pressure needed to introduce the plasmid into the liver cells where the plasmid will be expressed, specifically the proteins of interest are expressed under a strong and ubiquitous promoter. The protein of interest is secreted under the endogenous machinery of the liver cells and circulates freely. On study days 0 (baseline), 14, and 28, mice underwent NMR analysis for determination of lean mass using a MiniSpec LF90 NMR analyzer (Bruker, Woodlands, TX). The percent lean mass changes from baseline were recorded on days 14 and 28 (FIGS. 3A and 3B).

Example 3—Effect of Extracellular ActAIIa Variants on Body Weight when Administered as Purified Recombinant Protein Female C57Bl/6 mice (Taconic Biosciences, Hudson NY) received an intraperitoneal injection of tris-buffered saline vehicle or one of the following five purified recombinant polypeptides at a dosage of 10 mg/kg twice weekly for four weeks (n=10/group):
  (1) tris-buffered saline vehicle,
  (2) extracellular ActRIIa (SEQ ID NO: 73) fused to the N-terminus of hFc through a GGG linker;
  (3) extracellular ActRIIb (SEQ ID NO: 74) fused to the N-terminus of hFc through a GGG linker;
  (4) extracellular ActRIIa/b variant (SEQ ID NO: 69) fused to the N-terminus of hFc through a GGG linker;
  (5) extracellular ActRIIa/bΔ9 variant (SEQ ID NO: 58) fused to the N-terminus of hFc through a GGG linker; and
  (6) extracellular ActRII a/bΔ9 min variant (SEQ ID NO: 6) fused to the N-terminus of hFc through a GGG linker.

Purified recombinant protein was made by transient expression in HEK293 cell and purified from the conditioned media using Protein-A Sepharose chromatography.

Figures 4A, 4B:
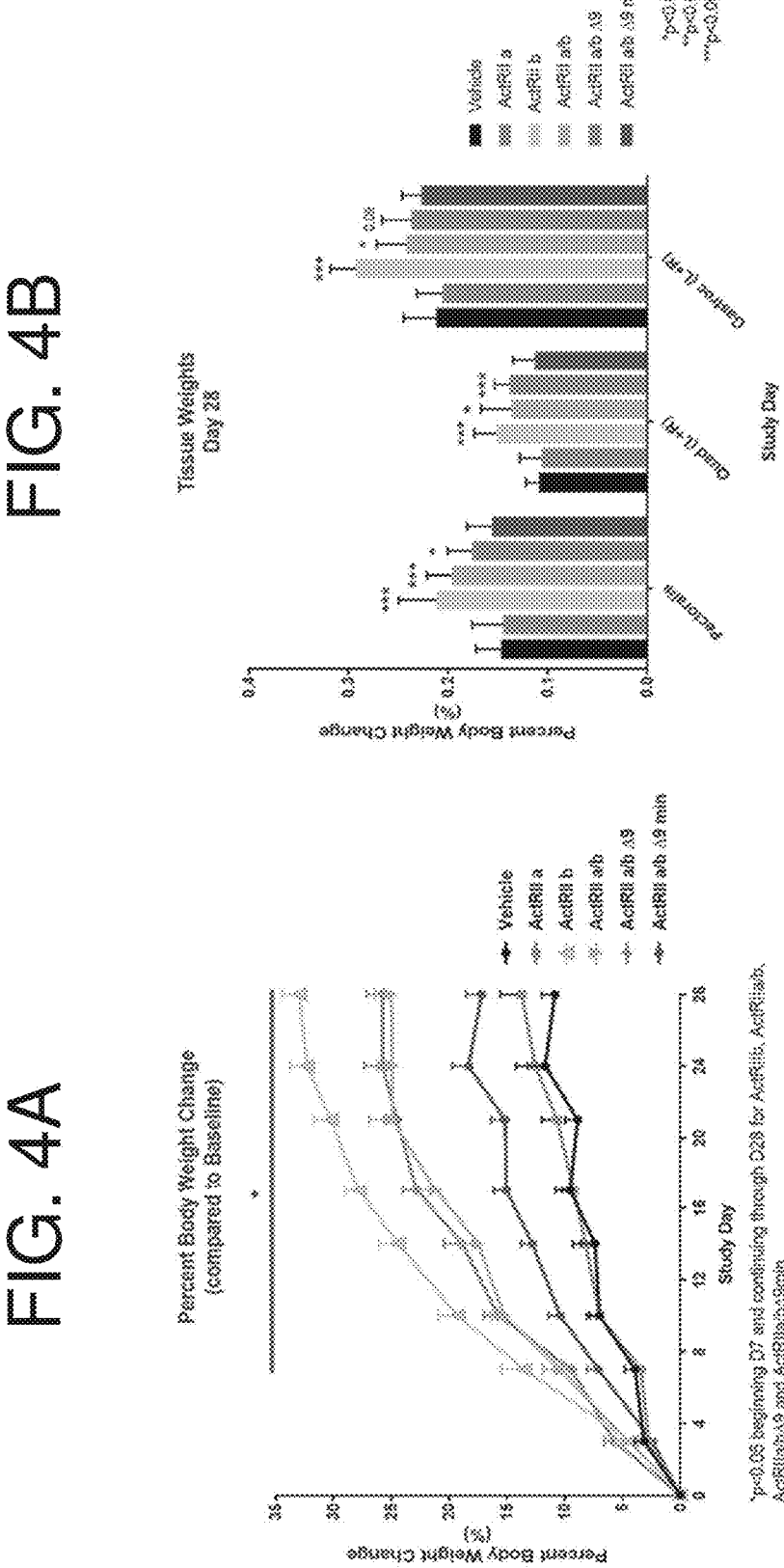
FIG. 4A is a scatter plot showing the effects of extracellular ActRIIa variants on body weight. Mice received an intraperitoneal injection of the indicated purified recombinant ActAIIa variant or a vehicle control twice weekly for four weeks.
FIG. 4B is a bar graph showing the effects of extracellular ActRIIa variants on individual muscle weights by tissue analysis.

Following four weeks of dosing the mice were humanely sacrificed and necropsy was performed. Necropsy included collection of weights for total body, and the gastrocnemius, pectoralis, and quadriceps muscles. Statistical analysis of muscle/body weight data was performed in GraphPad Prism 7 (GraphPad Software, La Jolla CA) (FIGS. 4A and 4B, respectively).

Example 4—Evaluation of ActAIIa Variants Binding Affinity by Surface Plasmon Resonance (SPR)

The Biacore 3000 was used to measure the kinetics of the interactions between the ActRIIa variants and the ligands Activin A, Activin B, growth differentiation factor 11 (GDF11), and BMP-9. ActAIIa variants were expressed and purified according to the methodology described in Example 3. The ActRIIa variants were immobilized on the chip (CM4 or CM5) with capture antibodies (anti-mouse from GEGE) in flow cells 2-4 to ensure proper orientation. Flow cell 1 was used as a reference cell to subtract any nonspecific binding and bulk effects. HBS-EP+ buffer from GE Health-care™ was used as a running buffer. Each ligand was run in a concentration series at 40 μl/min to avoid mass transport effects. The data was analyzed using Scrubber2 by Bio-Logic™ Software to calculate the $K_D$ of each interaction (Table 4).

(7) pLEV113-ActRIIa/b-delta 9m2 (SEQ ID NO: 38) fused to the N-terminus of hFc through a GGG linker;

(8) pLEV113-ActRIIa/b-delta 9m3 (SEQ ID NO: 41) fused to the N-terminus of hFc through a GGG linker;

(9) pLEV113-ActRIIa/b-delta 9m4 (SEQ ID NO: 44) fused to the N-terminus of hFc through a GGG linker;

(10) pLEV113-ActRIIa/bmax1 (SEQ ID NO: 70) fused to the N-terminus of hFc through a GGG linker;

(11) pLEV113-ActRIIa/bmax2 (SEQ ID NO: 71) fused to the N-terminus of hFc through a GGG linker; and

(12) pLEV113-ActRIIa/bmax1 (SEQ ID NO: 72) fused to the N-terminus of hFc through a GGG linker.

100 μg of plasmid construct was delivered in a volume of 10% body weight over 5-8 seconds. The high volume and short period of injection provides the pressure needed to introduce the plasmid into the liver cells where the plasmid will be expressed, specifically the proteins of interest are expressed under a strong and ubiquitous promoter. The protein of interest is secreted under the endogenous machin-

TABLE 4

| Comparison of ActRIIa variant binding affinity (KD) to various ligands | | | | |
|---|---|---|---|---|
| Vehicle | Activin A ($K_D$) N/A | Activin B ($K_D$) N/A | GDF-11 ($K_D$) N/A | BMP-9 ($K_D$) N/A |
| ActRIIa (SEQ ID NO: 73) | 1 nM | 373 pM | 81 pM | 25 nM |
| ActRIIb (SEQ ID NO: 74) | 63 pM | 23 pM | 115 pM | 278 pM |
| ActRIIa/b variant (SEQ ID NO: 69) | 542 pM | 103 pM | 186 pM | 4 nM |
| ActRIIb/a variant (SEQ ID NO: 149) | No Binding | No Binding | No Binding | No Binding |
| ActRIIa/bΔ9 variant (SEQ ID NO: 58) | 213 pM | 12.3 pM | 115 pM | 10 nM |
| ActRIIa/bΔ9 min variant (SEQ ID NO: 6) | 310 pM | 88 pM | 114 pM | 17 nM |
| ActRIIa/b+ variant (SEQ ID NO: 150) | 242 pM | 282 pM | No dissociation | 26 nM |
| ActRIIa/bΔ9m2 variant (SEQ ID NO: 38) | 170 pM | 104 pM | 222 pM | 13-18 nM |
| ActRIIa/bΔ9m3 variant (SEQ ID NO: 41) | 71 pM | 72.5 pM | 117 pM | 1.2 nM |
| ActRIIa/bΔ9m4 variant (SEQ ID NO: 44) | 375 pM | 254 pM | 394 pM | 14-20 nM |
| ActRIIa/bmax1 variant (SEQ ID NO: 70) | 232 pM | 97 pM | 236 pM | 5.6 nM |
| ActRIIa/bmax2 variant (SEQ ID NO: 71) | 135 pM | 39 pM | 113 pM | 5 nM |
| ActRIIa/bmax3 variant (SEQ ID NO: 72) | 89 pM | 43 pM | 214 pM | 3.3 nM |

*Not done in HDI, but recombinant protein demonstrates the BW result is similar to ActRIIa/b

Example 5—Effect of Extracellular ActRIIa Variants on Body and Muscle Weight

Figure 5A:
FIG. 5A is a scatter plot showing the effects of extracellular ActRIIa variants on body weight during the course of the study. Mice received a single hydrodynamic injection of a plasmid construct encoding the indicated ActRIIa variant or a control plasmid.
Figure 5B:
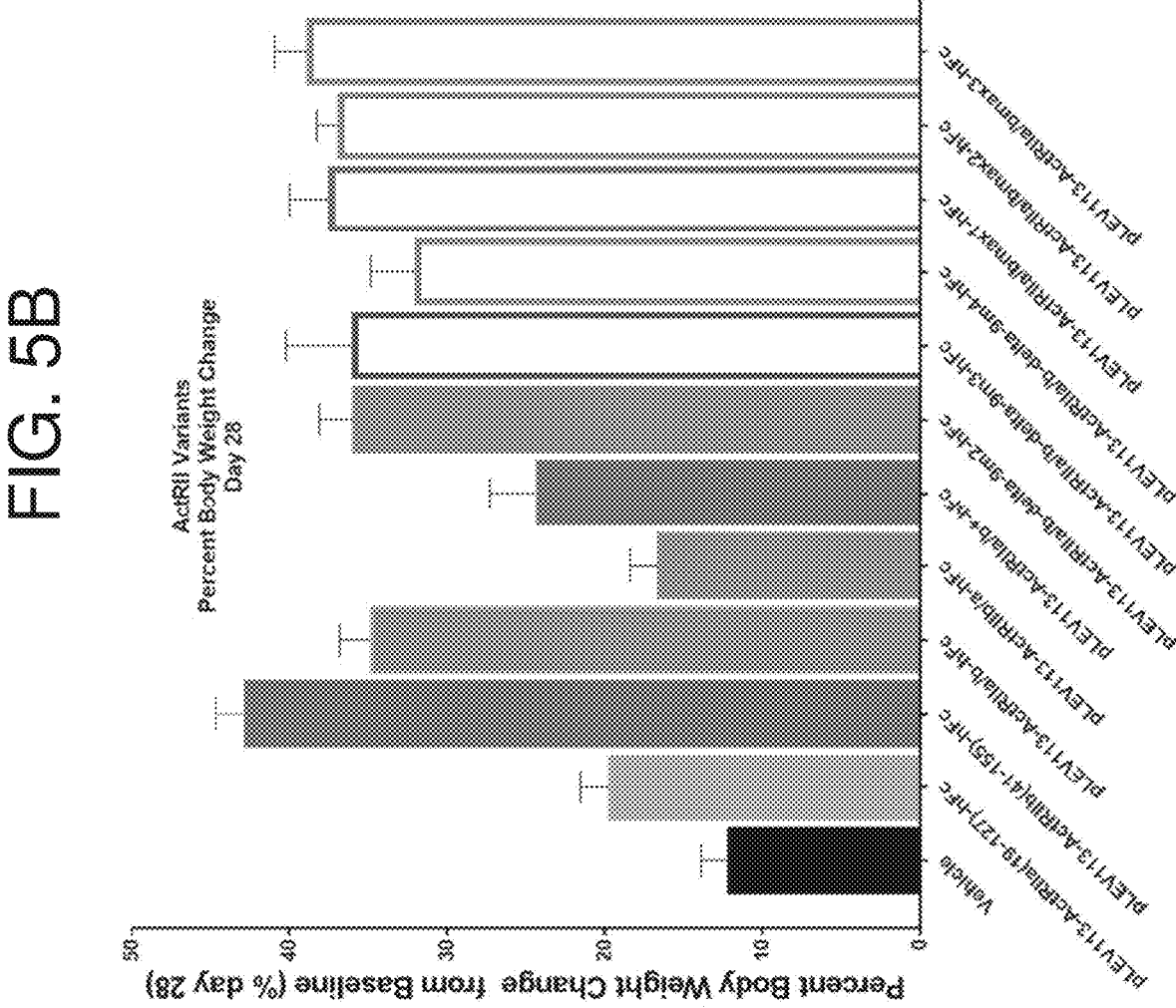
FIG. 5B is a bar graph showing the effects of extracellular ActAIIa variants on body weight at the end of 28 days.
Figure 6B:
FIGS. 6A and 6B are bar graphs showing the effects of extracellular ActRIIa variants on body weight by tissue analysis.
Figure 6B:
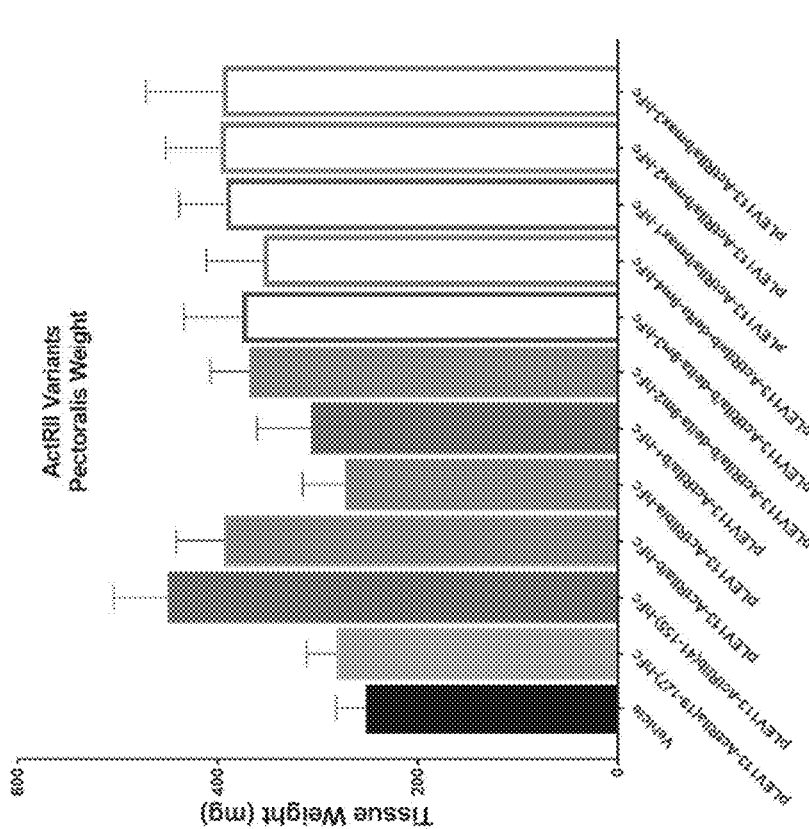
Figure 6A:
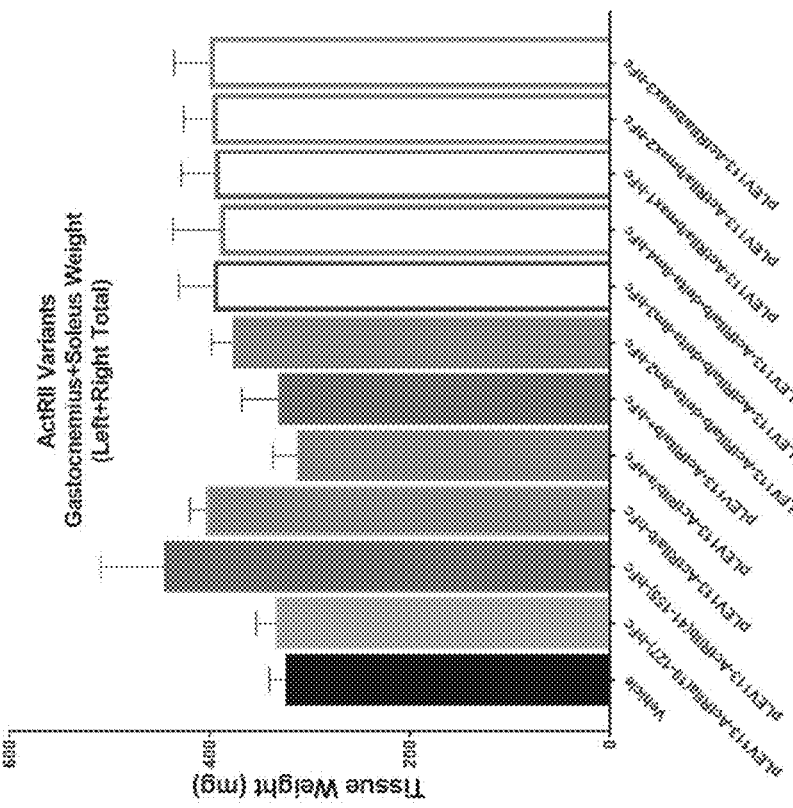

C57BI/6 mice received a single hydrodynamic injection of a plasmid construct encoding one of the following twelve polypeptides (n=10/group):

(1) vehicle;

(2) pLEV113-ActRIIa (19-127) (SEQ ID NO: 73) fused to the N-terminus of hFc through a GGG linker;

(3) pLEV113-ActRIIb (41-155) (SEQ ID NO: 74) fused to the N-terminus of hFc through a GGG linker;

(4) pLEV113-ActRIIa/b (SEQ ID NO: 69) fused to the N-terminus of hFc through a GGG linker;

(5) pLEV113-ActRII/a (SEQ ID NO: 149) fused to the N-terminus of hFc through a GGG linker;

(6) pLEV113-ActRIIa/b+ (SEQ ID NO: 150) fused to the N-terminus of hFc through a GGG linker;

ery of the liver cells and circulates freely. Mice were weighted twice weekly for 30 days and measurements were recorded as absolute body weight (BW) in grams and as a percent of body weight change from baseline measurements (FIGS. 5A and 5B, respectively). Muscles were also weighed at the end of the study and measurements were recorded in grams (FIGS. 6A and 6B).

Figure 7A:
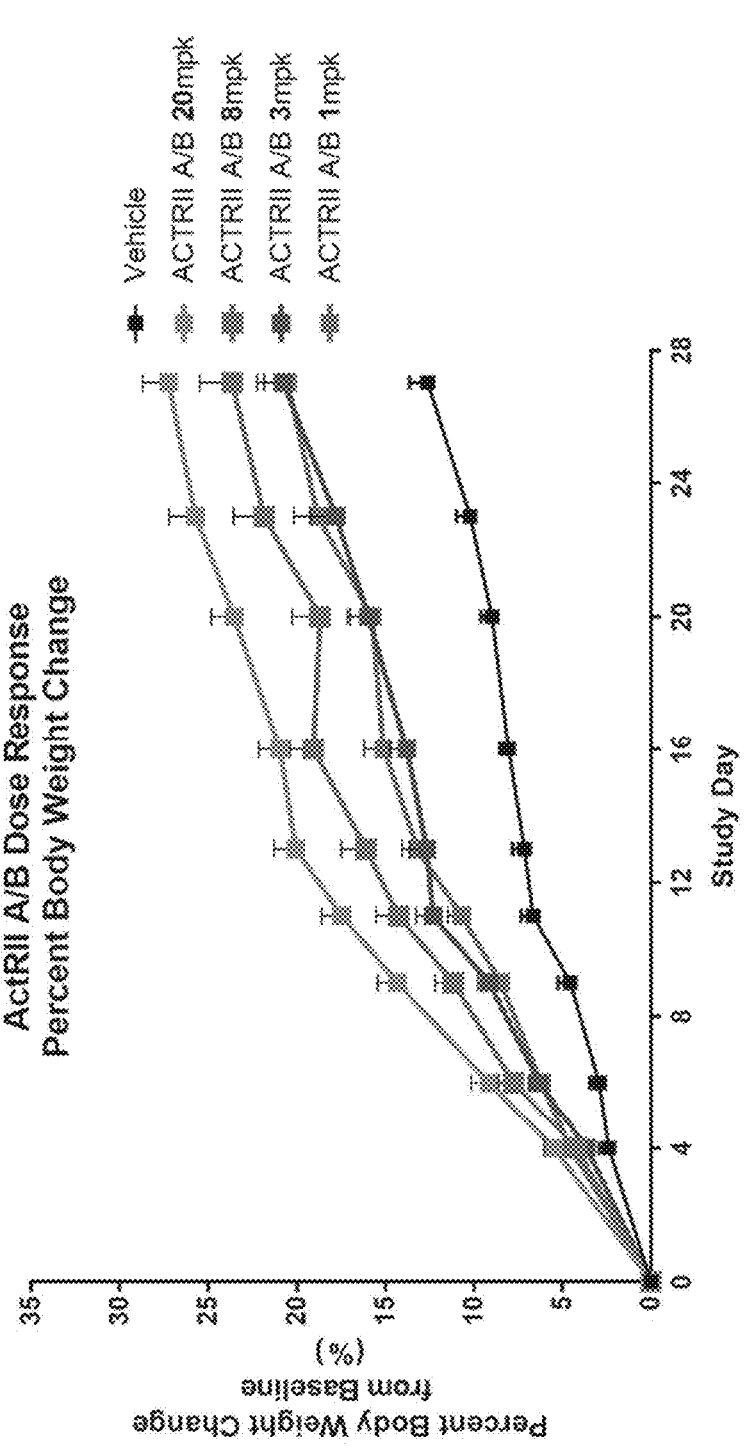
FIGS. 7A and 7B are scatter plots showing the effects of different doses of extracellular ActRIIa variants on body weight. Mice received an intraperitoneal injection of the indicated purified recombinant ActRIIa variant or a vehicle control twice weekly for four weeks.
Figure 7B:
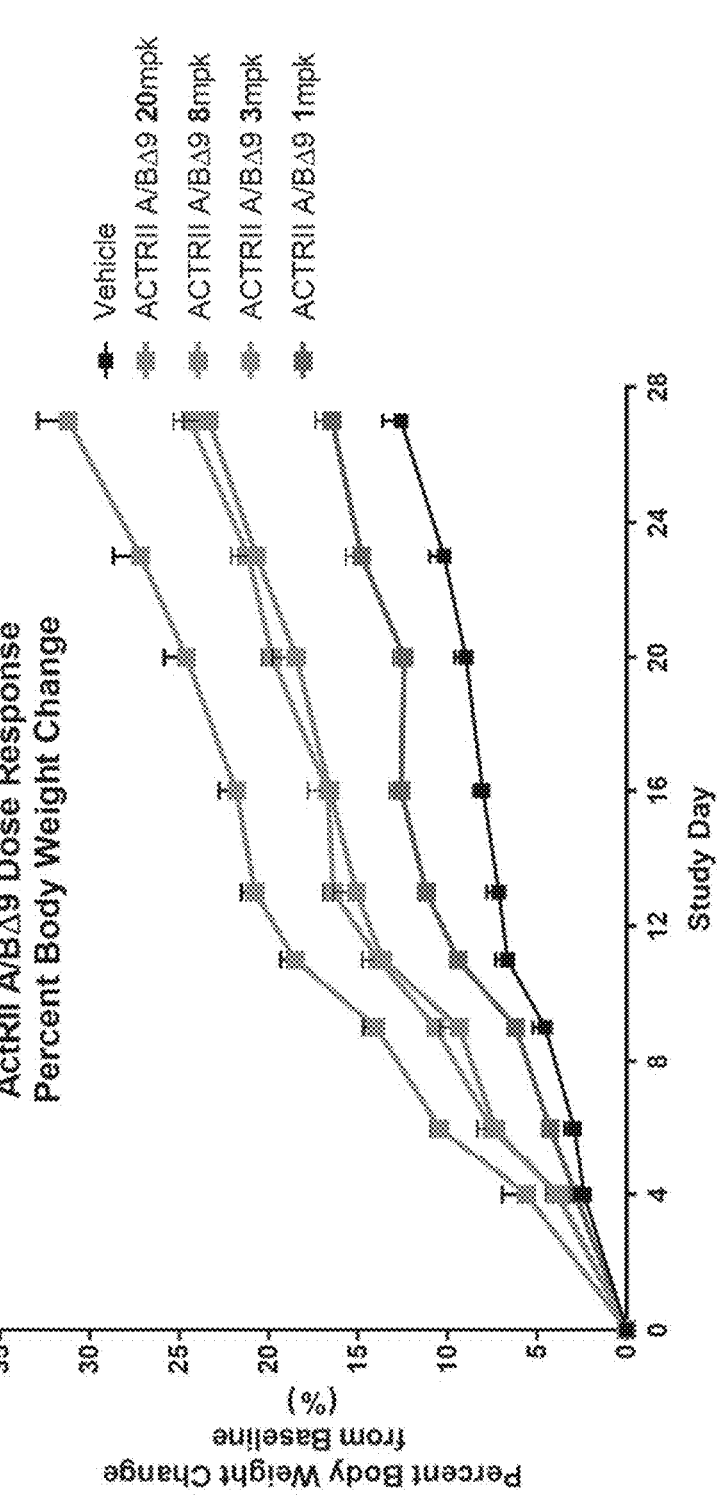
Figures 8A, 8B:
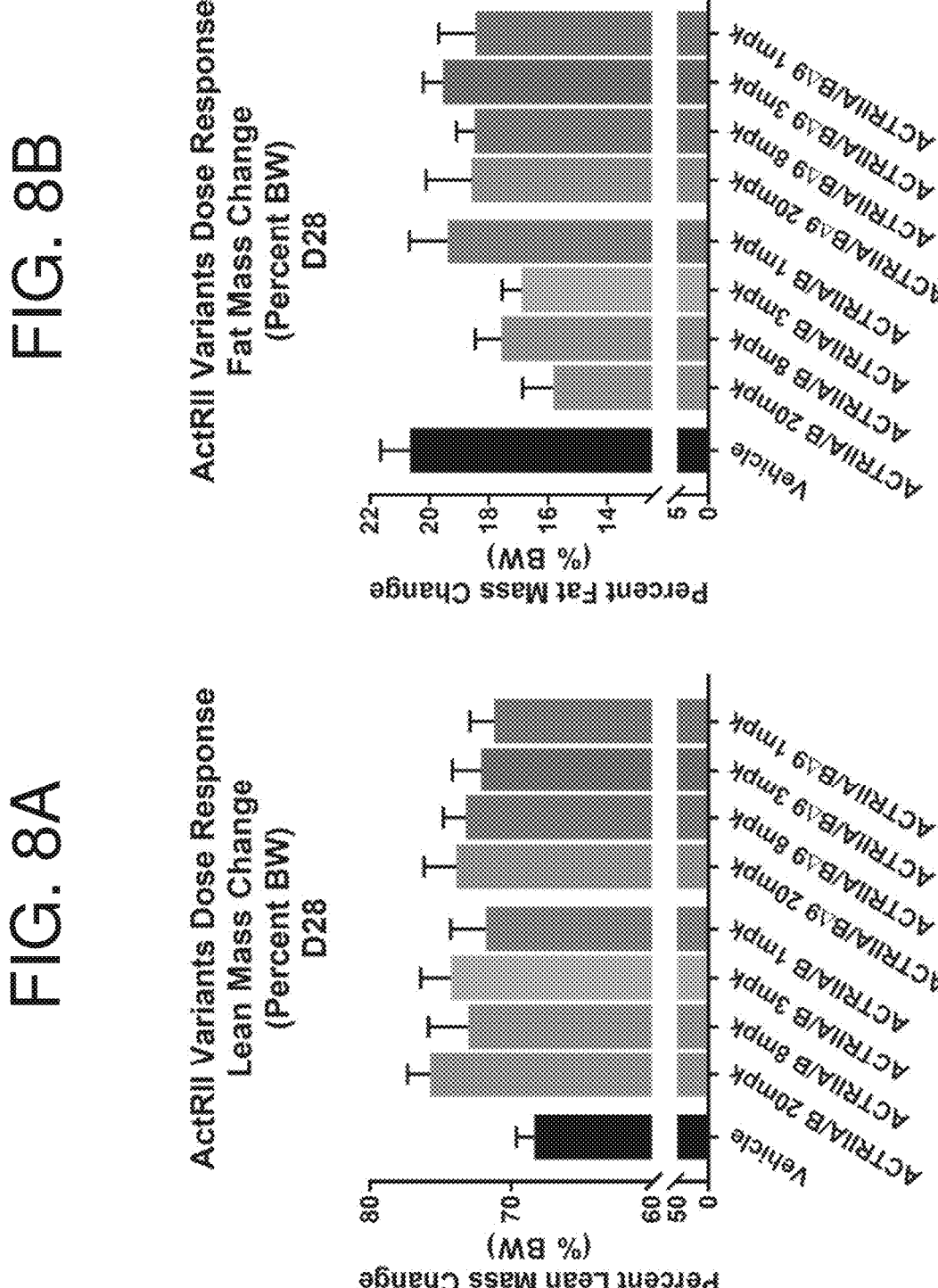
FIGS. 8A and 8B are bar graphs showing the effects of different doses of extracellular ActRIIa variants on muscle mass (FIG. 8A) and fat mass (FIG. 8B).
Figure 9B:
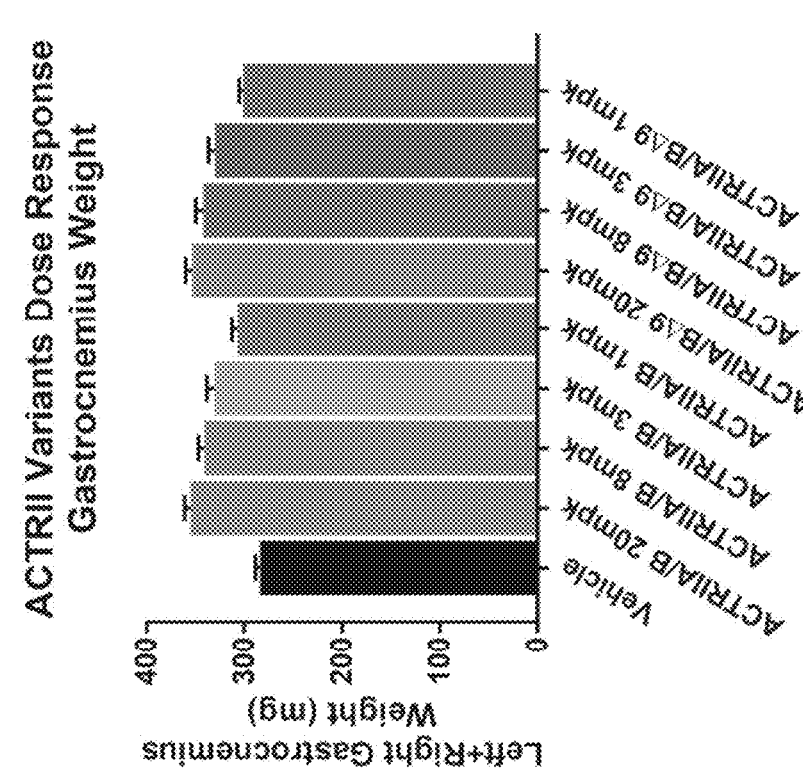
FIGS. 9A and 9B are bar graphs showing the effects of different doses of extracellular ActRIIa variants on muscle weights by tissue analysis.
Figure 9A:
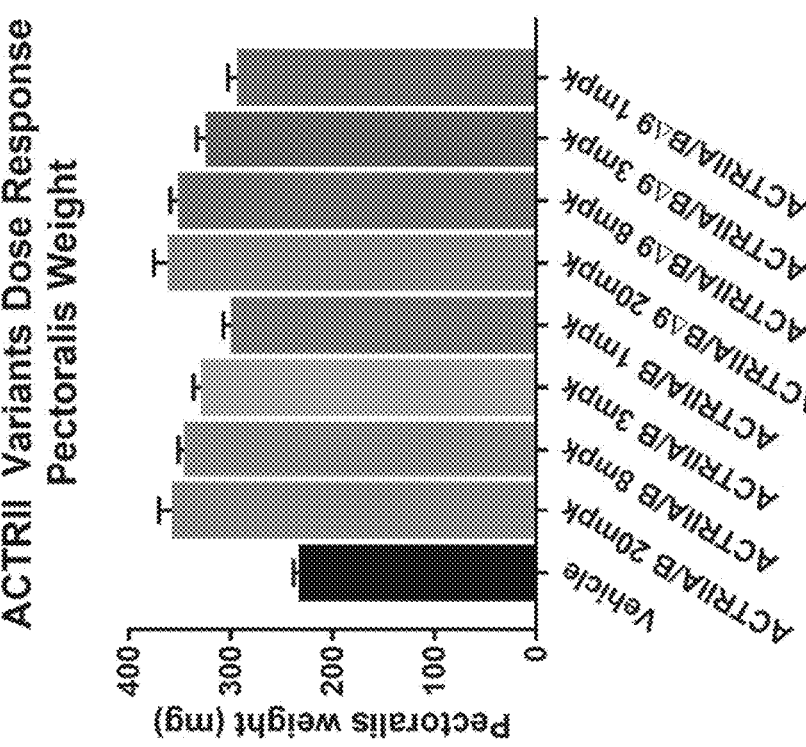

Example 6—Dose Effect of Extracellular ActRIIa Variants on Body Weight, Muscle Weight, and Muscle Mass 8-week old, male C57BL/6 mice were weight-matched into 9 groups (n=10/group). Groups were dosed with 5 mL/kg of either vehicle (Tris-Buffered Saline, pH 7.4) or one of 4 concentrations of ActRIIA/B-Fc (SEQ ID NO: 69 fused to the N-terminus of hFc through a GGG linker) or ActRIIA/BΔ9-Fc (SEQ ID NO: 58 fused to the N-terminus of hFc through a GGG linker). The doses evaluated were 20 mg/kg, 8 mg/kg, 3 mg/kg and 1 mg/kg. Treatments were administered intraperitoneally (IP) twice a week for 4 weeks (8 doses), and the study was terminated on study day 28. Body weights were recorded on dosing days throughout the study (FIGS. 7A and 7B), and at study termination, groups underwent NMR imaging for lean and fat mass analysis (FIGS. 8A and 8B) and had pectoralis and gastrocnemius muscles weights collected and weighed (FIGS. 9A and 9B).

Example 7—Effect of Extracellular ActRIIa Variants on Obesity

Adult male C57BL/6 mice are assigned to weight-matched treatment groups (n=10/group). All animals are maintained on either regular chow diet (Chow; Purina LabDiet 5001; St. Louis, MO) or high fat diet (HFD; Research Diets D12331; New Brunswick, NJ). Chow- and HFD-fed groups are further divided into groups that are dosed twice weekly with either ActRII variant or vehicle for a period of 60 d. Body weights are measured twice per week at the time of treatment. Body composition is measured using the MiniSpec LF50 at baseline (before administration of treatments and transfer to HFD) and then every other week until the end of the study. At the study termination date, tissues of interest (serum, plasma, muscles and fat depots) are surgically removed and weighed. Serum samples are subsequently evaluated for biomarkers of adiposity and plasma was evaluated for Hba1c levels.

Other Embodiments

While the invention has been described in connection with specific embodiments thereof, it will be understood that it is capable of further modifications and this application is intended to cover any variations, uses, or adaptations of the invention following, in general, the principles of the invention and including such departures from the present disclosure come within known or customary practice within the art to which the invention pertains and may be applied to the essential features hereinbefore set forth.

All publications, patents, and patent applications are herein incorporated by reference in their entirety to the same extent as if each individual publication, patent or patent application was specifically and individually indicated to be incorporated by reference in its entirety.

Other embodiments are within the following claims.

What is claimed is:

1. A polypeptide comprising, from N-terminus to C-terminus, an extracellular activin receptor type IIa (ActRIIA) variant, a linker, and an Fc domain, wherein the variant has the sequence of SEQ ID NO: 69 and the linker is a GGG linker.

2. A pharmaceutical composition comprising the polypeptide of claim 1 and a pharmaceutically acceptable excipient.

3. The polypeptide of claim 1, wherein the Fc domain is a human IgG1 Fc domain.

4. A pharmaceutical composition comprising the polypeptide of claim 3 and a pharmaceutically acceptable excipient.

5. The polypeptide of claim 1, wherein the Fc domain comprises the amino acid sequence of SEQ ID NO: 97.

6. A pharmaceutical composition comprising the polypeptide of claim 5 and a pharmaceutically acceptable excipient.

* * * * *

SEQUENCE LISTING

```
Sequence total quantity: 161
SEQ ID NO: 1              moltype = AA   length = 109
FEATURE                   Location/Qualifiers
VARIANT                   14
                          note = X is Phe or Tyr
VARIANT                   15
                          note = X is Phe or Tyr
VARIANT                   20
                          note = X is Glu or Ala
VARIANT                   21
                          note = X is Lys or Leu
VARIANT                   22
                          note = X is Asp or Glu
VARIANT                   23
                          note = X is Arg or Ala
VARIANT                   31
                          note = X is Pro or Arg
VARIANT                   33
                          note = X is Tyr or Glu
VARIANT                   35
                          note = X is Asp or Glu
VARIANT                   36
                          note = X is Lys or Gln
VARIANT                   37
                          note = X is Asp or Ala
VARIANT                   38
                          note = X is Lys or Ala
VARIANT                   39
                          note = X is Arg or Ala
VARIANT                   40
                          note = X is Arg or Leu
VARIANT                   43
                          note = X is Phe or Tyr
VARIANT                   47
                          note = X is Lys, Arg, or Ala
VARIANT                   57
                          note = X is Lys, Ala, Tyr, Phe, or Ile
VARIANT                   58
                          note = X is Gln or Lys
VARIANT                   61
                          note = X is Trp or Ala
VARIANT                   62
                          note = X is Leu or Ala
VARIANT                   63
                          note = X is Asp, Lys, Arg, Ala, Phe, Gly, Met, Asn, or Ile
VARIANT                   65
                          note = X is Ile, Phe, or Ala
VARIANT                   76
```

-continued

```
                               note = X is Lys or Thr
VARIANT                        77
                               note = X is Lys or Glu
VARIANT                        78
                               note = X is Asp or Glu
VARIANT                        79
                               note = X is Ser or Asn
VARIANT                        81
                               note = X is Glu or Gln
source                         1..109
                               mol_type = protein
                               organism = synthetic construct
SEQUENCE: 1
GAILGRSETQ ECLXXNANWX XXXTNQTGVE XCXGXXXXXX HCXATWXNIS GSIEIVXXGC   60
XXXDXNCYDR TDCVEXXXXP XVYFCCCEGN MCNEKFSYFP EMEVTQPTS              109

SEQ ID NO: 2                   moltype = AA   length = 109
FEATURE                        Location/Qualifiers
VARIANT                        15
                               note = X is Phe or Tyr
VARIANT                        20
                               note = X is Glu or Ala
VARIANT                        21
                               note = X is Lys or Leu
VARIANT                        22
                               note = X is Asp or Glu
VARIANT                        23
                               note = X is Arg or Ala
VARIANT                        31
                               note = X is Pro or Arg
VARIANT                        33
                               note = X is Tyr or Glu
VARIANT                        35
                               note = X is Asp or Glu
VARIANT                        37
                               note = X is Asp or Ala
VARIANT                        38
                               note = X is Lys or Ala
VARIANT                        39
                               note = X is Arg or Ala
VARIANT                        40
                               note = X is Arg or Leu
VARIANT                        43
                               note = X is Phe or Tyr
VARIANT                        47
                               note = X is Lys, Arg, or Ala
VARIANT                        57
                               note = X is Lys, Ala, Tyr, Phe, or Ile
VARIANT                        58
                               note = X is Gln or Lys
VARIANT                        61
                               note = X is Trp or Ala
VARIANT                        62
                               note = X is Leu or Ala
VARIANT                        63
                               note = X is Asp, Lys, Arg, Ala, Phe, Gly, Met, Asn, or Ile
VARIANT                        65
                               note = X is Ile, Phe, or Ala
VARIANT                        76
                               note = X is Lys or Thr
VARIANT                        77
                               note = X is Lys or Glu
VARIANT                        78
                               note = X is Asp or Glu
VARIANT                        79
                               note = X is Ser or Asn
VARIANT                        81
                               note = X is Glu or Gln
source                         1..109
                               mol_type = protein
                               organism = synthetic construct
SEQUENCE: 2
GAILGRSETQ ECLFXNANWX XXXTNQTGVE XCXGXKXXXX HCXATWXNIS GSIEIVXXGC   60
XXXDXNCYDR TDCVEXXXXP XVYFCCCEGN MCNEKFSYFP EMEVTQPTS              109

SEQ ID NO: 3                   moltype = AA   length = 109
FEATURE                        Location/Qualifiers
VARIANT                        15
                               note = X is Phe or Tyr
```

```
VARIANT               21
                      note = X is Lys or Leu
VARIANT               22
                      note = X is Asp or Glu
VARIANT               31
                      note = X is Pro or Arg
VARIANT               33
                      note = X is Tyr or Glu
VARIANT               35
                      note = X is Asp or Glu
VARIANT               40
                      note = X is Arg or Leu
VARIANT               43
                      note = X is Phe or Tyr
VARIANT               47
                      note = X is Lys, Arg, or Ala
VARIANT               58
                      note = X is Gln or Lys
VARIANT               65
                      note = X is Ile, Phe, or Ala
VARIANT               76
                      note = X is Lys or Thr
VARIANT               77
                      note = X is Lys or Glu
VARIANT               78
                      note = X is Asp or Glu
VARIANT               79
                      note = X is Ser or Asn
VARIANT               81
                      note = X is Glu or Gln
source                1..109
                      mol_type = protein
                      organism = synthetic construct
SEQUENCE: 3
GAILGRSETQ ECLFXNANWE XXRTNQTGVE XCXGXKDKRX HCXATWXNIS GSIEIVKXGC   60
WLDDXNCYDR TDCVEXXXXP XVYFCCCEGN MCNEKFSYFP EMEVTQPTS             109

SEQ ID NO: 4          moltype = AA  length = 109
FEATURE               Location/Qualifiers
VARIANT               15
                      note = X is Phe or Tyr
VARIANT               21
                      note = X is Lys or Leu
VARIANT               31
                      note = X is Pro or Arg
VARIANT               33
                      note = X is Tyr or Glu
VARIANT               35
                      note = X is Asp or Glu
VARIANT               40
                      note = X is Arg or Leu
VARIANT               43
                      note = X is Phe or Tyr
VARIANT               47
                      note = X is Lys, Arg, or Ala
VARIANT               58
                      note = X is Gln or Lys
VARIANT               65
                      note = X is Ile, Phe, or Ala
VARIANT               76
                      note = X is Lys or Thr
VARIANT               78
                      note = X is Asp or Glu
VARIANT               79
                      note = X is Ser or Asn
VARIANT               81
                      note = X is Glu or Gln
source                1..109
                      mol_type = protein
                      organism = synthetic construct
SEQUENCE: 4
GAILGRSETQ ECLFXNANWE XDRTNQTGVE XCXGXKDKRX HCXATWXNIS GSIEIVKXGC   60
WLDDXNCYDR TDCVEXKXXP XVYFCCCEGN MCNEKFSYFP EMEVTQPTS             109

SEQ ID NO: 5          moltype = AA  length = 109
FEATURE               Location/Qualifiers
VARIANT               15
                      note = X is Phe or Tyr
VARIANT               21
```

-continued

```
                            note = X is Lys or Leu
VARIANT                     33
                            note = X is Tyr or Glu
VARIANT                     35
                            note = X is Asp or Glu
VARIANT                     40
                            note = X is Arg or Leu
VARIANT                     58
                            note = X is Gln or Lys
VARIANT                     76
                            note = X is Lys or Thr
VARIANT                     78
                            note = X is Asp or Glu
VARIANT                     79
                            note = X is Ser or Asn
VARIANT                     81
                            note = X is Glu or Gln
source                      1..109
                            mol_type = protein
                            organism = synthetic construct
SEQUENCE: 5
GAILGRSETQ ECLFXNANWE XDRTNQTGVE PCXGXKDKRX HCFATWKNIS GSIEIVKXGC    60
WLDDINCYDR TDCVEXKXXP XVYFCCCEGN MCNEKFSYFP EMEVTQPTS                109

SEQ ID NO: 6                moltype = AA  length = 109
FEATURE                     Location/Qualifiers
source                      1..109
                            mol_type = protein
                            organism = synthetic construct
SEQUENCE: 6
GAILGRSETQ ECLFYNANWE LDRTNQTGVE PCEGEKDKRL HCFATWKNIS GSIEIVKKGC    60
WLDDINCYDR TDCVETKENP QVYFCCCEGN MCNEKFSYFP EMEVTQPTS                109

SEQ ID NO: 7                moltype = AA  length = 109
FEATURE                     Location/Qualifiers
source                      1..109
                            mol_type = protein
                            organism = synthetic construct
SEQUENCE: 7
GAILGRSETQ ECLFYNANWE LERTNQTGVE PCEGEKDKRL HCFATWKNIS GSIEIVKKGC    60
WLDDINCYDR TDCVETKENP QVYFCCCEGN MCNEKFSYFP EMEVTQPTS                109

SEQ ID NO: 8                moltype = AA  length = 109
FEATURE                     Location/Qualifiers
source                      1..109
                            mol_type = protein
                            organism = synthetic construct
SEQUENCE: 8
GAILGRSETQ ECLFYNANWE LDRTNQTGVE RCEGEKDKRL HCFATWKNIS GSIEIVKKGC    60
WLDDINCYDR TDCVETKENP QVYFCCCEGN MCNEKFSYFP EMEVTQPTS                109

SEQ ID NO: 9                moltype = AA  length = 109
FEATURE                     Location/Qualifiers
source                      1..109
                            mol_type = protein
                            organism = synthetic construct
SEQUENCE: 9
GAILGRSETQ ECLFYNANWE LDRTNQTGVE PCEGEKDKRL HCYATWKNIS GSIEIVKKGC    60
WLDDINCYDR TDCVETKENP QVYFCCCEGN MCNEKFSYFP EMEVTQPTS                109

SEQ ID NO: 10               moltype = AA  length = 109
FEATURE                     Location/Qualifiers
source                      1..109
                            mol_type = protein
                            organism = synthetic construct
SEQUENCE: 10
GAILGRSETQ ECLFYNANWE LDRTNQTGVE PCEGEKDKRL HCFATWRNIS GSIEIVKKGC    60
WLDDINCYDR TDCVETKENP QVYFCCCEGN MCNEKFSYFP EMEVTQPTS                109

SEQ ID NO: 11               moltype = AA  length = 109
FEATURE                     Location/Qualifiers
source                      1..109
                            mol_type = protein
                            organism = synthetic construct
SEQUENCE: 11
GAILGRSETQ ECLFYNANWE LDRTNQTGVE PCEGEKDKRL HCFATWKNIS GSIEIVKKGC    60
WLDDFNCYDR TDCVETKENP QVYFCCCEGN MCNEKFSYFP EMEVTQPTS                109

SEQ ID NO: 12               moltype = AA  length = 109
```

```
FEATURE                 Location/Qualifiers
source                  1..109
                        mol_type = protein
                        organism = synthetic construct
SEQUENCE: 12
GAILGRSETQ ECLFYNANWE LDRTNQTGVE PCEGEKDKRL HCFATWKNIS GSIEIVKKGC 60
WLDDINCYDR TDCVETEENP QVYFCCCEGN MCNEKFSYFP EMEVTQPTS              109

SEQ ID NO: 13           moltype = AA   length = 109
FEATURE                 Location/Qualifiers
source                  1..109
                        mol_type = protein
                        organism = synthetic construct
SEQUENCE: 13
GAILGRSETQ ECLFYNANWE LERTNQTGVE RCEGEKDKRL HCFATWKNIS GSIEIVKKGC 60
WLDDINCYDR TDCVETKENP QVYFCCCEGN MCNEKFSYFP EMEVTQPTS              109

SEQ ID NO: 14           moltype = AA   length = 109
FEATURE                 Location/Qualifiers
source                  1..109
                        mol_type = protein
                        organism = synthetic construct
SEQUENCE: 14
GAILGRSETQ ECLFYNANWE LERTNQTGVE PCEGEKDKRL HCYATWKNIS GSIEIVKKGC 60
WLDDINCYDR TDCVETKENP QVYFCCCEGN MCNEKFSYFP EMEVTQPTS              109

SEQ ID NO: 15           moltype = AA   length = 109
FEATURE                 Location/Qualifiers
source                  1..109
                        mol_type = protein
                        organism = synthetic construct
SEQUENCE: 15
GAILGRSETQ ECLFYNANWE LERTNQTGVE PCEGEKDKRL HCFATWRNIS GSIEIVKKGC 60
WLDDINCYDR TDCVETKENP QVYFCCCEGN MCNEKFSYFP EMEVTQPTS              109

SEQ ID NO: 16           moltype = AA   length = 109
FEATURE                 Location/Qualifiers
source                  1..109
                        mol_type = protein
                        organism = synthetic construct
SEQUENCE: 16
GAILGRSETQ ECLFYNANWE LERTNQTGVE PCEGEKDKRL HCFATWKNIS GSIEIVKKGC 60
WLDDFNCYDR TDCVETKENP QVYFCCCEGN MCNEKFSYFP EMEVTQPTS              109

SEQ ID NO: 17           moltype = AA   length = 109
FEATURE                 Location/Qualifiers
source                  1..109
                        mol_type = protein
                        organism = synthetic construct
SEQUENCE: 17
GAILGRSETQ ECLFYNANWE LERTNQTGVE PCEGEKDKRL HCFATWKNIS GSIEIVKKGC 60
WLDDINCYDR TDCVETEENP QVYFCCCEGN MCNEKFSYFP EMEVTQPTS              109

SEQ ID NO: 18           moltype = AA   length = 109
FEATURE                 Location/Qualifiers
source                  1..109
                        mol_type = protein
                        organism = synthetic construct
SEQUENCE: 18
GAILGRSETQ ECLFYNANWE LDRTNQTGVE RCEGEKDKRL HCYATWKNIS GSIEIVKKGC 60
WLDDINCYDR TDCVETKENP QVYFCCCEGN MCNEKFSYFP EMEVTQPTS              109

SEQ ID NO: 19           moltype = AA   length = 109
FEATURE                 Location/Qualifiers
source                  1..109
                        mol_type = protein
                        organism = synthetic construct
SEQUENCE: 19
GAILGRSETQ ECLFYNANWE LDRTNQTGVE RCEGEKDKRL HCFATWRNIS GSIEIVKKGC 60
WLDDINCYDR TDCVETKENP QVYFCCCEGN MCNEKFSYFP EMEVTQPTS              109

SEQ ID NO: 20           moltype = AA   length = 109
FEATURE                 Location/Qualifiers
source                  1..109
                        mol_type = protein
                        organism = synthetic construct
SEQUENCE: 20
GAILGRSETQ ECLFYNANWE LDRTNQTGVE RCEGEKDKRL HCFATWKNIS GSIEIVKKGC 60
WLDDFNCYDR TDCVETKENP QVYFCCCEGN MCNEKFSYFP EMEVTQPTS              109
```

```
SEQ ID NO: 21              moltype = AA  length = 109
FEATURE                    Location/Qualifiers
source                     1..109
                           mol_type = protein
                           organism = synthetic construct
SEQUENCE: 21
GAILGRSETQ ECLFYNANWE LDRTNQTGVE RCEGEKDKRL HCFATWKNIS GSIEIVKKGC  60
WLDDINCYDR TDCVETEENP QVYFCCCEGN MCNEKFSYFP EMEVTQPTS              109

SEQ ID NO: 22              moltype = AA  length = 109
FEATURE                    Location/Qualifiers
source                     1..109
                           mol_type = protein
                           organism = synthetic construct
SEQUENCE: 22
GAILGRSETQ ECLFYNANWE LDRTNQTGVE PCEGEKDKRL HCYATWRNIS GSIEIVKKGC  60
WLDDINCYDR TDCVETKENP QVYFCCCEGN MCNEKFSYFP EMEVTQPTS              109

SEQ ID NO: 23              moltype = AA  length = 109
FEATURE                    Location/Qualifiers
source                     1..109
                           mol_type = protein
                           organism = synthetic construct
SEQUENCE: 23
GAILGRSETQ ECLFYNANWE LDRTNQTGVE PCEGEKDKRL HCYATWKNIS GSIEIVKKGC  60
WLDDFNCYDR TDCVETKENP QVYFCCCEGN MCNEKFSYFP EMEVTQPTS              109

SEQ ID NO: 24              moltype = AA  length = 109
FEATURE                    Location/Qualifiers
source                     1..109
                           mol_type = protein
                           organism = synthetic construct
SEQUENCE: 24
GAILGRSETQ ECLFYNANWE LDRTNQTGVE PCEGEKDKRL HCYATWKNIS GSIEIVKKGC  60
WLDDINCYDR TDCVETEENP QVYFCCCEGN MCNEKFSYFP EMEVTQPTS              109

SEQ ID NO: 25              moltype = AA  length = 109
FEATURE                    Location/Qualifiers
source                     1..109
                           mol_type = protein
                           organism = synthetic construct
SEQUENCE: 25
GAILGRSETQ ECLFYNANWE LDRTNQTGVE PCEGEKDKRL HCFATWRNIS GSIEIVKKGC  60
WLDDFNCYDR TDCVETKENP QVYFCCCEGN MCNEKFSYFP EMEVTQPTS              109

SEQ ID NO: 26              moltype = AA  length = 109
FEATURE                    Location/Qualifiers
source                     1..109
                           mol_type = protein
                           organism = synthetic construct
SEQUENCE: 26
GAILGRSETQ ECLFYNANWE LDRTNQTGVE PCEGEKDKRL HCFATWRNIS GSIEIVKKGC  60
WLDDINCYDR TDCVETEENP QVYFCCCEGN MCNEKFSYFP EMEVTQPTS              109

SEQ ID NO: 27              moltype = AA  length = 109
FEATURE                    Location/Qualifiers
source                     1..109
                           mol_type = protein
                           organism = synthetic construct
SEQUENCE: 27
GAILGRSETQ ECLFYNANWE LDRTNQTGVE PCEGEKDKRL HCFATWKNIS GSIEIVKKGC  60
WLDDFNCYDR TDCVETEENP QVYFCCCEGN MCNEKFSYFP EMEVTQPTS              109

SEQ ID NO: 28              moltype = AA  length = 109
FEATURE                    Location/Qualifiers
source                     1..109
                           mol_type = protein
                           organism = synthetic construct
SEQUENCE: 28
GAILGRSETQ ECLFYNANWE LERTNQTGVE RCEGEKDKRL HCYATWKNIS GSIEIVKKGC  60
WLDDINCYDR TDCVETKENP QVYFCCCEGN MCNEKFSYFP EMEVTQPTS              109

SEQ ID NO: 29              moltype = AA  length = 109
FEATURE                    Location/Qualifiers
source                     1..109
                           mol_type = protein
                           organism = synthetic construct
SEQUENCE: 29
```

```
GAILGRSETQ ECLFYNANWE LERTNQTGVE RCEGEKDKRL HCFATWRNIS GSIEIVKKGC   60
WLDDINCYDR TDCVETKENP QVYFCCCEGN MCNEKFSYFP EMEVTQPTS               109

SEQ ID NO: 30                moltype = AA  length = 109
FEATURE                      Location/Qualifiers
source                       1..109
                             mol_type = protein
                             organism = synthetic construct
SEQUENCE: 30
GAILGRSETQ ECLFYNANWE LERTNQTGVE RCEGEKDKRL HCFATWKNIS GSIEIVKKGC   60
WLDDFNCYDR TDCVETKENP QVYFCCCEGN MCNEKFSYFP EMEVTQPTS               109

SEQ ID NO: 31                moltype = AA  length = 109
FEATURE                      Location/Qualifiers
source                       1..109
                             mol_type = protein
                             organism = synthetic construct
SEQUENCE: 31
GAILGRSETQ ECLFYNANWE LERTNQTGVE RCEGEKDKRL HCFATWKNIS GSIEIVKKGC   60
WLDDINCYDR TDCVETEENP QVYFCCCEGN MCNEKFSYFP EMEVTQPTS               109

SEQ ID NO: 32                moltype = AA  length = 109
FEATURE                      Location/Qualifiers
source                       1..109
                             mol_type = protein
                             organism = synthetic construct
SEQUENCE: 32
GAILGRSETQ ECLFYNANWE LERTNQTGVE PCEGEKDKRL HCYATWRNIS GSIEIVKKGC   60
WLDDINCYDR TDCVETKENP QVYFCCCEGN MCNEKFSYFP EMEVTQPTS               109

SEQ ID NO: 33                moltype = AA  length = 109
FEATURE                      Location/Qualifiers
source                       1..109
                             mol_type = protein
                             organism = synthetic construct
SEQUENCE: 33
GAILGRSETQ ECLFYNANWE LERTNQTGVE PCEGEKDKRL HCYATWKNIS GSIEIVKKGC   60
WLDDFNCYDR TDCVETKENP QVYFCCCEGN MCNEKFSYFP EMEVTQPTS               109

SEQ ID NO: 34                moltype = AA  length = 109
FEATURE                      Location/Qualifiers
source                       1..109
                             mol_type = protein
                             organism = synthetic construct
SEQUENCE: 34
GAILGRSETQ ECLFYNANWE LERTNQTGVE PCEGEKDKRL HCYATWKNIS GSIEIVKKGC   60
WLDDINCYDR TDCVETEENP QVYFCCCEGN MCNEKFSYFP EMEVTQPTS               109

SEQ ID NO: 35                moltype = AA  length = 109
FEATURE                      Location/Qualifiers
source                       1..109
                             mol_type = protein
                             organism = synthetic construct
SEQUENCE: 35
GAILGRSETQ ECLFYNANWE LERTNQTGVE PCEGEKDKRL HCFATWRNIS GSIEIVKKGC   60
WLDDFNCYDR TDCVETKENP QVYFCCCEGN MCNEKFSYFP EMEVTQPTS               109

SEQ ID NO: 36                moltype = AA  length = 109
FEATURE                      Location/Qualifiers
source                       1..109
                             mol_type = protein
                             organism = synthetic construct
SEQUENCE: 36
GAILGRSETQ ECLFYNANWE LERTNQTGVE PCEGEKDKRL HCFATWRNIS GSIEIVKKGC   60
WLDDINCYDR TDCVETEENP QVYFCCCEGN MCNEKFSYFP EMEVTQPTS               109

SEQ ID NO: 37                moltype = AA  length = 109
FEATURE                      Location/Qualifiers
source                       1..109
                             mol_type = protein
                             organism = synthetic construct
SEQUENCE: 37
GAILGRSETQ ECLFYNANWE LERTNQTGVE PCEGEKDKRL HCFATWKNIS GSIEIVKKGC   60
WLDDFNCYDR TDCVETEENP QVYFCCCEGN MCNEKFSYFP EMEVTQPTS               109

SEQ ID NO: 38                moltype = AA  length = 109
FEATURE                      Location/Qualifiers
source                       1..109
                             mol_type = protein
```

```
                             organism = synthetic construct
SEQUENCE: 38
GAILGRSETQ ECLFYNANWE LDRTNQTGVE RCEGEKDKRL HCYATWRNIS GSIEIVKKGC    60
WLDDINCYDR TDCVETKENP QVYFCCCEGN MCNEKFSYFP EMEVTQPTS              109

SEQ ID NO: 39             moltype = AA   length = 109
FEATURE                   Location/Qualifiers
source                    1..109
                          mol_type = protein
                          organism = synthetic construct
SEQUENCE: 39
GAILGRSETQ ECLFYNANWE LDRTNQTGVE RCEGEKDKRL HCYATWKNIS GSIEIVKKGC    60
WLDDFNCYDR TDCVETKENP QVYFCCCEGN MCNEKFSYFP EMEVTQPTS              109

SEQ ID NO: 40             moltype = AA   length = 109
FEATURE                   Location/Qualifiers
source                    1..109
                          mol_type = protein
                          organism = synthetic construct
SEQUENCE: 40
GAILGRSETQ ECLFYNANWE LDRTNQTGVE RCEGEKDKRL HCYATWKNIS GSIEIVKKGC    60
WLDDINCYDR TDCVETEENP QVYFCCCEGN MCNEKFSYFP EMEVTQPTS              109

SEQ ID NO: 41             moltype = AA   length = 109
FEATURE                   Location/Qualifiers
source                    1..109
                          mol_type = protein
                          organism = synthetic construct
SEQUENCE: 41
GAILGRSETQ ECLFYNANWE LDRTNQTGVE RCEGEKDKRL HCFATWRNIS GSIEIVKKGC    60
WLDDFNCYDR TDCVETKENP QVYFCCCEGN MCNEKFSYFP EMEVTQPTS              109

SEQ ID NO: 42             moltype = AA   length = 109
FEATURE                   Location/Qualifiers
source                    1..109
                          mol_type = protein
                          organism = synthetic construct
SEQUENCE: 42
GAILGRSETQ ECLFYNANWE LDRTNQTGVE RCEGEKDKRL HCFATWRNIS GSIEIVKKGC    60
WLDDINCYDR TDCVETEENP QVYFCCCEGN MCNEKFSYFP EMEVTQPTS              109

SEQ ID NO: 43             moltype = AA   length = 109
FEATURE                   Location/Qualifiers
source                    1..109
                          mol_type = protein
                          organism = synthetic construct
SEQUENCE: 43
GAILGRSETQ ECLFYNANWE LDRTNQTGVE RCEGEKDKRL HCFATWKNIS GSIEIVKKGC    60
WLDDFNCYDR TDCVETEENP QVYFCCCEGN MCNEKFSYFP EMEVTQPTS              109

SEQ ID NO: 44             moltype = AA   length = 109
FEATURE                   Location/Qualifiers
source                    1..109
                          mol_type = protein
                          organism = synthetic construct
SEQUENCE: 44
GAILGRSETQ ECLFYNANWE LDRTNQTGVE PCEGEKDKRL HCYATWRNIS GSIEIVKKGC    60
WLDDFNCYDR TDCVETKENP QVYFCCCEGN MCNEKFSYFP EMEVTQPTS              109

SEQ ID NO: 45             moltype = AA   length = 109
FEATURE                   Location/Qualifiers
source                    1..109
                          mol_type = protein
                          organism = synthetic construct
SEQUENCE: 45
GAILGRSETQ ECLFYNANWE LDRTNQTGVE PCEGEKDKRL HCYATWRNIS GSIEIVKKGC    60
WLDDINCYDR TDCVETEENP QVYFCCCEGN MCNEKFSYFP EMEVTQPTS              109

SEQ ID NO: 46             moltype = AA   length = 109
FEATURE                   Location/Qualifiers
source                    1..109
                          mol_type = protein
                          organism = synthetic construct
SEQUENCE: 46
GAILGRSETQ ECLFYNANWE LDRTNQTGVE PCEGEKDKRL HCYATWKNIS GSIEIVKKGC    60
WLDDFNCYDR TDCVETEENP QVYFCCCEGN MCNEKFSYFP EMEVTQPTS              109

SEQ ID NO: 47             moltype = AA   length = 109
FEATURE                   Location/Qualifiers
```

```
source                    1..109
                          mol_type = protein
                          organism = synthetic construct
SEQUENCE: 47
GAILGRSETQ ECLFYNANWE LDRTNQTGVE PCEGEKDKRL HCFATWRNIS GSIEIVKKGC  60
WLDDFNCYDR TDCVETEENP QVYFCCCEGN MCNEKFSYFP EMEVTQPTS              109

SEQ ID NO: 48            moltype = AA   length = 109
FEATURE                  Location/Qualifiers
source                   1..109
                         mol_type = protein
                         organism = synthetic construct
SEQUENCE: 48
GAILGRSETQ ECLFYNANWE LERTNQTGVE RCEGEKDKRL HCYATWRNIS GSIEIVKKGC  60
WLDDINCYDR TDCVETKENP QVYFCCCEGN MCNEKFSYFP EMEVTQPTS              109

SEQ ID NO: 49            moltype = AA   length = 109
FEATURE                  Location/Qualifiers
source                   1..109
                         mol_type = protein
                         organism = synthetic construct
SEQUENCE: 49
GAILGRSETQ ECLFYNANWE LERTNQTGVE RCEGEKDKRL HCYATWKNIS GSIEIVKKGC  60
WLDDFNCYDR TDCVETKENP QVYFCCCEGN MCNEKFSYFP EMEVTQPTS              109

SEQ ID NO: 50            moltype = AA   length = 109
FEATURE                  Location/Qualifiers
source                   1..109
                         mol_type = protein
                         organism = synthetic construct
SEQUENCE: 50
GAILGRSETQ ECLFYNANWE LERTNQTGVE RCEGEKDKRL HCYATWKNIS GSIEIVKKGC  60
WLDDINCYDR TDCVETEENP QVYFCCCEGN MCNEKFSYFP EMEVTQPTS              109

SEQ ID NO: 51            moltype = AA   length = 109
FEATURE                  Location/Qualifiers
source                   1..109
                         mol_type = protein
                         organism = synthetic construct
SEQUENCE: 51
GAILGRSETQ ECLFYNANWE LERTNQTGVE RCEGEKDKRL HCFATWRNIS GSIEIVKKGC  60
WLDDFNCYDR TDCVETKENP QVYFCCCEGN MCNEKFSYFP EMEVTQPTS              109

SEQ ID NO: 52            moltype = AA   length = 109
FEATURE                  Location/Qualifiers
source                   1..109
                         mol_type = protein
                         organism = synthetic construct
SEQUENCE: 52
GAILGRSETQ ECLFYNANWE LERTNQTGVE RCEGEKDKRL HCFATWRNIS GSIEIVKKGC  60
WLDDINCYDR TDCVETEENP QVYFCCCEGN MCNEKFSYFP EMEVTQPTS              109

SEQ ID NO: 53            moltype = AA   length = 109
FEATURE                  Location/Qualifiers
source                   1..109
                         mol_type = protein
                         organism = synthetic construct
SEQUENCE: 53
GAILGRSETQ ECLFYNANWE LERTNQTGVE RCEGEKDKRL HCFATWKNIS GSIEIVKKGC  60
WLDDFNCYDR TDCVETEENP QVYFCCCEGN MCNEKFSYFP EMEVTQPTS              109

SEQ ID NO: 54            moltype = AA   length = 109
FEATURE                  Location/Qualifiers
source                   1..109
                         mol_type = protein
                         organism = synthetic construct
SEQUENCE: 54
GAILGRSETQ ECLFYNANWE LERTNQTGVE PCEGEKDKRL HCYATWRNIS GSIEIVKKGC  60
WLDDFNCYDR TDCVETKENP QVYFCCCEGN MCNEKFSYFP EMEVTQPTS              109

SEQ ID NO: 55            moltype = AA   length = 109
FEATURE                  Location/Qualifiers
source                   1..109
                         mol_type = protein
                         organism = synthetic construct
SEQUENCE: 55
GAILGRSETQ ECLFYNANWE LERTNQTGVE PCEGEKDKRL HCYATWRNIS GSIEIVKKGC  60
WLDDINCYDR TDCVETEENP QVYFCCCEGN MCNEKFSYFP EMEVTQPTS              109
```

-continued

```
SEQ ID NO: 56            moltype = AA  length = 109
FEATURE                  Location/Qualifiers
source                   1..109
                         mol_type = protein
                         organism = synthetic construct
SEQUENCE: 56
GAILGRSETQ ECLFYNANWE LERTNQTGVE PCEGEKDKRL HCYATWKNIS GSIEIVKKGC  60
WLDDFNCYDR TDCVETEENP QVYFCCCEGN MCNEKFSYFP EMEVTQPTS             109

SEQ ID NO: 57            moltype = AA  length = 109
FEATURE                  Location/Qualifiers
source                   1..109
                         mol_type = protein
                         organism = synthetic construct
SEQUENCE: 57
GAILGRSETQ ECLFYNANWE LERTNQTGVE PCEGEKDKRL HCFATWRNIS GSIEIVKKGC  60
WLDDFNCYDR TDCVETEENP QVYFCCCEGN MCNEKFSYFP EMEVTQPTS             109

SEQ ID NO: 58            moltype = AA  length = 109
FEATURE                  Location/Qualifiers
source                   1..109
                         mol_type = protein
                         organism = synthetic construct
SEQUENCE: 58
GAILGRSETQ ECLFYNANWE LDRTNQTGVE RCEGEKDKRL HCYATWRNIS GSIEIVKKGC  60
WLDDFNCYDR TDCVETKENP QVYFCCCEGN MCNEKFSYFP EMEVTQPTS             109

SEQ ID NO: 59            moltype = AA  length = 109
FEATURE                  Location/Qualifiers
source                   1..109
                         mol_type = protein
                         organism = synthetic construct
SEQUENCE: 59
GAILGRSETQ ECLFYNANWE LDRTNQTGVE RCEGEKDKRL HCYATWKNIS GSIEIVKKGC  60
WLDDINCYDR TDCVETEENP QVYFCCCEGN MCNEKFSYFP EMEVTQPTS             109

SEQ ID NO: 60            moltype = AA  length = 109
FEATURE                  Location/Qualifiers
source                   1..109
                         mol_type = protein
                         organism = synthetic construct
SEQUENCE: 60
GAILGRSETQ ECLFYNANWE LDRTNQTGVE RCEGEKDKRL HCYATWKNIS GSIEIVKKGC  60
WLDDFNCYDR TDCVETEENP QVYFCCCEGN MCNEKFSYFP EMEVTQPTS             109

SEQ ID NO: 61            moltype = AA  length = 109
FEATURE                  Location/Qualifiers
source                   1..109
                         mol_type = protein
                         organism = synthetic construct
SEQUENCE: 61
GAILGRSETQ ECLFYNANWE LDRTNQTGVE RCEGEKDKRL HCFATWRNIS GSIEIVKKGC  60
WLDDFNCYDR TDCVETEENP QVYFCCCEGN MCNEKFSYFP EMEVTQPTS             109

SEQ ID NO: 62            moltype = AA  length = 109
FEATURE                  Location/Qualifiers
source                   1..109
                         mol_type = protein
                         organism = synthetic construct
SEQUENCE: 62
GAILGRSETQ ECLFYNANWE LDRTNQTGVE PCEGEKDKRL HCYATWRNIS GSIEIVKKGC  60
WLDDFNCYDR TDCVETEENP QVYFCCCEGN MCNEKFSYFP EMEVTQPTS             109

SEQ ID NO: 63            moltype = AA  length = 109
FEATURE                  Location/Qualifiers
source                   1..109
                         mol_type = protein
                         organism = synthetic construct
SEQUENCE: 63
GAILGRSETQ ECLFYNANWE LERTNQTGVE RCEGEKDKRL HCYATWRNIS GSIEIVKKGC  60
WLDDFNCYDR TDCVETKENP QVYFCCCEGN MCNEKFSYFP EMEVTQPTS             109

SEQ ID NO: 64            moltype = AA  length = 109
FEATURE                  Location/Qualifiers
source                   1..109
                         mol_type = protein
                         organism = synthetic construct
SEQUENCE: 64
GAILGRSETQ ECLFYNANWE LERTNQTGVE RCEGEKDKRL HCYATWRNIS GSIEIVKKGC  60
```

-continued

```
WLDDINCYDR TDCVETEENP QVYFCCCEGN MCNEKFSYFP EMEVTQPTS            109

SEQ ID NO: 65              moltype = AA  length = 109
FEATURE                    Location/Qualifiers
source                     1..109
                           mol_type = protein
                           organism = synthetic construct
SEQUENCE: 65
GAILGRSETQ ECLFYNANWE LERTNQTGVE RCEGEKDKRL HCYATWKNIS GSIEIVKKGC  60
WLDDFNCYDR TDCVETEENP QVYFCCCEGN MCNEKFSYFP EMEVTQPTS            109

SEQ ID NO: 66              moltype = AA  length = 109
FEATURE                    Location/Qualifiers
source                     1..109
                           mol_type = protein
                           organism = synthetic construct
SEQUENCE: 66
GAILGRSETQ ECLFYNANWE LERTNQTGVE RCEGEKDKRL HCFATWRNIS GSIEIVKKGC  60
WLDDFNCYDR TDCVETEENP QVYFCCCEGN MCNEKFSYFP EMEVTQPTS            109

SEQ ID NO: 67              moltype = AA  length = 109
FEATURE                    Location/Qualifiers
source                     1..109
                           mol_type = protein
                           organism = synthetic construct
SEQUENCE: 67
GAILGRSETQ ECLFYNANWE LDRTNQTGVE RCEGEKDKRL HCYATWRNIS GSIEIVKKGC  60
WLDDFNCYDR TDCVETEENP QVYFCCCEGN MCNEKFSYFP EMEVTQPTS            109

SEQ ID NO: 68              moltype = AA  length = 109
FEATURE                    Location/Qualifiers
source                     1..109
                           mol_type = protein
                           organism = synthetic construct
SEQUENCE: 68
GAILGRSETQ ECLFYNANWE LERTNQTGVE PCEGEKDKRL HCYATWRNIS GSIEIVKKGC  60
WLDDFNCYDR TDCVETEENP QVYFCCCEGN MCNEKFSYFP EMEVTQPTS            109

SEQ ID NO: 69              moltype = AA  length = 109
FEATURE                    Location/Qualifiers
source                     1..109
                           mol_type = protein
                           organism = synthetic construct
SEQUENCE: 69
GAILGRSETQ ECLFYNANWE LERTNQTGVE RCEGEKDKRL HCYATWRNIS GSIEIVKKGC  60
WLDDFNCYDR TDCVETEENP QVYFCCCEGN MCNEKFSYFP EMEVTQPTS            109

SEQ ID NO: 70              moltype = AA  length = 109
FEATURE                    Location/Qualifiers
source                     1..109
                           mol_type = protein
                           organism = synthetic construct
SEQUENCE: 70
GAILGRSETQ ECLYYNANWE LERTNQTGVE RCEGEQDKRL HCYATWRNIS GSIEIVKKGC  60
WLDDFNCYDR TDCVETEENP QVYFCCCEGN MCNEKFSYFP EMEVTQPTS            109

SEQ ID NO: 71              moltype = AA  length = 111
FEATURE                    Location/Qualifiers
source                     1..111
                           mol_type = protein
                           organism = synthetic construct
SEQUENCE: 71
GAILGRSETQ ECLFYNANWE LERTNQTGVE RCEGEKDKRL HCYATWRNIS GSIEIVKKGC  60
WLDDFNCYDR TDCVETEENP QVYFCCCEGN MCNEKFSYFP EMEVTQPTSN P          111

SEQ ID NO: 72              moltype = AA  length = 115
FEATURE                    Location/Qualifiers
source                     1..115
                           mol_type = protein
                           organism = synthetic construct
SEQUENCE: 72
GAILGRSETQ ECLFYNANWE LERTNQTGVE RCEGEKDKRL HCYATWRNIS GSIEIVKKGC  60
WLDDFNCYDR TDCVETEENP QVYFCCCEGN MCNEKFSYFP EMEVTQPTSN PVTPK      115

SEQ ID NO: 73              moltype = AA  length = 109
FEATURE                    Location/Qualifiers
source                     1..109
                           mol_type = protein
                           organism = Homo sapiens
```

```
SEQUENCE: 73
GAILGRSETQ ECLFFNANWE KDRTNQTGVE PCYGDKDKRR HCFATWKNIS GSIEIVKQGC  60
WLDDINCYDR TDCVEKKDSP EVYFCCCEGN MCNEKFSYFP EMEVTQPTS             109

SEQ ID NO: 74              moltype = AA   length = 115
FEATURE                    Location/Qualifiers
source                     1..115
                           mol_type = protein
                           organism = Homo sapiens
SEQUENCE: 74
GRGEAETREC IYYNANWELE RTNQSGLERC EGEQDKRLHC YASWRNSSGT IELVKKGCWL  60
DDFNCYDRQE CVATEENPQV YFCCCEGNFC NERFTHLPEA GGPEVTYEPP PTAPT       115

SEQ ID NO: 75              moltype = AA   length = 513
FEATURE                    Location/Qualifiers
source                     1..513
                           mol_type = protein
                           organism = Homo sapiens
SEQUENCE: 75
MGAAAKLAFA VFLISCSSGA ILGRSETQEC LFFNANWEKD RTNQTGVEPC YGDKDKRRHC  60
FATWKNISGS IEIVKQGCWL DDINCYDRTD CVEKKDSPEV YFCCCEGNMC NEKFSYFPEM  120
EVTQPTSNPV TPKPPYYNIL LYSLVPLMLI AGIVICAFWV YRHHKMAYPP VLVPTQDPGP  180
PPPSPLLGLK PLQLLEVKAR GRFGCVWKAQ LLNEYVAVKI FPIQDKQSWQ NEYEVYSLPG  240
MKHENILQFI GAEKRGTSVD VDLWLITAFH EKGSLSDFLK ANVVSWNELC HIAETMARGL  300
AYLHEDIPGL KDGHKPAISH RDIKSKNVLL KNNLTACIAD FGLALKFEAG KSAGDTHGQV  360
GTRRYMAPEV LEGAINFQRD AFLRIDMYAM GLVLWELASR CTAADGPVDE YMLPFEEEIG  420
QHPSLEDMQE VVVHKKKRPV LRDYWQKHAG MAMLCETIEE CWDHDAEARL SAGCVGERIT  480
QMQRLTNIIT TEDIVTVVTM VTNVDFPPKE SSL                               513

SEQ ID NO: 76              moltype = AA   length = 109
FEATURE                    Location/Qualifiers
source                     1..109
                           mol_type = protein
                           organism = synthetic construct
SEQUENCE: 76
GAILGRSETQ ECLFFNANWE KDRTNQTGVE PCYGDKDKRR HCFATWANIS GSIEIVKQGC  60
WLDDINCYDR TDCVEKKDSP EVYFCCCEGN MCNEKFSYFP EMEVTQPTS             109

SEQ ID NO: 77              moltype = AA   length = 109
FEATURE                    Location/Qualifiers
source                     1..109
                           mol_type = protein
                           organism = synthetic construct
SEQUENCE: 77
GAILGRSETQ ECLFFNANWA KDRTNQTGVE PCYGDKDKRR HCFATWKNIS GSIEIVKQGC  60
WLDDINCYDR TDCVEKKDSP EVYFCCCEGN MCNEKFSYFP EMEVTQPTS             109

SEQ ID NO: 78              moltype = AA   length = 109
FEATURE                    Location/Qualifiers
source                     1..109
                           mol_type = protein
                           organism = synthetic construct
SEQUENCE: 78
GAILGRSETQ ECLFFNANWE KDATNQTGVE PCYGDKDKRR HCFATWKNIS GSIEIVKQGC  60
WLDDINCYDR TDCVEKKDSP EVYFCCCEGN MCNEKFSYFP EMEVTQPTS             109

SEQ ID NO: 79              moltype = AA   length = 109
FEATURE                    Location/Qualifiers
source                     1..109
                           mol_type = protein
                           organism = synthetic construct
SEQUENCE: 79
GAILGRSETQ ECLFFNANWE KDRTNQTGVE PCYGDKAKRR HCFATWKNIS GSIEIVKQGC  60
WLDDINCYDR TDCVEKKDSP EVYFCCCEGN MCNEKFSYFP EMEVTQPTS             109

SEQ ID NO: 80              moltype = AA   length = 109
FEATURE                    Location/Qualifiers
source                     1..109
                           mol_type = protein
                           organism = synthetic construct
SEQUENCE: 80
GAILGRSETQ ECLFFNANWE KDRTNQTGVE PCYGDKDARR HCFATWKNIS GSIEIVKQGC  60
WLDDINCYDR TDCVEKKDSP EVYFCCCEGN MCNEKFSYFP EMEVTQPTS             109

SEQ ID NO: 81              moltype = AA   length = 109
FEATURE                    Location/Qualifiers
source                     1..109
                           mol_type = protein
                           organism = synthetic construct
```

-continued

```
SEQUENCE: 81
GAILGRSETQ ECLFFNANWE KDRTNQTGVE PCYGDKDKAR HCFATWKNIS GSIEIVKQGC    60
WLDDINCYDR TDCVEKKDSP EVYFCCCEGN MCNEKFSYFP EMEVTQPTS               109

SEQ ID NO: 82              moltype = AA  length = 109
FEATURE                    Location/Qualifiers
source                     1..109
                           mol_type = protein
                           organism = synthetic construct
SEQUENCE: 82
GAILGRSETQ ECLFFNANWE KDRTNQTGVE PCYGDKDKRR HCFATWKNIS GSIEIVAQGC    60
WLDDINCYDR TDCVEKKDSP EVYFCCCEGN MCNEKFSYFP EMEVTQPTS               109

SEQ ID NO: 83              moltype = AA  length = 109
FEATURE                    Location/Qualifiers
source                     1..109
                           mol_type = protein
                           organism = synthetic construct
SEQUENCE: 83
GAILGRSETQ ECLFFNANWE KDRTNQTGVE PCYGDKDKRR HCFATWKNIS GSIEIVYQGC    60
WLDDINCYDR TDCVEKKDSP EVYFCCCEGN MCNEKFSYFP EMEVTQPTS               109

SEQ ID NO: 84              moltype = AA  length = 109
FEATURE                    Location/Qualifiers
source                     1..109
                           mol_type = protein
                           organism = synthetic construct
SEQUENCE: 84
GAILGRSETQ ECLFFNANWE KDRTNQTGVE PCYGDKDKRR HCFATWKNIS GSIEIVFQGC    60
WLDDINCYDR TDCVEKKDSP EVYFCCCEGN MCNEKFSYFP EMEVTQPTS               109

SEQ ID NO: 85              moltype = AA  length = 109
FEATURE                    Location/Qualifiers
source                     1..109
                           mol_type = protein
                           organism = synthetic construct
SEQUENCE: 85
GAILGRSETQ ECLFFNANWE KDRTNQTGVE PCYGDKDKRR HCFATWKNIS GSIEIVIQGC    60
WLDDINCYDR TDCVEKKDSP EVYFCCCEGN MCNEKFSYFP EMEVTQPTS               109

SEQ ID NO: 86              moltype = AA  length = 109
FEATURE                    Location/Qualifiers
source                     1..109
                           mol_type = protein
                           organism = synthetic construct
SEQUENCE: 86
GAILGRSETQ ECLFFNANWE KDRTNQTGVE PCYGDKDKRR HCFATWKNIS GSIEIVKQGC    60
ALDDINCYDR TDCVEKKDSP EVYFCCCEGN MCNEKFSYFP EMEVTQPTS               109

SEQ ID NO: 87              moltype = AA  length = 109
FEATURE                    Location/Qualifiers
source                     1..109
                           mol_type = protein
                           organism = synthetic construct
SEQUENCE: 87
GAILGRSETQ ECLFFNANWE KDRTNQTGVE PCYGDKDKRR HCFATWKNIS GSIEIVKQGC    60
WADDINCYDR TDCVEKKDSP EVYFCCCEGN MCNEKFSYFP EMEVTQPTS               109

SEQ ID NO: 88              moltype = AA  length = 109
FEATURE                    Location/Qualifiers
source                     1..109
                           mol_type = protein
                           organism = synthetic construct
SEQUENCE: 88
GAILGRSETQ ECLFFNANWE KDRTNQTGVE PCYGDKDKRR HCFATWKNIS GSIEIVKQGC    60
WLKDINCYDR TDCVEKKDSP EVYFCCCEGN MCNEKFSYFP EMEVTQPTS               109

SEQ ID NO: 89              moltype = AA  length = 109
FEATURE                    Location/Qualifiers
source                     1..109
                           mol_type = protein
                           organism = synthetic construct
SEQUENCE: 89
GAILGRSETQ ECLFFNANWE KDRTNQTGVE PCYGDKDKRR HCFATWKNIS GSIEIVKQGC    60
WLRDINCYDR TDCVEKKDSP EVYFCCCEGN MCNEKFSYFP EMEVTQPTS               109

SEQ ID NO: 90              moltype = AA  length = 109
FEATURE                    Location/Qualifiers
source                     1..109
```

```
                       mol_type = protein
                       organism = synthetic construct
SEQUENCE: 90
GAILGRSETQ ECLFFNANWE KDRTNQTGVE PCYGDKDKRR HCFATWKNIS GSIEIVKQGC   60
WLADINCYDR TDCVEKKDSP EVYFCCCEGN MCNEKFSYFP EMEVTQPTS               109

SEQ ID NO: 91          moltype = AA   length = 109
FEATURE                Location/Qualifiers
source                 1..109
                       mol_type = protein
                       organism = synthetic construct
SEQUENCE: 91
GAILGRSETQ ECLFFNANWE KDRTNQTGVE PCYGDKDKRR HCFATWKNIS GSIEIVKQGC   60
WLFDINCYDR TDCVEKKDSP EVYFCCCEGN MCNEKFSYFP EMEVTQPTS               109

SEQ ID NO: 92          moltype = AA   length = 109
FEATURE                Location/Qualifiers
source                 1..109
                       mol_type = protein
                       organism = synthetic construct
SEQUENCE: 92
GAILGRSETQ ECLFFNANWE KDRTNQTGVE PCYGDKDKRR HCFATWKNIS GSIEIVKQGC   60
WLGDINCYDR TDCVEKKDSP EVYFCCCEGN MCNEKFSYFP EMEVTQPTS               109

SEQ ID NO: 93          moltype = AA   length = 109
FEATURE                Location/Qualifiers
source                 1..109
                       mol_type = protein
                       organism = synthetic construct
SEQUENCE: 93
GAILGRSETQ ECLFFNANWE KDRTNQTGVE PCYGDKDKRR HCFATWKNIS GSIEIVKQGC   60
WLMDINCYDR TDCVEKKDSP EVYFCCCEGN MCNEKFSYFP EMEVTQPTS               109

SEQ ID NO: 94          moltype = AA   length = 109
FEATURE                Location/Qualifiers
source                 1..109
                       mol_type = protein
                       organism = synthetic construct
SEQUENCE: 94
GAILGRSETQ ECLFFNANWE KDRTNQTGVE PCYGDKDKRR HCFATWKNIS GSIEIVKQGC   60
WLNDINCYDR TDCVEKKDSP EVYFCCCEGN MCNEKFSYFP EMEVTQPTS               109

SEQ ID NO: 95          moltype = AA   length = 109
FEATURE                Location/Qualifiers
source                 1..109
                       mol_type = protein
                       organism = synthetic construct
SEQUENCE: 95
GAILGRSETQ ECLFFNANWE KDRTNQTGVE PCYGDKDKRR HCFATWKNIS GSIEIVKQGC   60
WLIDINCYDR TDCVEKKDSP EVYFCCCEGN MCNEKFSYFP EMEVTQPTS               109

SEQ ID NO: 96          moltype = AA   length = 109
FEATURE                Location/Qualifiers
source                 1..109
                       mol_type = protein
                       organism = synthetic construct
SEQUENCE: 96
GAILGRSETQ ECLFFNANWE KDRTNQTGVE PCYGDKDKRR HCFATWKNIS GSIEIVKQGC   60
WLDDANCYDR TDCVEKKDSP EVYFCCCEGN MCNEKFSYFP EMEVTQPTS               109

SEQ ID NO: 97          moltype = AA   length = 225
FEATURE                Location/Qualifiers
source                 1..225
                       mol_type = protein
                       organism = Homo sapiens
SEQUENCE: 97
THTCPPCPAP ELLGGPSVFL FPPKPKDTLM ISRTPEVTCV VVDVSHEDPE VKFNWYVDGV   60
EVHNAKTKPR EEQYNSTYRV VSVLTVLHQD WLNGKEYKCK VSNKALPVPI EKTISKAKGQ  120
PREPQVYTLP PSREEMTKNQ VSLTCLVKGF YPSDIAVEWE SNGQPENNYK TTPPVLDSDG  180
PFFLYSKLTV DKSRWQQGNV FSCSVMHEAL HNHYTQKSLS LSPGK                  225

SEQ ID NO: 98          moltype = AA   length = 4
FEATURE                Location/Qualifiers
source                 1..4
                       mol_type = protein
                       organism = synthetic construct
SEQUENCE: 98
GGGA                                                                 4
```

-continued

```
SEQ ID NO: 99          moltype = AA   length = 4
FEATURE                Location/Qualifiers
source                 1..4
                       mol_type = protein
                       organism = synthetic construct
SEQUENCE: 99
GGGS                                                                      4

SEQ ID NO: 100         moltype = AA   length = 4
FEATURE                Location/Qualifiers
source                 1..4
                       mol_type = protein
                       organism = synthetic construct
SEQUENCE: 100
GGGG                                                                      4

SEQ ID NO: 101         moltype = AA   length = 5
FEATURE                Location/Qualifiers
source                 1..5
                       mol_type = protein
                       organism = synthetic construct
SEQUENCE: 101
GGGGA                                                                     5

SEQ ID NO: 102         moltype = AA   length = 5
FEATURE                Location/Qualifiers
source                 1..5
                       mol_type = protein
                       organism = synthetic construct
SEQUENCE: 102
GGGGS                                                                     5

SEQ ID NO: 103         moltype = AA   length = 5
FEATURE                Location/Qualifiers
source                 1..5
                       mol_type = protein
                       organism = synthetic construct
SEQUENCE: 103
GGGGG                                                                     5

SEQ ID NO: 104         moltype = AA   length = 4
FEATURE                Location/Qualifiers
source                 1..4
                       mol_type = protein
                       organism = synthetic construct
SEQUENCE: 104
GGAG                                                                      4

SEQ ID NO: 105         moltype = AA   length = 4
FEATURE                Location/Qualifiers
source                 1..4
                       mol_type = protein
                       organism = synthetic construct
SEQUENCE: 105
GGSG                                                                      4

SEQ ID NO: 106         moltype = AA   length = 4
FEATURE                Location/Qualifiers
source                 1..4
                       mol_type = protein
                       organism = synthetic construct
SEQUENCE: 106
AGGG                                                                      4

SEQ ID NO: 107         moltype = AA   length = 4
FEATURE                Location/Qualifiers
source                 1..4
                       mol_type = protein
                       organism = synthetic construct
SEQUENCE: 107
SGGG                                                                      4

SEQ ID NO: 108         moltype = AA   length = 4
FEATURE                Location/Qualifiers
source                 1..4
                       mol_type = protein
                       organism = synthetic construct
SEQUENCE: 108
GAGA                                                                      4
```

```
SEQ ID NO: 109            moltype = AA   length = 4
FEATURE                   Location/Qualifiers
source                    1..4
                          mol_type = protein
                          organism = synthetic construct
SEQUENCE: 109
GSGS                                                                      4

SEQ ID NO: 110            moltype = AA   length = 6
FEATURE                   Location/Qualifiers
source                    1..6
                          mol_type = protein
                          organism = synthetic construct
SEQUENCE: 110
GAGAGA                                                                    6

SEQ ID NO: 111            moltype = AA   length = 6
FEATURE                   Location/Qualifiers
source                    1..6
                          mol_type = protein
                          organism = synthetic construct
SEQUENCE: 111
GSGSGS                                                                    6

SEQ ID NO: 112            moltype = AA   length = 8
FEATURE                   Location/Qualifiers
source                    1..8
                          mol_type = protein
                          organism = synthetic construct
SEQUENCE: 112
GAGAGAGA                                                                  8

SEQ ID NO: 113            moltype = AA   length = 8
FEATURE                   Location/Qualifiers
source                    1..8
                          mol_type = protein
                          organism = synthetic construct
SEQUENCE: 113
GSGSGSGS                                                                  8

SEQ ID NO: 114            moltype = AA   length = 10
FEATURE                   Location/Qualifiers
source                    1..10
                          mol_type = protein
                          organism = synthetic construct
SEQUENCE: 114
GAGAGAGAGA                                                                10

SEQ ID NO: 115            moltype = AA   length = 10
FEATURE                   Location/Qualifiers
source                    1..10
                          mol_type = protein
                          organism = synthetic construct
SEQUENCE: 115
GSGSGSGSGS                                                                10

SEQ ID NO: 116            moltype = AA   length = 12
FEATURE                   Location/Qualifiers
source                    1..12
                          mol_type = protein
                          organism = synthetic construct
SEQUENCE: 116
GAGAGAGAGA GA                                                             12

SEQ ID NO: 117            moltype = AA   length = 12
FEATURE                   Location/Qualifiers
source                    1..12
                          mol_type = protein
                          organism = synthetic construct
SEQUENCE: 117
GSGSGSGSGS GS                                                             12

SEQ ID NO: 118            moltype = AA   length = 6
FEATURE                   Location/Qualifiers
source                    1..6
                          mol_type = protein
                          organism = synthetic construct
SEQUENCE: 118
```

-continued

```
GGAGGA                                                                        6

SEQ ID NO: 119         moltype = AA  length = 6
FEATURE                Location/Qualifiers
source                 1..6
                       mol_type = protein
                       organism = synthetic construct SEQUENCE: 119
GGSGGS                                                                        6

SEQ ID NO: 120         moltype = AA  length = 9
FEATURE                Location/Qualifiers
source                 1..9
                       mol_type = protein
                       organism = synthetic construct SEQUENCE: 120
GGAGGAGGA                                                                     9

SEQ ID NO: 121         moltype = AA  length = 9
FEATURE                Location/Qualifiers
source                 1..9
                       mol_type = protein
                       organism = synthetic construct SEQUENCE: 121
GGSGGSGGS                                                                     9

SEQ ID NO: 122         moltype = AA  length = 12
FEATURE                Location/Qualifiers
source                 1..12
                       mol_type = protein
                       organism = synthetic construct SEQUENCE: 122
GGAGGAGGAG GA                                                                12

SEQ ID NO: 123         moltype = AA  length = 12
FEATURE                Location/Qualifiers
source                 1..12
                       mol_type = protein
                       organism = synthetic construct SEQUENCE: 123
GGSGGSGGSG GS                                                                12

SEQ ID NO: 124         moltype = AA  length = 8
FEATURE                Location/Qualifiers
source                 1..8
                       mol_type = protein
                       organism = synthetic construct SEQUENCE: 124
GGAGGGAG                                                                      8

SEQ ID NO: 125         moltype = AA  length = 8
FEATURE                Location/Qualifiers
source                 1..8
                       mol_type = protein
                       organism = synthetic construct SEQUENCE: 125
GGSGGGSG                                                                      8

SEQ ID NO: 126         moltype = AA  length = 12
FEATURE                Location/Qualifiers
source                 1..12
                       mol_type = protein
                       organism = synthetic construct SEQUENCE: 126
GGAGGGAGGG AG                                                                12

SEQ ID NO: 127         moltype = AA  length = 12
FEATURE                Location/Qualifiers
source                 1..12
                       mol_type = protein
                       organism = synthetic construct SEQUENCE: 127
GGSGGGSGGG SG                                                                12

SEQ ID NO: 128         moltype = AA  length = 15
FEATURE                Location/Qualifiers
source                 1..15
                       mol_type = protein
                       organism = synthetic construct
```

-continued

```
SEQUENCE: 128
GGGGAGGGGA GGGGA                                                              15

SEQ ID NO: 129        moltype = AA  length = 15
FEATURE               Location/Qualifiers
source                1..15
                      mol_type = protein
                      organism = synthetic construct
SEQUENCE: 129
GGGGSGGGGS GGGGS                                                              15

SEQ ID NO: 130        moltype = AA  length = 5
FEATURE               Location/Qualifiers
source                1..5
                      mol_type = protein
                      organism = synthetic construct
SEQUENCE: 130
GGGAG                                                                          5

SEQ ID NO: 131        moltype = AA  length = 6
FEATURE               Location/Qualifiers
source                1..6
                      mol_type = protein
                      organism = synthetic construct
SEQUENCE: 131
GGGAGG                                                                         6

SEQ ID NO: 132        moltype = AA  length = 7
FEATURE               Location/Qualifiers
source                1..7
                      mol_type = protein
                      organism = synthetic construct
SEQUENCE: 132
GGGAGGG                                                                        7

SEQ ID NO: 133        moltype = AA  length = 4
FEATURE               Location/Qualifiers
source                1..4
                      mol_type = protein
                      organism = synthetic construct
SEQUENCE: 133
AAAL                                                                           4

SEQ ID NO: 134        moltype = AA  length = 4
FEATURE               Location/Qualifiers
source                1..4
                      mol_type = protein
                      organism = synthetic construct
SEQUENCE: 134
AAAK                                                                           4

SEQ ID NO: 135        moltype = AA  length = 4
FEATURE               Location/Qualifiers
source                1..4
                      mol_type = protein
                      organism = synthetic construct
SEQUENCE: 135
AAAR                                                                           4

SEQ ID NO: 136        moltype = AA  length = 14
FEATURE               Location/Qualifiers
source                1..14
                      mol_type = protein
                      organism = synthetic construct
SEQUENCE: 136
EGKSSGSGSE SKST                                                               14

SEQ ID NO: 137        moltype = AA  length = 12
FEATURE               Location/Qualifiers
source                1..12
                      mol_type = protein
                      organism = synthetic construct
SEQUENCE: 137
GSAGSAAGSG EF                                                                 12

SEQ ID NO: 138        moltype = AA  length = 12
FEATURE               Location/Qualifiers
source                1..12
                      mol_type = protein
```

-continued

```
                            organism = synthetic construct
SEQUENCE: 138
AEAAAKEAAA KA                                                      12

SEQ ID NO: 139           moltype = AA   length = 18
FEATURE                  Location/Qualifiers
source                   1..18
                         mol_type = protein
                         organism = synthetic construct
SEQUENCE: 139
KESGSVSSEQ LAQFRSLD                                                18

SEQ ID NO: 140           moltype = AA   length = 10
FEATURE                  Location/Qualifiers
source                   1..10
                         mol_type = protein
                         organism = synthetic construct
SEQUENCE: 140
GENLYFQSGG                                                         10

SEQ ID NO: 141           moltype = AA   length = 8
FEATURE                  Location/Qualifiers
source                   1..8
                         mol_type = protein
                         organism = synthetic construct
SEQUENCE: 141
SACYCELS                                                           8

SEQ ID NO: 142           moltype = AA   length = 5
FEATURE                  Location/Qualifiers
source                   1..5
                         mol_type = protein
                         organism = synthetic construct
SEQUENCE: 142
RSIAT                                                              5

SEQ ID NO: 143           moltype = AA   length = 17
FEATURE                  Location/Qualifiers
source                   1..17
                         mol_type = protein
                         organism = synthetic construct
SEQUENCE: 143
RPACKIPNDL KQKVMNH                                                 17

SEQ ID NO: 144           moltype = AA   length = 36
FEATURE                  Location/Qualifiers
source                   1..36
                         mol_type = protein
                         organism = synthetic construct
SEQUENCE: 144
GGSAGGSGSG SSGGSSGASG TGTAGGTGSG SGTGSG                            36

SEQ ID NO: 145           moltype = AA   length = 17
FEATURE                  Location/Qualifiers
source                   1..17
                         mol_type = protein
                         organism = synthetic construct
SEQUENCE: 145
AAANSSIDLI SVPVDSR                                                 17

SEQ ID NO: 146           moltype = AA   length = 36
FEATURE                  Location/Qualifiers
source                   1..36
                         mol_type = protein
                         organism = synthetic construct
SEQUENCE: 146
GGSGGGSEGG GSEGGGSEGG GSEGGGSEGG GSGGGS                            36

SEQ ID NO: 147           moltype = AA   length = 5
FEATURE                  Location/Qualifiers
source                   1..5
                         mol_type = protein
                         organism = synthetic construct
SEQUENCE: 147
EAAAK                                                              5

SEQ ID NO: 148           moltype = AA   length = 5
FEATURE                  Location/Qualifiers
source                   1..5
```

```
                              mol_type = protein
                              organism = synthetic construct
SEQUENCE: 148
PAPAP                                                              5

SEQ ID NO: 149          moltype = AA  length = 115
FEATURE                 Location/Qualifiers
source                  1..115
                        mol_type = protein
                        organism = synthetic construct
SEQUENCE: 149
GRGEAETREC IFYNANWEKD RTNQSGLEPC YGDQDKRRHC FASWKNSSGT IELVKQGCWL   60
DDINCYDRQE CVAKKDSPEV YFCCCEGNFC NERFTHLPEA GGPEVTYEPP PTAPT       115

SEQ ID NO: 150          moltype = AA  length = 109
FEATURE                 Location/Qualifiers
source                  1..109
                        mol_type = protein
                        organism = synthetic construct
SEQUENCE: 150
GAILGRSETQ ECLFYNANWE LERTNQTGVE RCEGEKDKRL HCYATWRNIS GSIEIVAKGC   60
WLDDFNCYDR TDCVETEENP QVYFCCCEGN MCNEKFSYFP EMEVTQPTS             109

SEQ ID NO: 151          moltype = AA  length = 246
FEATURE                 Location/Qualifiers
source                  1..246
                        mol_type = protein
                        organism = Homo sapiens
SEQUENCE: 151
MEWSWVFLFF LSVTTGVHSD KTHTCPPCPA PELLGGPSVF LFPPKPKDTL MISRTPEVTC   60
VVVDVSHEDP EVKFNWYVDG VEVHNAKTKP REEQYNSTYR VVSVLTVLHQ DWLNGKEYKC  120
KVSNKALPAP IEKTISKAKG QPREPQVYTL PPSRDELTKN QVSLTCLVKG FYPSDIAVEW  180
ESNGQPENNY KTTPPVLDSD GSFFLYSKLT VDKSRWQQGN VFSCSVMHEA LHNHYTQKSL  240
SLSPGK                                                             246

SEQ ID NO: 152          moltype = AA  length = 11
FEATURE                 Location/Qualifiers
source                  1..11
                        mol_type = protein
                        organism = synthetic construct
SEQUENCE: 152
DICLPRWGCL W                                                       11

SEQ ID NO: 153          moltype = AA  length = 93
FEATURE                 Location/Qualifiers
source                  1..93
                        mol_type = protein
                        organism = Homo sapiens
SEQUENCE: 153
GPVEVFITET PSQPNSHPIQ WNAPQPSHIS KYILRWRPKN SVGRWKEATI PGHLNSYTIK   60
GLKPGVVYEG QLISIQQYGH QEVTRFDFTT TST                                93

SEQ ID NO: 154          moltype = AA  length = 609
FEATURE                 Location/Qualifiers
source                  1..609
                        mol_type = protein
                        organism = Homo sapiens
SEQUENCE: 154
MKWVTFISLL FLFSSAYSRG VFRRDAHKSE VAHRFKDLGE ENFKALVLIA FAQYLQQCPF   60
EDHVKLVNEV TEFAKTCVAD ESAENCDKSL HTLFGDKLCT VATLRETYGE MADCCAKQEP  120
ERNECFLQHK DDNPNLPRLV RPEVDVMCTA FHDNEETFLK KYLYEIARRH PYFYAPELLF  180
FAKRYKAAFT ECCQAADKAA CLLPKLDELR DEGKASSAKQ RLKCASLQKF GERAFKAWAV  240
ARLSQRFPKA EFAEVSKLVT DLTKVHTECC HGDLLECADD RADLAKYICE NQDSISSKLV  300
ECCEKPLLEK SHCIAEVEND EMPADLPSLA ADFVESKDVC KNYAEAKDVF LGMFLYEYAR  360
RHPDYSVVLL LRLAKTYETT LEKCCAAADP HECYAKVFDE FKPLVEEPQN LIKQNCELFE  420
QLGEYKFQNA LLVRYTKKVP QVSTPTLVEV SRNLGKVGSK CCKHPEAKRM PCAEDYLSVV  480
LNQLCVLHEK TPVSDRVTKC CTESLVNRRP CFSALEVDET YVPKEFNAET FTFHADICTL  540
SEKERQIKKQ TALVELVKHK PKATKEQLKA VMDDFAAFVE KCCKADDKET CFAEEGKKLV  600
AASQAALGL                                                          609

SEQ ID NO: 155          moltype = AA  length = 6
FEATURE                 Location/Qualifiers
source                  1..6
                        mol_type = protein
                        organism = Homo sapiens
SEQUENCE: 155
NPVTPK                                                             6

SEQ ID NO: 156          moltype = AA  length = 4
```

```
FEATURE                 Location/Qualifiers
source                  1..4
                        mol_type = protein
                        organism = Homo sapiens
SEQUENCE: 156
TEEN                                                                4

SEQ ID NO: 157          moltype = AA  length = 4
FEATURE                 Location/Qualifiers
source                  1..4
                        mol_type = protein
                        organism = synthetic construct
SEQUENCE: 157
TKEN                                                                4

SEQ ID NO: 158          moltype = AA  length = 4
FEATURE                 Location/Qualifiers
source                  1..4
                        mol_type = protein
                        organism = Homo sapiens
SEQUENCE: 158
VTPK                                                                4

SEQ ID NO: 159          moltype = AA  length = 81
FEATURE                 Location/Qualifiers
source                  1..81
                        mol_type = protein
                        organism = Homo sapiens
SEQUENCE: 159
CLFFNANWEK DRTNQTGVEP CYGDKDKRRH CFATWKNISG SIEIVKQGCW LDDINCYDRT  60
DCVEKKDSPE VYFCCCEGNM C                                             81

SEQ ID NO: 160          moltype = AA  length = 81
FEATURE                 Location/Qualifiers
source                  1..81
                        mol_type = protein
                        organism = Homo sapiens
SEQUENCE: 160
CIYYNANWEL ERTNQSGLER CEGEQDKRLH CYASWRNSSG TIELVKKGCW LDDFNCYDRQ  60
ECVATEENPQ VYFCCCEGNF C                                             81

SEQ ID NO: 161          moltype = AA  length = 10
FEATURE                 Location/Qualifiers
source                  1..10
                        mol_type = protein
                        organism = synthetic construct
VARIANT                 1
                        note = Any amino acid
VARIANT                 3
                        note = Any amino acid
VARIANT                 5
                        note = Any amino acid
VARIANT                 7
                        note = Any amino acid
VARIANT                 9
                        note = Any amino acid
VARIANT                 1..10
                        note = This sequence may encompass 1-5 XP repeating units
SEQUENCE: 161
XPXPXPXPXP                                                          10
```